(12) United States Patent
Jackson et al.

(10) Patent No.: US 7,314,758 B2
(45) Date of Patent: Jan. 1, 2008

(54) NUCLEOTIDE SEQUENCES ENCODING RAMOSA3 AND SISTER OF RAMOSA3 AND METHODS OF USE FOR SAME

(75) Inventors: David Peter Jackson, New York, NY (US); Namiko Nagasawa, Huntington, NY (US); Nobuhiro Nagasawa, Newark, DE (US); Hajime Sakai, Newark, DE (US)

(73) Assignees: E.I. du Pont de Nemours and Company, Wilmington, DE (US); Cold Spring Harbor Laboratory, Cold Spring Harbor, NY (US)

( * ) Notice: Subject to any disclaimer, the term of this patent is extended or adjusted under 35 U.S.C. 154(b) by 0 days.

(21) Appl. No.: 11/327,740

(22) Filed: Jan. 6, 2006

(65) Prior Publication Data

US 2006/0191040 A1    Aug. 24, 2006

Related U.S. Application Data

(60) Provisional application No. 60/739,857, filed on Nov. 23, 2005, provisional application No. 60/642,273, filed on Jan. 7, 2005.

(51) Int. Cl.
 C12N 15/29    (2006.01)
 C12N 15/00    (2006.01)
 C12N 15/52    (2006.01)
 A01H 1/00    (2006.01)

(52) U.S. Cl. .................... 435/468; 800/290; 800/284; 435/194; 435/320.1; 536/23.1; 536/23.2; 536/23.6

(58) Field of Classification Search .................... None
See application file for complete search history.

(56) References Cited

U.S. PATENT DOCUMENTS 4,945,050 A    7/1990 Sanford et al.
7,214,858 B2    5/2007 Caimi et al.

OTHER PUBLICATIONS

Peng, J. et al., "Green Revolution Genes Encode Mutant Gibberellin Response Modulators," Nature, 1999, 400(6741):pp. 256-261.
Sussex, I.M., "The Evolution Of Plant Architecture," Curr Opin Plant Biol, 2001, 4(1), pp. 33-37.
Ward, S.P., "Shoot Branching", Curr Opin Plant Biol, 2004, 7(1), pp. 73-78.
Postlethwait, S.N, "Characterization Of Development In Maize Through The USe Of Mutants . . . ", Am. J. Bot., 1964, 51, pp. 238-243.
Volbrecht, E., "Architecture Of Floral Branch System . . . " Nature, Aug. 2005, 436:1119-1126.
Nickerson, N.H., "Tassel Modification InZea Mays," Ann. MO Bot. Gard., 42, 195-211 (1955).
Hayes, H.K., Recent Linkage Studies IN Maize, Genetics, 1939, 24, pp. 61-63.
Perry, H.S., Unpublished, http://www.maizegdb.org/ , 1954.
Veit, B. et al., "Maize Floral Development: New Genes And Old Mutants," Plant Cell, 5:1205-1215 (1993).
Goddijn, O.J. et al., "Trehalose Metabolism In Plants," Trends Plant Sci, 1999, 4(8), pp. 315-319.
Elbein, A.D., "The Metabolism Of alpha,alpha-Trehalose," Adv. Carbohydr. Chem Biochem. 1974, 30(227-56).
Crowe, J.H. et al., "Anhydrobiosis," Annu Rev Physiol, 1992, 54, pp. 579-599.
Strom, A.R., "Trehalose Metabolism In Escherichia Coli: Stress Protection And Stress Regulation Of Gene Expression," Mol Microbiol, 1993, 8(2), pp. 205-210.
Paiva, C.L., "Biotechnological Applications Of The Disaccharide Trehalose", Biotechnol Annu Rev, 1996, 2, pp. 293-314.
Muller, J., "Trehalose And Trehalase In Plants: Recent Developments," Plant Sci, 1995, 112, pp. 1-9.
Holmstrom, K.O., "Drought Tolerance In Tobacco," Nature, 1996, 379, pp. 683-684.
Romero, C., "Expression Of The Yeast Trehalose-6-Phosphate Synthase Gene In Transgenic Tobacco Plants: Pleiotropic...," Planta, 1997, 201, pp. 293-297.
Garg, A.K., "Trehalose Accumulation In Rice Plants Confers High Tolerance Levels To Different Abiotic...," Proc Natl Acad Sci, 2002, 99(25), pp. 15898-903.
Goddijn, O.J., "Inhibition Of Trehalase Activity Enhances Trehalose Accumulation In Transgenic Plants,", Plant Physiol, 1997, 113(1), pp. 181-90.
Muller, J., "Trehalose And Trehalase In Arabidopsis," Plant Physiol, 2001, 125(2), pp. 1086-93.
Vogel, G., "Trehalose Metabolism In Arabidopsis: Occurance Of Trehalose And Molecular Cloning...," J Exp Bot, 2001, 52(362), pp. 1817-26.
Leyman, B., "An Unexpected Plethora Of Trehalose Biosynthesis Genes In Arabidopsis Thaliana," Trends Plant Sci, 2001, 6(11), pp. 510-513.
Van Dijck, P., "Truncation Of Arabidopsis Thaliana And Selaginella Lepidophylla Trehalose-6-Phosphate...," Biochem J, 2002, 366:63-71.
Londesborough, J., "Trehalose-6-Phosphase Synthase/Phosphatase Complex From Bakers' Yeast...," J Gen Microbiol, 1991, 137, pp. 323-330.

(Continued)

Primary Examiner—Russell P. Kallis
Assistant Examiner—Brent T Page

(57) ABSTRACT

The invention relates to the isolation and characterization of a maize gene, RAMOSA3 (RA3), responsible for meristem development and inflorescence development including branching. The gene, gene product, and regulatory regions may be used to manipulate branching, meristem growth, inflorescence development and arrangement, and ultimately to improve yield of plants. The invention includes the gene and protein product as well as the use of the same for temporal and spatial expression in transgenic plants to alter plant morphology and affect yield in plants. The invention also includes the gene and protein product for SISTER OF RAMOSA3 (SRA).

8 Claims, 13 Drawing Sheets

OTHER PUBLICATIONS

Figure 1:
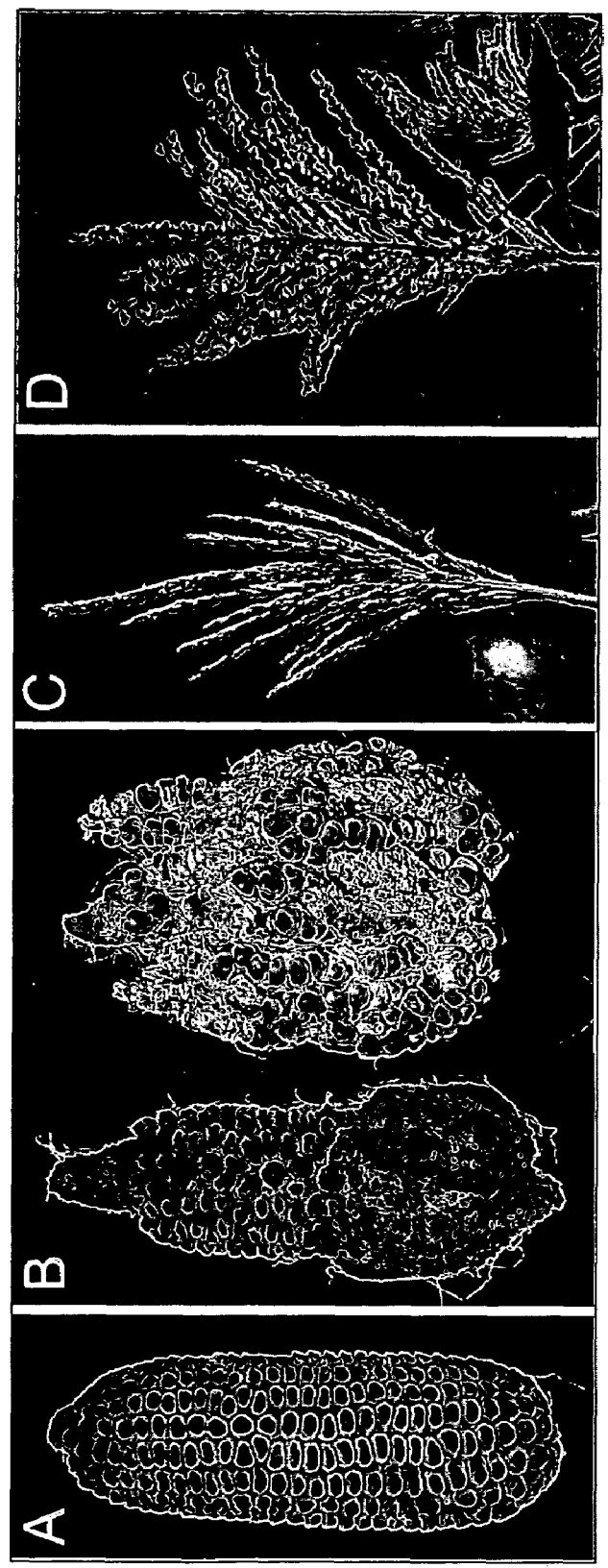

Bell, W., "Composition And Functional Analysis Of The Saccharomyces Cerevisiae Trehalose...," J Biol Chem, 1998, 273(50), pp. 33311-33319.

Avonce, N., "The Arabidopsis Trehalose-6-P Synthase AtTPS1 Gene Is A Regulator Of Glucose...," Plant Physiol, 2004, 136(3), pp. 3649-3659.

Thaller, M.C., "Conserved Sequence Motifs Among Bacterial, Eukaryotic, And Archael Phosphatases...," Protein Sci, 1998, 7(7), pp. 1647-52.

Vogel, G., "Trehalose-6-Phosphate Phosphatases From Arabidopsis Thaliana: Identification By Functional...," Plant J, 1998, 13(5), pp. 673-683.

Paul, M. et al, "Enhancing Photosynthesis With Sugar Signals," Trends Plant Sci, 2001, 695), pp. 197-200.

Cone, K.C., "Genetic, Physical, And Informatics Resources For Maize. On The Road To An Integrated Map," Plant Physiol, 2002, 130(4), pp. 1598-1605.

De Virgilio, C. et al., "Disruption Of TPS2, The Gene Encoding The 100-kDa Subunit Of The Trehalose...," Eur J Biochem 212:315-323 (1993).

Chen, J. et al (1975), "The Important Role Of Historical Flood Data in The Estimation Of Spillway Design Floods," Sci Sin Peking, 18:659-668.

Klein, T.M. et al, 1987, "High-Velocity Microprojectiles For Delivering Nucleic Acids Into Living Cells," Nature, 1997, 327:70-73.

Fromm, M. et al, "Inheritance And Expression Of Chimeric Genes In The Progeny Of Transgenic Maize Plants," Bio/Technology, 8:833-839 (1990).

Gritz, L. et al, 1983, "Plasmid-Encoded Hygromycin B Resistance: The Sequence Of Hygromycin B Phosphotransferase Gene...," Gene 25:179-187.

Rosenberg, A. et al, 1987, "Vectors For Selective Expression Of Cloned DNAs By T7 RNA Polymerase," Gene 56:125-135.

Studier, F. et al, 1986, "Use Of Bacteriophage T7 RNA Polymerase To Direct Selective High-Level Expression...", J Mol Biol, 1986, 189:113-130.

Klutts, S. et al., "Purification, Cloning, Expression, And Properties of Mycobacterial Trehalose...," J Biol Chem, 278:2093-2100 (2003).

Minet, M. et al., "Complementation of Saccharomyces Cerevisiae Auxotrphic Mutants By Arabidopsis...," Plant J, 2:417-422 (1992).

FIG. 6A

```
SEQ ID NO:19         1 MTKHAAYSSEDVVAAVAAP--APAGRH------FTSFQAL-----KGA-----PLDCKKHA
SEQ ID NO:49         1 MTKRTAFAADDAIIAAAAAVTSQPGRR------FTSYPPA-----RAR-----G-GCRLAP
SEQ ID NO:51         1 MTNHAGFAADDAVTAAVPVQAAQGGRH------FPPFLAP-----SSR-----LTDCKKAA
SEQ ID NO:52         1 MD---MKSGHSSPVMTDSPPISNSRLT-IRQNRLPYSSAAATAISQNNNLLLTVPRKKT
SEQ ID NO:53         1 MTNQNVIVSDRKPILGLKTITVSVSNSPLFSNSFPTYFNF-----PRRKLLKLLEAADKN
SEQ ID NO:54         1 MD----MGSGS-SPVITDPISISPPLLGGLTSNLMPFSVMSGGCSSSPS--MSASSRRK-
SEQ ID NO:55         1 MD----LKP-NLNPVLTDATPLTRSRLG-VPSGLSPYSPIGAT-FPHGN--MLAIPRKKT
NO:52 minus 91aa     1 M-----------------------------------------------------------
NO:53 minus 91aa     1 ---------------------------------------------------------60
                                                                                  60

*                    *    ****    *
SEQ ID NO:19        44 AVDLSASGAAVVGG--GPWFEESMKASS--------PRRAADAEHGDWME-KHPSALAQFEP
SEQ ID NO:49        45 AVAAAARQATDDPGAAGSWPELV---V-------PRHA---DFDDWME-KHPSALAAFES
SEQ ID NO:51        46 A-HVDLAGAGGVATVPGSWPRHAKP---------VSGAELDDWME-KHPSALAWFES
SEQ ID NO:52        56 GILDDVKSNGWLDAMKSSSPPPTILNKD-NLSNDAT---DMTYREWMQLKYPSALTSFEK
SEQ ID NO:53        56 NLVVAPKITSMIDSMRDSSPTRLRSSSY-----DSDSDNDDKTSWIV-RFPSALNMFDE
SEQ ID NO:54        53 --IEEVLVNGLLDAMKSSSPRK---KHNLAFGQDNSPDEDPAYTAWLS-KCPSALASFKQ
SEQ ID NO:55        52 GILDDFRSSGWLDAMKSSSPTHTKVSKDVSHGIGSP--DSAYSTWL-LKFPSALASFDQ
NO:52 minus 91aa     2 --------------------------------------TYREWMQLKYPSALTSFEK
NO:53 minus 91aa     1 -----------------------------------------KTSWIV-RFPSALNMFDE
                      61                                                              120
```

FIG. 6B

```
                           *   *********************  **   *  **     *    *  *****  *****       **
SEQ ID NO:19          94   LLAAAKGKQIVMFLDYDGTLSPIVEDPDRAVMSEEMREAVRRVAEHFPTAIVSGRCRDKV
SEQ ID NO:49          91   VLAAAKGKKIVMFLDYDGTLSPIVRDPDSAVMSEEMRDAVRGVAEHFPTAIVSGRCRDKV
SEQ ID NO:51          92   VAAAAKGKEIVVFLDYDGTLSPIVADPDRAFMSDEMREAVRGVAKHFPTAIVSGRCIDKV
SEQ ID NO:52         112   IMSFAKGKRIALFLDYDGTLSPIVEEPDCAYMSSAMRSAVQNVAKYFPTAIISGRSRDKV
SEQ ID NO:53         109   IVNAAKGKQIVMFLDYDGTLSPIVEDPDKAFITHEMREVVKDVASNFPTAIVTGRSIEKV
SEQ ID NO:54         107   IVANAQGRRIAVFLDYDGTLSPIVDDPDKAFMSPVMRAAVRNVAKYFPTAIVSGRSRKKV
SEQ ID NO:55         108   ITNCAKGKRIALFLDYDGTLSPIVDNPDSAFMSDNMRAAVKIVAEYFPTAIISGRSRDKV
NO:52 minus 91aa      21   IMSFAKGKRIALFLDYDGTLSPIVEEPDCAYMSSAMRSAVQNVAKYFPTAIISGRSRDKV
NO:53 minus 91aa      18   IVNAAKGKQIVMFLDYDGTLSPIVEDPDKAFITHEMREVVKDVASNFPTAIVTGRSIEKV
                     121         LDYDGTLSPIVEDP                                      180
                                  A-Domain

*    *    *********** **    **           *   *    * ***
SEQ ID NO:19         154   LNFVKLTELYYAGSHGMDIQGPAACRQP--NHV------QQAEAAAVHYQAASEFLPVIEE
SEQ ID NO:49         151   FNFVKLAELYYAGSHGMDIKGPTA--QS--KHT-----K-AKAGAVLCQPARAFLPVIEE
SEQ ID NO:51         152   FDFVKLEELYYAGSHGMDIRGPTAAASEYNHNM-----KAKQGDAVTFQPAADFLPVIEE
SEQ ID NO:52         172   YEFVNLSELYYAGSHGMDIMSPAGESLNHEHSRTVSVYE-QGKDVNLFQPASEFLPMIDK
SEQ ID NO:53         169   RSFVQVNEIYYAGSHGMDIEGPT-----NENS-----NGQSNERVLFQPAREFLPMIEK
SEQ ID NO:54         167   FEFVKLTELYYAGSHGMDIVTSAA---AHATEKC----KEANLFQPACEFLPMINE
SEQ ID NO:55         168   YEFVGVSDLCYAGSHGMDIIGPSRQSISDNHPDCISSADKQGVEVNLFQPAAEFLPMINE
NO:52 minus 91aa      81   YEFVNLSELYYAGSHGMDIMSPAGESLNHEHSRTVSVYE-QGKDVNLFQPASEFLPMIDK
NO:53 minus 91aa      78   RSFVQVNEIYYAGSHGMDIEGPT-----NENS-----NGQSNERVLFQPAREFLPMIEK
                     181                                                               240
```

FIG. 6C

```
                              *   *          * **    ***  *    **    *    *  *      *        *    *
SEQ ID NO:19           207    VFRTLTAKMESIAGARVEHNKYCLSVHFERCVREEEWNAVNEEVRSVLREYPNLKLTHGRK
SEQ ID NO:49           201    VYRALTASTAPIPGATVENNKFCLSVHFRCVQEEKWRALEEQVRSVLKEYPDLRLTKGRK
SEQ ID NO:51           207    VYHVLKERMASIRGSLVENNKFCLSVHYRCVDEAEWGVLDGKVRAVIEGYPDLRLSKGRK
SEQ ID NO:52           231    VLCSLIESTKDIKGVKVEDNKFCISVHYRNVEEKNWTLVAQCVDDVIRTYPKLRLTHGRK
SEQ ID NO:53           218    VVNILEEKTKWIPGAMVENNKFCLSVHFRRVDEKRWPALAEVVKSVLIDYPKLKLTQGRK
SEQ ID NO:54           216    VSKCLVEVTSSIEGARVENNKFCVSVHYRNVAEKDWKVVAGLVKQVLEAFPRLKVTNGRM
SEQ ID NO:55           228    VLGLLMECTEDIEGATVENNKFCVSVHYRNVDEESWQIVGQRVYDVLKEYPRLRLTHGRK
NO:52 minus 91aa       140    VLCSLIESTKDIKGVKVEDNKFCISVHYRNVEEKNWTLVAQCVDDVIRTYPKLRLTHGRK
NO:53 minus 91aa       127    VVNILEEKTKWIPGAMVENNKFCLSVHFRRVDEKRWPALAEVVKSVLIDYPKLKLTQGRK
                              241                                                          300

***   * ****   * ***  *           *      * ************ *      *  ***
SEQ ID NO:19           267    VLEIRPSIKWDKGKALEFLLKSLGYAGRNDVFPIYIGDDRTDEDAFKVLRN-MGQGIGIL
SEQ ID NO:49           261    VLEIRPSIKWDKGNALQFLLESLGFAGSNSVFPIYIGDDSTDEDAFKVLRN-LGQGIGIL
SEQ ID NO:51           267    VLEIRPVIDWDKGSALQFLLKSLGYEGRNNVFPIYIGDDRTDEDAFKVLRN-MGQGIGIL
SEQ ID NO:52           291    VLEIRPVIDWDKGKAVTFLLESLGLNNCEDVLPIYVGDDRTDEDAFKVLRDGPNHGYGIL
SEQ ID NO:53           278    VLEIRPTIKWDKGQALNFLLKSLGYENSDDVVPIYIGDDRTDEDAFKVLRE-RGQGFGIL
SEQ ID NO:54           276    VLEVRPVIDWDKGKAVEFLLRSLGLSDSEDVVPIYIGDDRTDEDAFKVLRE-RSCGYGIL
SEQ ID NO:55           288    VLEVRPVIDWDKGKAVTFLLESLGLN-CDDVLAIYVGDDRTDEDAFKVLKEA-NKGCGIL
NO:52 minus 91aa       200    VLEIRPVIDWDKGKAVTFLLESLGLNNCEDVLPIYVGDDRTDEDAFKVLRDGPNHGYGIL
NO:53 minus 91aa       187    VLEIRPTIKWDKGQALNFLLKSLGYENSDDVVPIYIGDDRTDEDAFKVLRE-RGQGFGIL
                              301                                                          360

GDDRTDEDAF
                                                              B-Domain
```

FIG. 6D

```
              *    **    *    *  *   *                                   *  **  *
SEQ ID NO:19       326  VSKLPKETAASYSLSDPAEV----------------KEFLRKLAN-KKGARQP----  361
SEQ ID NO:49       320  VSKIPKETRASYSLREPSEVATLPTATSYYCTVEEFLRKLVSWSKESRQR----D  370
SEQ ID NO:51       326  VTKVPKETAASYTLREPSEV------------KEFLRKLVKIKINGDKGLIGK  366
SEQ ID NO:52       351  VSAVPKDSNAFYSLRDPSEVM-----------EFLKSLVTWK----RSMG--  385
SEQ ID NO:53       337  VSKVPKDTNASYSLQDPSQV------------NKFLERLVEWK----RKTVGEE  374
SEQ ID NO:54       335  VSQVPKDTEAFYSVRDPSEVM-----------GFLNSLVRWK----K-HPL  369
SEQ ID NO:55       346  VSRAPKESNAIYSLRDPSEVM-----------EFLTSLAEWK----SSIQAR  382
NO:52 minus 91aa   260  VSAVPKDSNAFYSLRDPSEVM-----------EFLKSLVTWK----RSMG--  294
NO:53 minus 91aa   246  VSKVPKDTNASYSLQDPSQV------------NKFLERLVEWK----RKTVGEE  283
                   361                                                           414
```

NUCLEOTIDE SEQUENCES ENCODING RAMOSA3 AND SISTER OF RAMOSA3 AND METHODS OF USE FOR SAME

This application claims the benefit of U.S. Provisional Application No. 60/642,273, filed Jan. 7, 2005, and U.S. Provisional Application No. 60/739,857, filed Nov. 23, 2005, each of which is hereby incorporated by reference in its entirety.

GOVERNMENT SUPPORT

The invention described herein was made in whole or in part with government support under USDA Award No. 2005-02402 and NSF Award No. DBI-0110189 awarded by the United States Department of Agriculture and the National Science Foundation, respectively. The United States Government has certain rights in the invention.

FIELD OF THE INVENTION

The field of invention relates generally to plant molecular biology, and more specifically, to protein and nucleotide sequences and genetic techniques using the same to modify plant architecture and to increase yield and health of plants.

BACKGROUND OF THE INVENTION

Plant architecture is central to yield, for example in orchestrating the green revolution through reducing plant height [Peng, J. et al., Nature, 1999. 400(6741): p. 256-611]. Similarly, inflorescence morphology is a major yield factor in many crops, and is determined by the activities of shoot meristems. Variations in branching patterns lead to diversity in architectures, and have been studied at the genetic, physiological and molecular levels [Sussex, I. M. and Kerk, N. M., Curr Opin Plant Biol, 2001. 4(1): p. 33-7; Ward, S. P. and Leyser, O., Curr Opin Plant Biol, 2004. 7(1): p. 73-8].

Factors that Control Shoot Branching

The shoot apical meristem (SAM) is active throughout the plant lifecycle, and produces leaves and axillary meristems, typically initiated in each leaf axil. Patterns of axillary meristem activity—where they are produced, whether they undergo dormancy or growth and how much they grow—contribute to overall shoot architecture. Apical dominance is a major factor in regulating development of axillary meristems, and is regulated by genetic and hormonal factors.

Development of axillary meristems can be described in two phases, initiation and growth.

Genes like REVOLUTA (REV) and LATERAL SUPPRESSOR (LAS) in *Arabidopsis* are involved in initiation. rev mutants often fail to produce axillary meristems during both vegetative and reproductive development. REV encodes a homeodomain/leucine zipper transcription factor and is expressed in very early axillary meristems. On the other hand, in las mutants, defects in formation of axillary meristems occur only during vegetative development. LAS is however expressed in leaf axils during both vegetative and reproductive development. LAS also encodes a transcriptional factor, a member of the GRAS family. Expression patterns suggest that LAS acts upstream of REV in axillary meristem development.

The maize teosinte branched1 (tb1) locus is another well-characterized regulator of axillary meristem growth. The tb1 mutant phenotype resembles the maize ancestor, teosinte, in axillary meristem outgrowth. QTL analysis, gene structure and expression analyses indicate that TB1 is one of the major genes involved in the important change of plant architecture involved in the development of maize as a crop. The rice TB1 ortholog appears to act downstream of the rice LAS ortholog, monoculm1.

The regulation of axillary meristem outgrowth is complex, and several genes, as well as the hormones, auxin, cytokinin and abscisic acid (ABA) have been implicated. Auxin is traditionally thought of as an inhibitor of axillary meristem growth, though recent evidence suggests that it also functions during axillary meristem initiation. The importance of auxin for growth is suggested by the fact that auxin resistant1 (axr1) mutants, which have reduced responses to auxin, are highly branched. However, the concentrations of auxin in axillary meristems after decapitation are sometimes higher than before, and auxin appears to act non-autonomously, in the xylem and interfascicular schlerenchyma, to suppress branching. This suggests the existence of mobile second messengers that transmit the auxin signal.

One candidate is for such a signal is a cytokinin. Cytokinins can promote the growth of axillary meristems following direct application, and auxin can down-regulate cytokinin biosynthesis. Further evidence of a role for cytokinin in axillary meristem growth comes from analysis of the *Arabidopsis* hoc and supershoot mutants, which have higher endogenous cytokinin levels and an extremely branched phenotype. Physiological and genetic analyses suggest that the hormone abscisic acid may also regulate the growth of axillary meristems.

Genetic analysis is also beginning to identify novel branching signals. ramosus (rms) mutants in pea and more axillary growth (max) mutants in *Arabidopsis* have a bushy phenotype and auxin resistant bud growth. Grafting experiments, hormone measurements and responses of these mutants to auxin strongly suggested the existence of a novel mobile branch-inhibition signal that functions downstream of auxin. Recent cloning of MAX3 and MAX4 has started to provide some clues as to the nature of this signal. Both genes encode proteins related to dioxygenases, and the hypothesis is that the signal is derived by cleavage of a carotenoid. Analysis of other rms and max mutants has revealed other genes that are not rescued by grafting, and may function in MAX/RMS-dependent signal perception. The fact that MAX2 encodes an F-box protein may match the hypothesis, since many such proteins are involved in hormone regulation.

Factors that Control Inflorescence Branching

Internal and environmental stimuli promote the transition from vegetative SAM to inflorescence meristem (IM), which initiates the inflorescence structures. In grasses, inflorescence development is characterized by the formation of short branches called spikelets. Maize forms two distinct types of inflorescence; the terminal tassel has long branches and develops the male flowers, and the axillary ears have a prominent axis lacking long branches, and develop female flowers. The IM initiates files of spikelet pair meristems (SPMs), and each SPM in turn produces two spikelet meristems (SMs), which initiates two floral meristems (FMs). In the tassel, the IM also initiates several branch meristems (BMs), which are responsible for the long branches at the base of the tassel, followed by SPMs, SMs and FMs as in the ear.

Inflorescence architecture in different species is highly variable, for example in contrast to maize, rice has only one kind of bisexual inflorescence formed from apical and axillary meristems. Each IM produces primary branches in a spiral phyllotaxy, and these make secondary branches and SMs in a biased distichous phyllotaxy. Both primary and secondary branch meristems (BMs) in rice correspond to SPMs in maize inflorescences, from the viewpoint that they initiate SMs. The rice IM degenerates after making primary BMs, and the internodes of both primary and secondary branches elongate to form a panicle architecture, which looks very different from that of maize, though their structural components are essentially the same.

Several genes that regulate maize and rice inflorescence branching and morphology have been identified. BARREN INFLORESCENCE2 (BIF2) and BARREN STALK1 (BA1) in maize, and LAX PANICLE (LAX) in rice control the initiation of axillary IMs. bif2 tassels make fewer or no branches and spikelets, and the ears have fewer or no spikelets. Since the BMs, SPMs, SMs and FMs in weak bif2 mutants are all defective, it appears that BIF2 is required for initiation and maintenance of all types of axillary meristems. ba1 mutants lack vegetative axillary branches and ears, and have unbranched tassels lacking spikelets. In rice lax mutants, the number of primary branches and spikelets is also strongly reduced. These phenotypes indicate that both BA1 and LAX are required to initiate inflorescence axillary meristems. They encode orthologous basic helix-loop-helix transcription factors, and are expressed at the boundaries between pre-existing and newly initiated axillary meristems. These localized expression patterns support the functions of LAX and BA1 in the production of axillary meristems, and suggest that the gene functions are strongly conserved between rice and maize. Zea floricaula l leafy (zfl) mutants in maize also have less tassel branches and fewer ear row numbers in addition to defects during the inflorescence transition.

Once axillary meristems are initiated, they acquire new identities. RAMOSA1 (RA1) in maize is required in the tassel and ear for the transition from SPM to SM identity, and ra1 mutants have highly branched inflorescences [Postlethwait, S. N. and Nelson, O. E., Characterization of development in maize through the use of mutants. I. The polytypic (Pt) and ramosa-1 (ra1) mutants. Am. J. Bot., 1964. 51: p. 238-243; Vollbrecht et al. Nature 436:1119-1126].

Ramosa2 (ra2) mutants have a similar phenotype to ra1 except that in ra2 the pedicellate spikelet is converted to a branch. Nickerson, N. H. et al., Tassel modifications in Zea mays. Ann. MO Bot. Gard., 42, 195-211 (1955); Hayes, H., Recent linkage studies in maize. IV. Ramosa ear-2 (ra2). Genetics, 1939.24: p. 61.

Ramosa3 (ra3) is a classical mutant of maize, first described in 1954 [Perry, H. S., Unpublished, http://www-.maizegdb.org/. 1954] (see also, Table 1 of Veit et al. Plant Cell 5:1205-1215 (1993)), but it has not been characterized in detail. Only the mature inflorescence phenotype has been reported.

In tassel seed4 (ts4) mutants most SPMs in the tassel and those on the distal part of the ear reiterate SPMs, therefore TS4 is required for SM identity. FRIZZY PANICLE (FZP) in rice and BRANCHED SILKLESS1 (BD1) in maize regulate meristem identity at the transition from SMs to FMs. fzp and bd1 mutants produce branching structures without making flowers, so these genes are required to regulate the determinacy of SMs and/or to establish the identity of FMs. FZP and BD1 encode orthologs in the ethylene-responsive element-binding factor class of transcription factors. They are expressed in analogous patterns at the junction of SMs and rudimentary glumes in rice, and SMs and inner/outer glumes in maize. Therefore some genes that regulate inflorescence architecture in rice and maize are strongly conserved in function and expression pattern.

Other genes regulating SM determinacy include the maize REVERSED GERM ORIENTATION1 (RGO1), INDETERMINATE SPIKELET1 (IDS1), INDETERMINATE FLORAL APEX1 (IFA1) and TASSEL SEED6 (TS6) genes. In these mutants, the SMs become more indeterminate, and produce extra flowers. The degree of SPM and SM determinacy is one of the characteristic variables in grass inflorescence architecture, and differs significantly between rice and maize, as described above, and in other grasses, for example, in wheat, the SMs are indeterminate.

Genetic and molecular analyses in model species have contributed to understanding the mechanisms of inflorescence branching in the grasses. Most of the genes that have been isolated encode putative transcription factors, suggesting they regulate the transcription of downstream targets.

Trehalose Biology and Signaling

Trehalose is a disaccharide composed of two glucose units. It is highly resistant to heat and pH and has a strong stabilizing effect on proteins. In contrast to sucrose, which is present only in the plant kingdom and some photosynthetic prokaryotes, trehalose is present in all kingdoms and plays a role in carbohydrate storage and stress protection in microbes and invertebrates. See, e.g., Goddijn, O. J. and van Dun, K., Trehalose metabolism in plants. Trends Plant Sci, 1999. 4(8): p. 315-319; Elbein, A. D., The metabolism of a,a-trehalose. Adv. Carbohydr. Chem. Biochem., 1974. 30(227-56.); Crowe, J. H., Hoekstra, F. A., and Crowe, L. M., Anhydrobiosis. Annu Rev Physiol, 1992. 54: p. 579-99; Strom, A. R. and Kaasen, I., Trehalose metabolism in *Escherichia coli*: stress protection and stress regulation of gene expression. Mol Microbiol, 1993. 8(2): p. 205-10; and Paiva, C. L. and Panek, A. D., Biotechnological applications of the disaccharide trehalose. Biotechnol Annu Rev, 1996. 2: p. 293-314.

Until recently trehalose was not thought to be present in vascular plants, with the exception of desiccation-tolerant plants (reviewed in Muller, J., Boller, T., and Wiemken, A., Trehalose and trehalase in plants: recent developments. Plant Sci., 1995. 112: p. 1-9).

However, interest in the application of engineering trehalose metabolism to produce drought tolerant crops led to the discovery of trehalose biosynthetic genes in plants. See, e.g., Holmstrom, K. O., Mantyla, E., Welin, B., Mandal, A., and Palva, E. T., Drought tolerance in tobacco. Nature, 1996. 379: p. 683-684; Romero, C., Belles, J. M., Vaya, J. L., Serrano, R., and Cilianez-Macia, A., Expression of the yeast trehalose-6-phosphate synthase gene in transgenic tobacco plants: pleiotropic phenotypes include drought tolerance. Planta, 1997. 201: p. 293-297; and Garg, A. K., Kim, J. K., Owens, T. G., Ranwala, A. P., Choi, Y. D., Kochian, L. V., and Wu, R. J., Trehalose accumulation in rice plants confers high tolerance levels to different abiotic stresses. Proc Natl Acad Sci USA, 2002. 99(25): p. 15898-903. See also, e.g., Goddijn, O. J., Verwoerd, T. C., Voogd, E., Krutwagen, R. W., de Graaf, P. T., van Dun, K., Poels, J., Ponstein, A. S., Damm, B., and Pen, J., Inhibition of trehalase activity enhances trehalose accumulation in transgenic plants. Plant Physiol, 1997. 113(1): p. 181-90; Muller, J., Aeschbacher, R. A., Wingler, A., Boller, T., and Wiemken, A., Trehalose and trehalase in *Arabidopsis*. Plant Physiol, 2001. 125(2): p. 1086-93; Vogel, G., Fiehn, O., Jean-Richard-dit-Bressel, L., Boller, T., Wiemken, A., Aeschbacher, R. A., and Wingler, A., Trehalose metabolism in *Arabidopsis*: occurrence of trehalose and molecular cloning and characterization of trehalose-6-phosphate synthase homologues. J Exp Bot, 2001. 52(362): p. 1817-26; and Leyman, B., Van Dijck, P., and Thevelein, J. M., An unexpected plethora of trehalose biosynthesis genes in *Arabidopsis thaliana*. Trends Plant Sci, 2001. 6(11): p. 510-3.

N-terminal deletion of the *Selaginella lepidophylla* (a "resurrection plant") or *Arabidopsis thaliana* trehalose-6-phosphate synthase (TPS1) results in a dramatic increase in TPS activity (Van Dijck et al., 2002, Biochem. J. 366:63-71). This indicates a high potential trehalose synthesis capacity in plants in spite of the near universal absence of trehalose.

The biosynthesis of trehalose occurs in 2 steps, analogous to that of sucrose. Trehalose-6-phosphate (T6P) is first formed from UDP-glucose and glucose-6-phosphate by trehalose-6-phosphate synthase (TPS). Next, T6P is converted to trehalose by trehalose-6-phosphate phosphatase (TPP).

Trehalose metabolism has been analyzed in detail in *Saccharomyces cerevisiae* and *Escherichia coli*. In *S. cerevisiae*, TPS1 is responsible for TPS activity, and TPS2 for TPP activity, and they function in a complex together with regulatory subunits encoded by TPS3 and TSL1 [Londesborough, J. and Vuorio, O., Trehalose-6-phosphate synthase/phosphatase complex from bakers' yeast: purification of a proteolytically activated form. J Gen Microbiol, 1991. 137 (Pt 2): p. 323-30; Bell, W., Sun, W., Hohmann, S., Wera, S., Reinders, A., De Virgilio, C., Wiemken, A., and Thevelein, J. M., Composition and functional analysis of the *Saccharomyces cerevisiae* trehalose synthase complex. J Biol Chem, 1998. 273(50): p. 33311-9].

However in *E. coli*, OtsA, which has TPS activity, and OtsB, which has TPP activity, act independently. In *Arabidopsis*, more than ten homologues have been found for both TPS and TPP genes. Functional analysis of the plant genes has concentrated on the *Arabidopsis* TPS1 gene. Loss-of-function tps1 mutants are embryo lethal, and were not rescued by exogenous trehalose. The tps1 mutants can be rescued by an inducible TPS1 construct, but have reduced root growth, and continued induction is required for the transition to flowering. Plants over-expressing AtTPS1 had increased dehydration (drought) tolerance and were glucose- and ABA-insensitive [Avonce, N., Leyman, B., Mascorro-Gallardo, J. O., Van Dijck, P., Thevelein, J. M., and Iturriaga, G., The *Arabidopsis* trehalose-6-P synthase AtTPS1 gene is a regulator of glucose, abscisic acid, and stress signaling. Plant Physiol, 2004. 136(3): p. 3649-59].

*Arabidopsis* also encodes a number of TPP homologs, encoding proteins with a TPP domain, with highly conserved phosphatase motifs typical of this class of phosphohydrolases [Thaller, M. C., Schippa, S., and Rossolini, G. M., Conserved sequence motifs among bacterial, eukaryotic, and archaeal phosphatases that define a new phosphohydrolase superfamily. Protein Sci, 1998. 7(7): p. 1647-52].

*Arabidopsis* TPP genes were first isolated by their ability to complement yeast tps2 mutants [Leyman, B., Van Dijck, P., and Thevelein, J. M., *An unexpected plethora of trehalose biosynthesis genes in Arabidopsis thaliana*. Trends Plant Sci, 2001. 6(11): p. 510-3; Vogel, G., Aeschbacher, R. A., Muller, J., Boller, T., and Wiemken, A., Trehalose-6-phosphate phosphatases from *Arabidopsis thaliana*: identification by functional complementation of the yeast tps2 mutant.

Plant J, 1998. 13(5): p. 673-83], though no other information is available on the biological functions of these genes.

Trehalose-6-phosphate has also recently emerged as a regulator of carbon metabolism, and appears to act as an enhancer of photosynthetic capacity through interaction with sugar signaling pathways. Plants over-expressing either the bacterial or yeast trehalose biosynthetic genes have altered carbohydrate metabolism, and some morphological defects. These phenotypes are thought to result from changes in carbon allocation between sink and source tissues and provoked speculation that trehalose metabolism may be involved in sugar signaling. Paul et al. (*Enhancing photosynthesis with sugar signals*. Trends Plant Sci, 2001. 6(5): p. 197-200) reasoned that T6P could be the signal that allows hexokinase to perceive carbon status, as is the case in yeast. However this is inconsistent with the fact that T6P is not an inhibitor of *Arabidopsis* hexokinases AtHXK1 and AtHXK2 in vitro, and reducing hexokinase activity did not rescue the growth of *Arabidopsis* tps1 embryos. Nevertheless, an analysis of *Arabidopsis* plants over-expressing OtsA, OtsB and treC (trehalose phosphate hydrolase) also confirms an involvement of T6P in carbohydrate utilization and growth via control of glycolysis.

Trehalose signaling also appears to play a similar role in monocots, since transgenic rice overexpressing *E. coli* OtsA and OtsB had increased trehalose accumulation, and this correlated with more soluble carbohydrates and a higher capacity for photosynthesis under both stress and non-stress conditions. These results are consistent with a role for the trehalose pathway in modulating sugar sensing and carbohydrate metabolism.

In addition to T6P, other signaling steps in the plant trehalose pathway have been proposed. For example, the TPS protein interacts with regulatory 14-3-3 proteins, and this interaction may depend on the cellular sugar status. Trehalose itself may also act as a signal, although it is unlikely to act as an osmoprotectant as in microbes as the concentration is very low. However, a possible target of trehalose is ApL3, an ADP-glucose pyrophosphorylase, which is involved in starch biosynthesis. These data suggest that trehalose interferes with carbon allocation to the sink tissues by inducing starch synthesis in source tissues.

While exact roles of trehalose and related sugars is not clearly understood, sugars in general are thought of as signaling molecules or as global regulators of gene expression. In addition to their obvious metabolic functions, sugars can act like hormones, or can modulate hormone signaling pathways.

SUMMARY OF THE INVENTION

The present invention includes:

An isolated polynucleotide comprising: (a) a nucleic acid sequence encoding a polypeptide having an amino acid sequence of at least 80%, 85%, 90%, 95%, 96%, 97%, 98%, 99% or 100% sequence identity, based on the Clustal V method of alignment, when compared to SEQ ID NO:19, wherein expression of said polypeptide in a plant transformed with said isolated polynucleotide results in alteration of the branching of the tassel, ear, or both, of said transformed plant when compared to a control plant not comprising said isolated polynucleotide; or (b) a complement of the nucleotide sequence, wherein the complement and the nucleotide sequence consist of the same number of nucleotides and are 100% complementary. Preferably, expression of said polypeptide results in a decrease in the branching of the tassel, ear, or both, and even more preferably, the plant is maize.

An isolated polynucleotide comprising: (a) a nucleic acid sequence encoding a polypeptide having an amino acid sequence of at least 80%, 85%, 90%, 95%, 96%, 97%, 98%, 99% or 100% sequence identity, based on the Clustal V method of alignment, when compared to SEQ ID NO:19, wherein expression of said polypeptide in a plant transformed with said isolated polynucleotide results in alteration of pollen shed of said transformed plant when compared to a control plant not comprising said isolated polynucleotide; or (b) a complement of the nucleotide sequence, wherein the complement and the nucleotide sequence consist of the same number of nucleotides and are 100% complementary. Preferably, expression of said polypeptide results in a decrease in pollen shed, and even more preferably, the plant is maize.

An isolated polynucleotide comprising: (a) a nucleotide sequence encoding a polypeptide associated with branching of the tassel, ear, or both, of a plant (preferably maize), wherein said polypeptide has an amino acid sequence of at least 80%, 85%, 90%, 95%, 96%, 97%, 98%, 99% or 100% sequence identity, based on the Clustal V method of alignment, when compared to SEQ ID NO:19, or (b) a complement of the nucleotide sequence, wherein the complement and the nucleotide sequence consist of the same number of nucleotides and are 100% complementary.

An isolated polynucleotide comprising: (a) a nucleotide sequence encoding a polypeptide associated with pollen shed of a plant (preferably maize), wherein said polypeptide has an amino acid sequence of at least 80%, 85%, 90%, 95%, 96%, 97%, 98%, 99% or 100% sequence identity, based on the Clustal V method of alignment, when compared to SEQ ID NO:19, or (b) a complement of the nucleotide sequence, wherein the complement and the nucleotide sequence consist of the same number of nucleotides and are 100% complementary.

An isolated polynucleotide comprising: (a) a nucleic acid sequence encoding a polypeptide having an amino acid sequence of at least 80%, 85%, 90%, 95%, 96%, 97%, 98%, 99% or 100% sequence identity, based on the Clustal V method of alignment, when compared to SEQ ID NO:19, wherein expression of said polypeptide in a plant exhibiting a ramosa3 mutant phenotype results in an decrease of branching of the tassel, ear, or both of the plant; or (b) a complement of the nucleotide sequence, wherein the complement and the nucleotide sequence consist of the same number of nucleotides and are 100% complementary. Preferably, the plant is maize.

An isolated polynucleotide comprising: (a) a nucleic acid sequence encoding a polypeptide having an amino acid sequence of at least 80%, 85%, 90%, 95%, 96%, 97%, 98%, 99% or 100% sequence identity, based on the Clustal V method of alignment, when compared to SEQ ID NO:19, wherein expression of said polypeptide in a plant exhibiting a ramosa3 mutant phenotype results in an decrease of pollen shed of the plant; or (b) a complement of the nucleotide sequence, wherein the complement and the nucleotide sequence consist of the same number of nucleotides and are 100% complementary. Preferably, the plant is maize.

An isolated polynucleotide comprising: (a) a nucleic acid sequence encoding a polypeptide having trehalose-6-phosphate phosphatase activity, wherein the polypeptide has an amino acid sequence of at least 65%, 70%, 75%, 80%, 85%, 90%, 95%, 96%, 97%, 98%, 99% or 100% sequence identity, based on the Clustal V method of alignment, when compared to SEQ ID NO:19, 49, 68 or 69; or (b) a complement of the nucleotide sequence, wherein the complement and the nucleotide sequence consist of the same number of nucleotides and are 100% complementary.

Any recombinant DNA construct comprising a polynucleotide operably linked to a promoter that is functional in said plant, wherein said polynucleotide comprises an isolated polynucleotide of the present invention.

A vector comprising a polynucleotide of the present invention.

A suppression DNA construct comprising a promoter functional in a plant operably linked to (a) all or part of (i) a nucleic acid sequence encoding a polypeptide having an amino acid sequence of at least 50% sequence identity, or any integer up to and including 100% sequence identity, based on the Clustal V method of alignment, when compared to SEQ ID NO:19, 49, 68 or 69, or (ii) a full complement of the nucleic acid sequence of (a)(i); (b) a region derived from all or part of a sense strand or antisense strand of a target gene of interest, said region having a nucleic acid sequence of at least 50% sequence identity, based on the Clustal V method of alignment, when compared to said all or part of a sense strand or antisense strand from which said region is derived, and wherein said target gene of interest encodes a RAMOSA3 (RA3) polypeptide or a SISTER OF RAMOSA3 (SRA) polypeptide; or (c) a nucleic acid sequence of at least 50% sequence identity, or any integer up to and including 100% sequence identity, based on the Clustal V method of alignment, when compared to SEQ ID NO:15, 18, 47, 48, or 67. The suppression DNA construct preferably comprises a cosuppression construct, antisense construct, viral-suppression construct, hairpin suppression construct, stem-loop suppression construct, double-stranded RNA-producing construct, RNAi construct, or small RNA construct (e.g., an siRNA construct or an mRNA construct).

A plant comprising in its genome a recombinant DNA construct of the present invention.

A plant whose genome comprises a disruption (e.g., an insertion, such as a transposable element, or sequence mutation) of at least one gene (which may be heterologous or endogenous to the genome) encoding at least one polypeptide selected from the group consisting of a RAMOSA3 (RA3) polypeptide or a SISTER OF RAMOSA3 (SRA) polypeptide.

Any progeny of the above plants, and any seed obtained from the plant or its progeny. Progeny includes subsequent generations obtained by self-pollination or out-crossing of a plant. Progeny also includes hybrids and inbreds.

A method for altering branching of the tassel, ear, or both, of a plant, comprising: (a) introducing into a regenerable plant cell a recombinant DNA construct to produce a transformed plant cell, said recombinant DNA construct comprising a polynucleotide operably linked to a promoter that is functional in a plant, wherein said polynucleotide encodes a polypeptide having an amino acid sequence of at least 80%, 85%, 90%, 95%, 96%, 97%, 98%, 99% or 100% sequence identity, based on the Clustal V method of alignment, when compared to SEQ ID NO:19; and (b) regenerating a transgenic plant from said transformed plant cell, wherein said transgenic plant comprises in its genome said recombinant DNA construct and wherein said transgenic plant exhibits an alteration in branching of the tassel, ear, or both, when compared to a control plant not comprising said recombinant DNA construct. The method may further comprise (c) obtaining a progeny plant derived from said transgenic plant, wherein said progeny plant comprises in its genome the recombinant DNA construct. Preferably, the transgenic plant or progeny thereof exhibits a decrease in branching of the tassel, ear, or both.

A method for altering pollen shed of a plant, comprising: (a) introducing into a regenerable plant cell a recombinant DNA construct to produce a transformed plant cell, said recombinant DNA construct comprising a polynucleotide operably linked to a promoter that is functional in a plant, wherein said polynucleotide encodes a polypeptide having an amino acid sequence of at least 80%, 85%, 90%, 95%, 96%, 97%, 98%, 99% or 100% sequence identity, based on the Clustal V method of alignment, when compared to SEQ ID NO:19; and (b) regenerating a transgenic plant from said transformed plant cell, wherein said transgenic plant comprises in its genome said recombinant DNA construct and wherein said transgenic plant exhibits an alteration in pollen shed, when compared to a control plant not comprising said recombinant DNA construct. The method may further comprise (c) obtaining a progeny plant derived from said transgenic plant, wherein said progeny plant comprises in its genome the recombinant DNA construct. Preferably, the transgenic plant or progeny thereof exhibits a decrease in pollen shed.

A method for altering trehalose-6-phosphate phosphatase activity in a plant, comprising: (a) introducing into a regenerable plant cell a recombinant DNA construct to produce a transformed plant cell, said recombinant DNA construct comprising a polynucleotide operably linked to a promoter that is functional in a plant, wherein said polynucleotide encodes a polypeptide having an amino acid sequence of at least 65%, 70%, 75%, 80%, 85%, 90%, 95%, 96%, 97%, 98%, 99% or 100% sequence identity, based on the Clustal V method of alignment, when compared to SEQ ID NO:19, 49, 68 or 69; and (b) regenerating a transgenic plant from said transformed plant cell, wherein said transgenic plant comprises in its genome said recombinant DNA construct and wherein said transgenic plant exhibits an alteration in trehalose-6-phosphate phosphatase activity, when compared to a control plant not comprising said recombinant DNA construct. The method may further comprise (c) obtaining a progeny plant derived from said transgenic plant, wherein said progeny plant comprises in its genome the recombinant DNA construct. Preferably, the transgenic plant or progeny thereof exhibits an increase in trehalose-6-phosphate phosphatase activity.

A method for increasing environmental stress tolerance (preferably drought tolerance) of a plant, comprising: (a) introducing into a regenerable plant cell a recombinant DNA construct to produce a transformed plant cell, said recombinant DNA construct comprising a polynucleotide operably linked to a promoter that is functional in a plant, wherein said polynucleotide encodes a polypeptide having an amino acid sequence of at least 65%, 70%, 75%, 80%, 85%, 90%, 95%, 96%, 97%, 98%, 99% or 100% sequence identity, based on the Clustal V method of alignment, when compared to SEQ ID NO:19, 49, 68 or 69; and (b) regenerating a transgenic plant from said transformed plant cell, wherein said transgenic plant comprises in its genome said recombinant DNA construct and wherein said transgenic plant exhibits an increase in environmental stress tolerance (preferably drought tolerance), when compared to a control plant not comprising said recombinant DNA construct. The method may further comprise (c) obtaining a progeny plant derived from said transgenic plant, wherein said progeny plant comprises in its genome the recombinant DNA construct.

BRIEF DESCRIPTION OF THE FIGURES AND SEQUENCE LISTING

The invention can be more fully understood from the following detailed description and the accompanying drawings and Sequence Listing which form a part of this application.

FIG. 1 shows the mature ear and tassel phenotypes of ra3 mutants.

Figure 2:
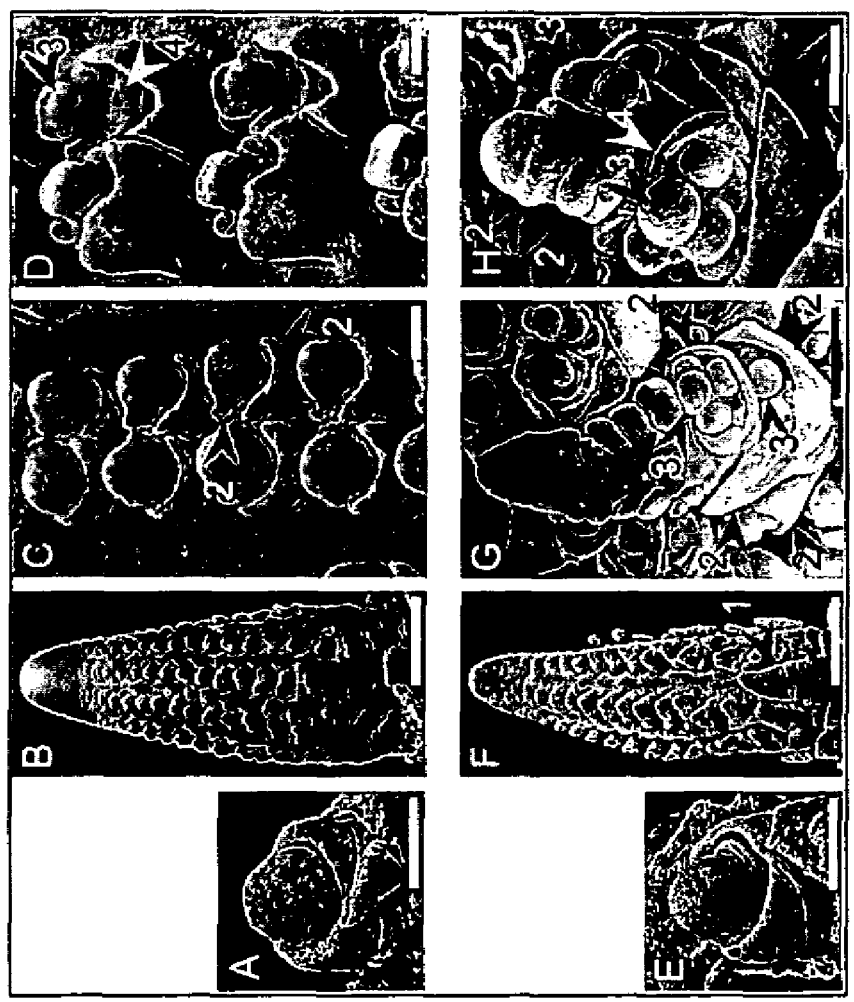

FIG. 2 shows the SEM analysis of ra3 mutant ears. Wild type (B73) ears are shown in A-D, and ra3 ears in E-H. During the inflorescence transition stage, there is no difference between B73 (A) and ra3 mutant (E) ears. In 2 mm long ears, some SPM converted to BM* (F, arrow 1). SMs in B73 produce a pair of glumes (C, arrows 2), but in ra3 they produce additional glumes (G, arrows 2), and FMs were made inside the glumes (arrow 3). The SMs in wild type ears make 2 FMs inside the glumes (D, upper FM marked by arrow 3) and each floret has a lemma and palea (D, palea marked by arrow 4). The SMs in ra3 mutants make several FMs (arrows 3, H, palea marked by arrow 4) and later can convert to a BM* that makes glumes (H, arrows 2). Scale bars A, E 100 µm; B, F 500 µm; C, D 100 µm; G, H 200 µm.

Figure 3:
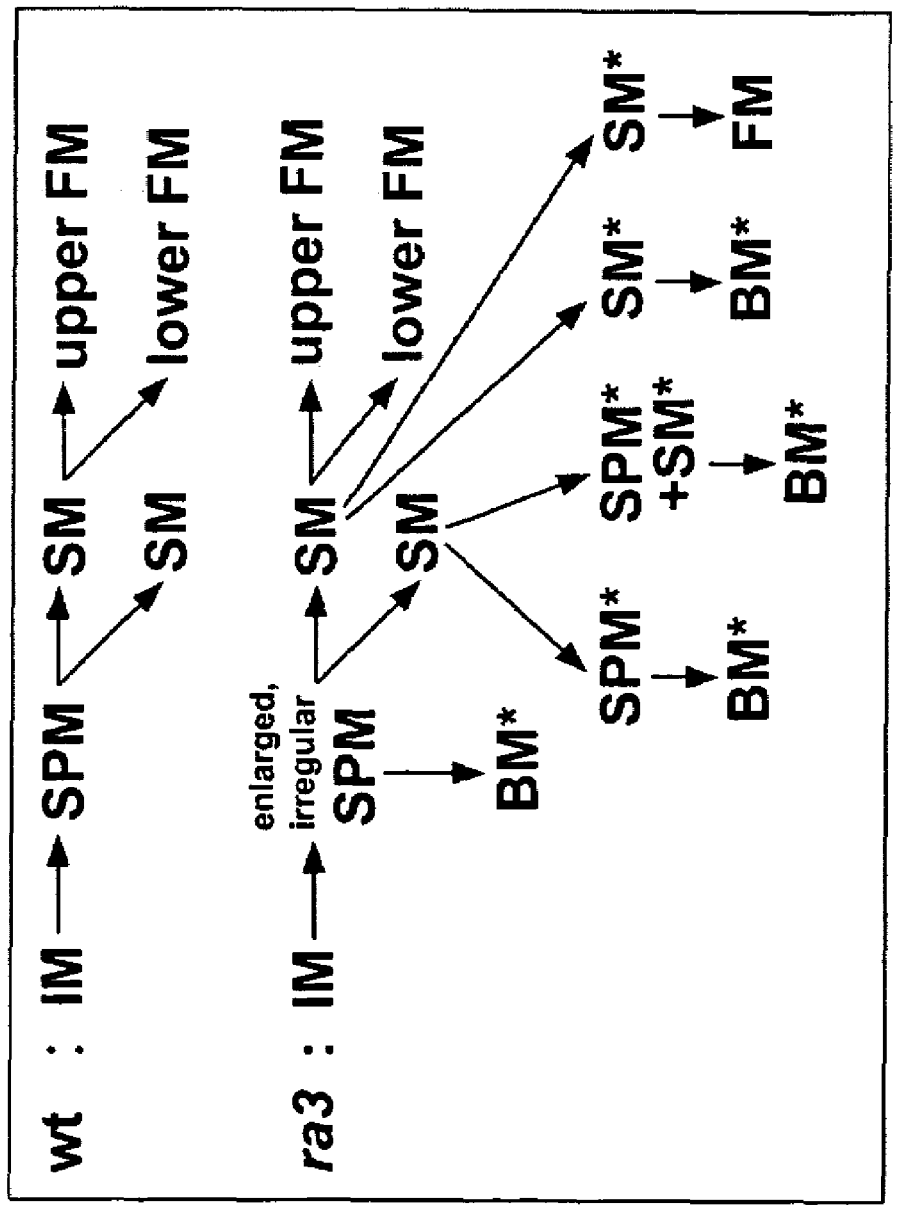

FIG. 3 shows a schematic of wild type (wt) and ra3 ear development. BM* indicates a meristem which makes SPMs. SPM* indicates a meristem which makes SMs. SM* indicates meristem which makes FMs.

Figure 4:
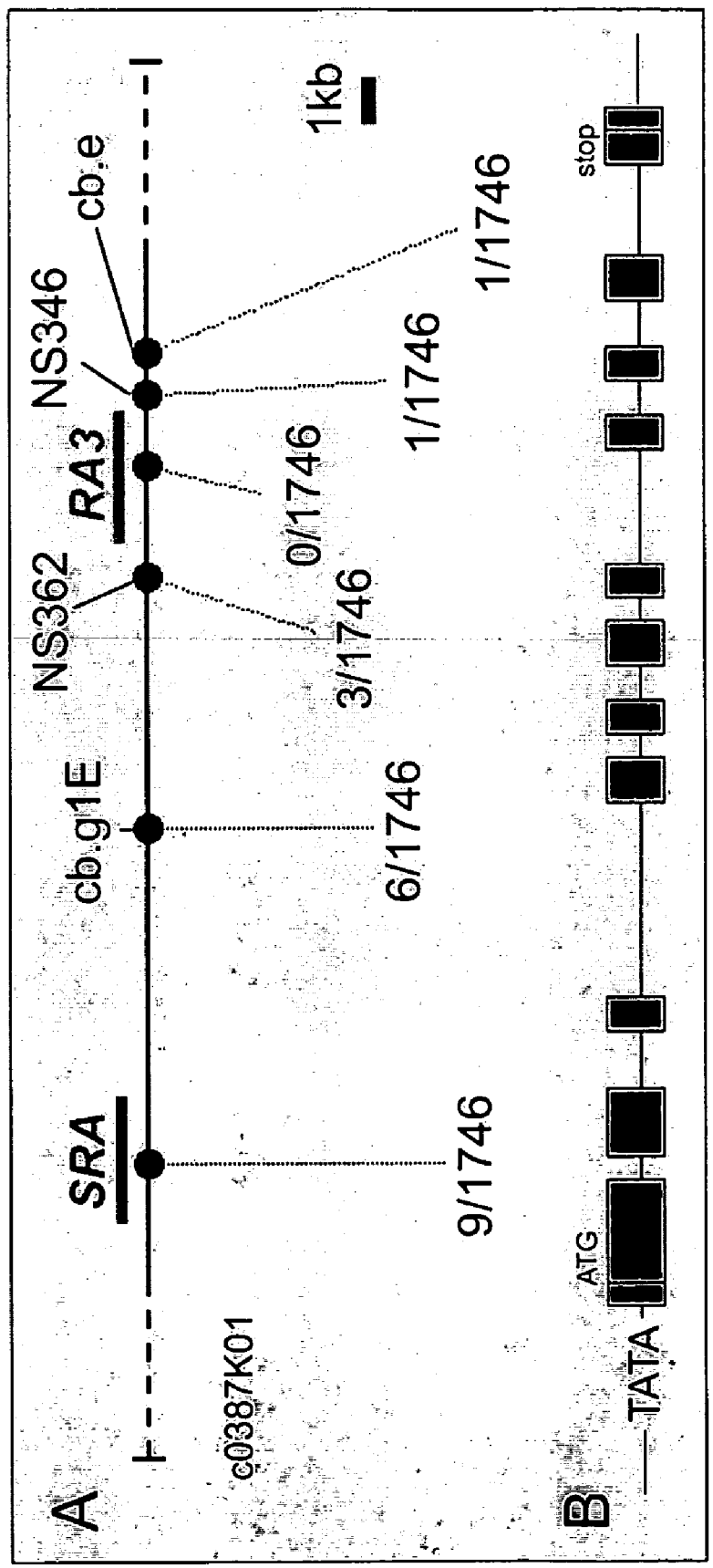

FIG. 4 shows a map of the RA3 locus. The position of the RA3 and related SRA loci on BAC clone c0387K01 is given in (A). Marker positions are shown as black dots and number of recombinants for each is shown. The RA3 gene structure is given in (B). The shaded box immediately preceding the start ATG codon and the shaded box immediately following the stop codon each represent UTRs; the shaded boxes in between these UTRs indicate coding sequence; and "TATA" indicates the predicted TATA-box.

Figure 5:
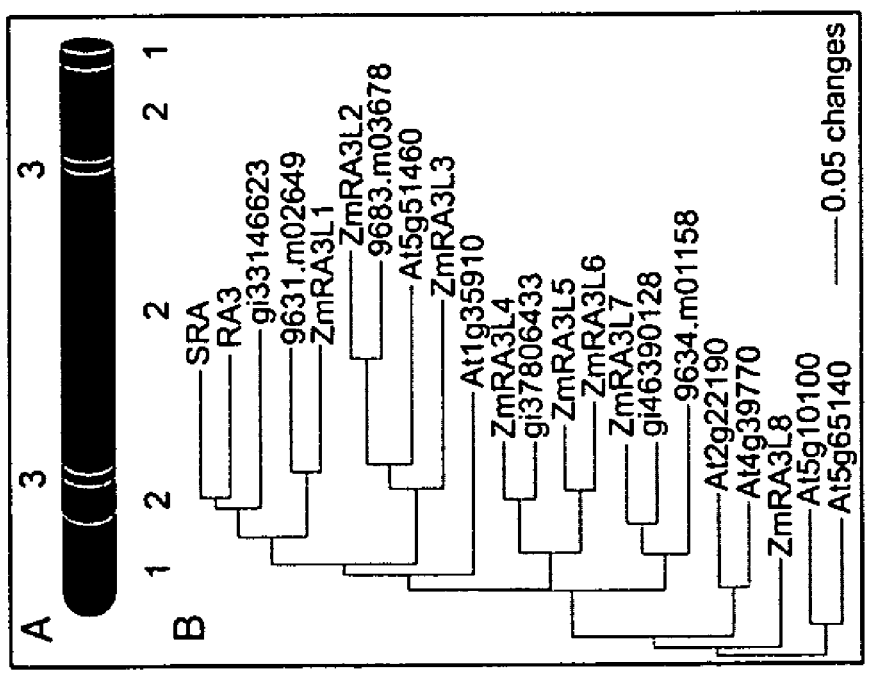

FIG. 5 shows the predicted RA3 protein structure and phylogenetic analysis. The RA3 protein structure is shown in part A. The TPP similarity regions are labeled "2", the phosphatase boxes are labeled "3", and the non-conserved regions are labeled "1". The neighbor joining tree is shown in part B. using Phylogenetic Analysis Using Parsimony ("PAUP"; SWOFFORD D. L., (1993) *J Gen Physiol* 102: A9) of the conserved part of the TPP region of RA3-like proteins in maize, rice and *Arabidopsis*. Maize proteins are the following: RA3, SRA, ZmRA3L1-8. Rice proteins are the following: gi46390128, gi37806433, gi33146623, 9631.m02649, 9683.m03678, 9634.m01158. *Arabidopsis* proteins are the following: At5g51460, At1g35910, At2g22190, At4g39770, At5g10100, At5g65140.

FIGS. 6A, 6B, 6C and 6D show a sequence alignment of the following amino acid sequences: (1) SEQ ID NO:19, for the corn RAMOSA3 polypeptide; (2) SEQ ID NO:49, for the corn SISTER OF RAMOSA3 polypeptide; (3) SEQ ID NO:51, for the rice trehalose-6-phosphate phosphatase polypeptide corresponding to NCBI GI NO. 33146623; (4) SEQ ID NO:52, for the *Arabidopsis* TPPA polypeptide corresponding to NCBI GI NO. 2944178; (5) SEQ ID NO:53, for the *Arabidopsis* TPPB polypeptide corresponding to NCBI GI NO. 2944180; (6) SEQ ID NO:54, for a corn trehalose-6-phosphate phosphatase polypeptide that is cited as SEQ ID NO:16 in U.S. Patent Publication 2004-0229364-A1; (7) SEQ ID NO:55, for a soybean trehalose-6-phosphate phosphatase polypeptide that is cited as SEQ ID NO:20 in U.S. Patent Publication 2004-0229364-A1; (8) a truncated version of SEQ ID NO:52, in which the N-terminal 91 amino acids are removed; this fragment was shown to have enzymatic activity (Vogel et al. (1998) *Plant J* 13(5):673-683); and (9) a truncated version of SEQ ID NO:53, in which the N-terminal 91 amino acids have been removed. A consensus sequence of 414 amino acids was generated and is numbered below these nine sequences. The amino acid positions for each sequence is given to the left of each row, and to the right of the final row. An asterisk above an amino acid residue indicates that the position is totally conserved among the given SEQ ID NOS, with respect to the *Arabidopsis thaliana* AtTPPB sequence. Below the sequences are shown two domains, A and B, that are conserved among trehalose-6-phosphate phosphatases, as described in Vogel et al. (1998) *Plant J* 13(5):673-683. The given sequence for each conserved domain is taken from the *Arabidopsis thaliana* AtTPPB amino acid sequence at these positions.

Figure 7:
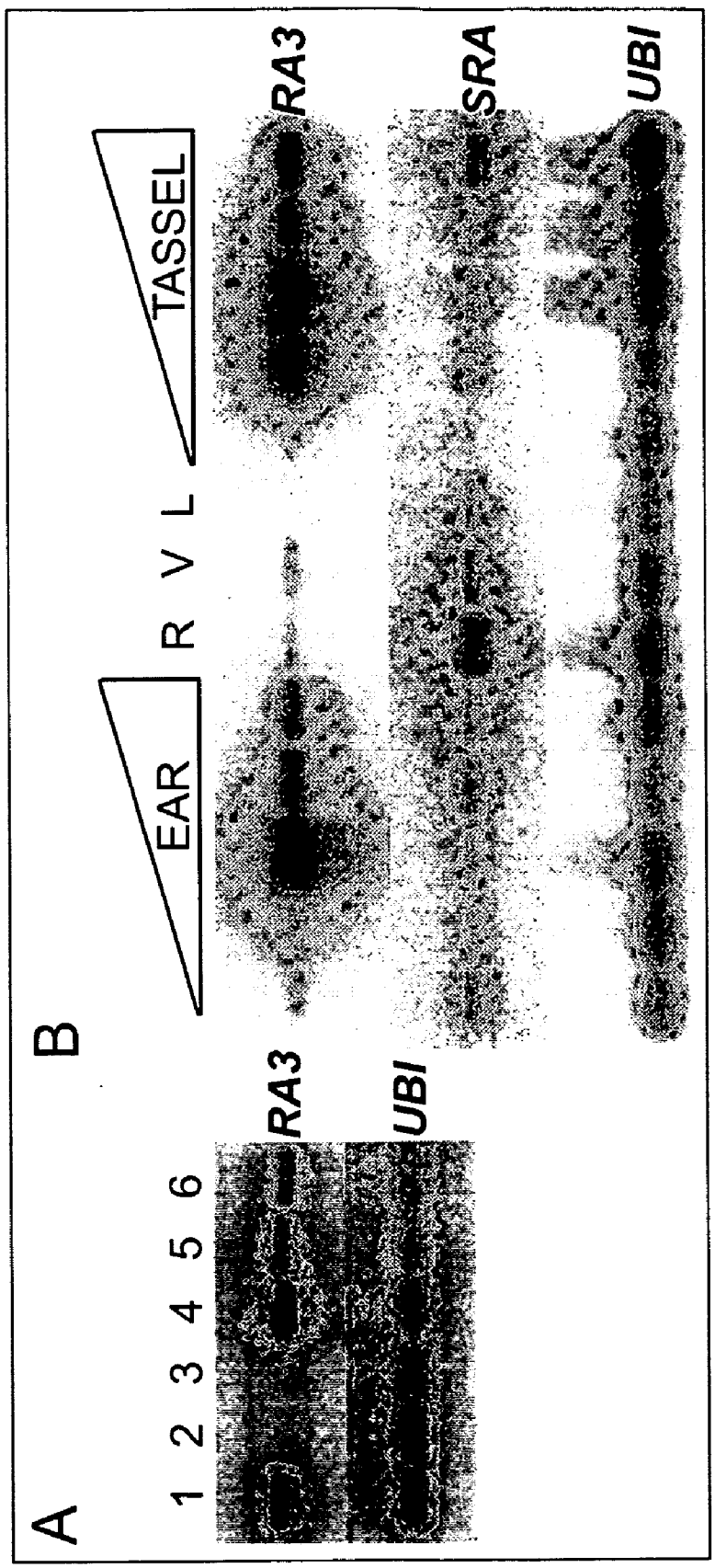

FIG. 7 shows that RA3 expression is highest in developing inflorescences. In part (A) is shown the RA3 expression in 1 cm ear primordia from B73 (lane 1) and ra3 alleles. In ra3-ref (lane 2) and ra3-fea1 (lane 3), very low expression was detected, while the level of expression in ra3-EV, ra3-NI and ra3-bre (lanes 4-6) was normal, except that the ra3-NI transcript is slightly larger, as it has a small insertion (Table 2). The lower panel shows Ubiquitin (UBI) expression as a control. In part (B) is shown the RA3, SRA and Ubiquitin expression during wild type (B73) development. The mRNAs were extracted from root (R), vegetative apex (V), young leaves (L) and ear or tassel inflorescence primordia. The triangles represent increasing inflorescence size, from transition stage to ~1.5 cm ears and tassels. RA3 expression peaks in 2-5 mm inflorescences.

Figure 8:
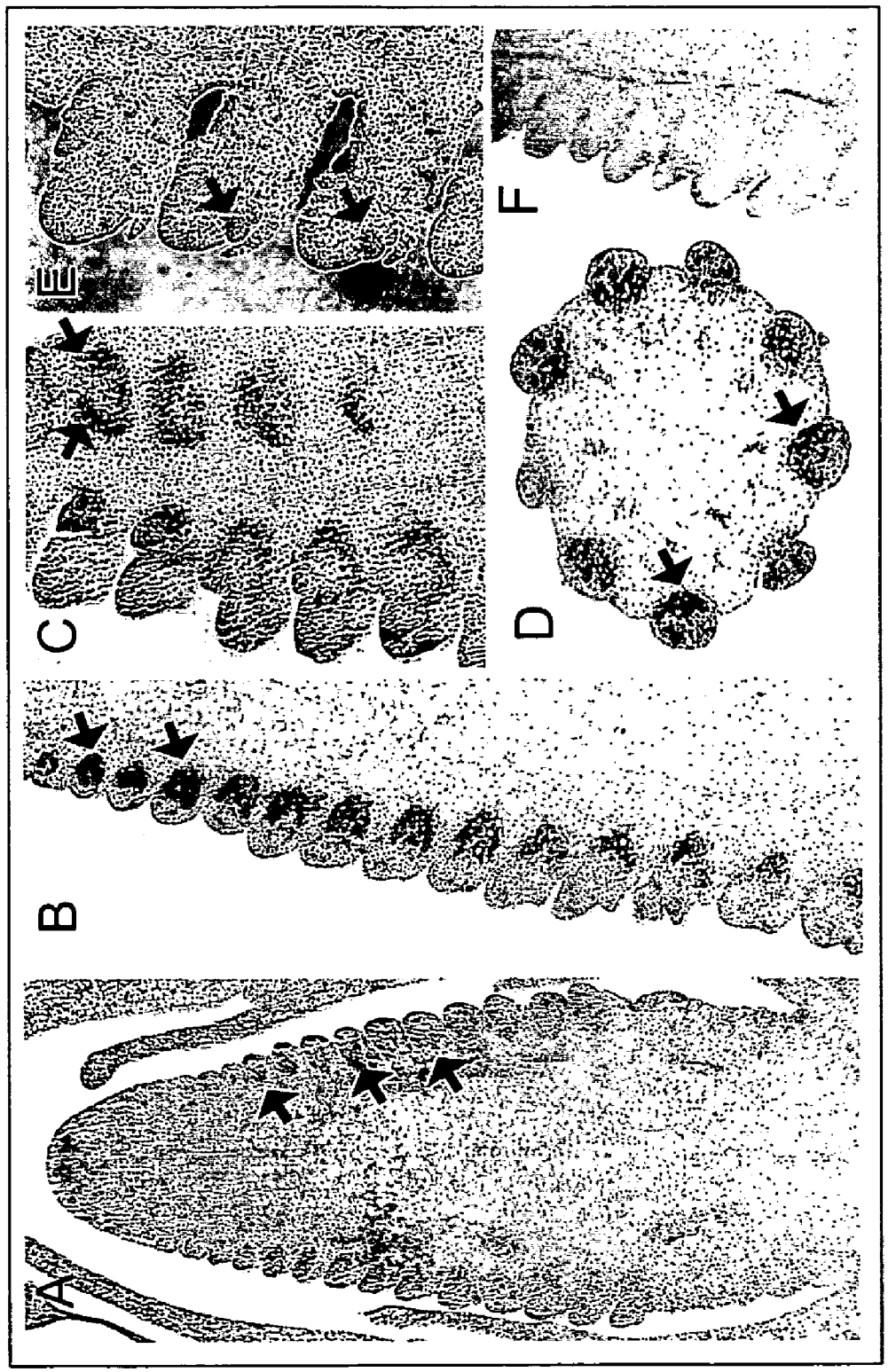

FIG. 8 shows that RA3 expression is spatially restricted during ear development. RA3 was first expressed at the base of SPMs (arrows, A). After that, RA3 expression enlarged to a cup-shaped domain at the base of SPMs and SMs (arrows, B, C and D). Parts (B) and (C) are longitudinal median and glancing sections, respectively, and (D) is a transverse section. At later stages, RA3 was expressed at the boundary between upper and lower florets (arrows, E). No RA3 transcript was detected in a ra3-ref ear (F), at similar stage to (B).

Figure 9:
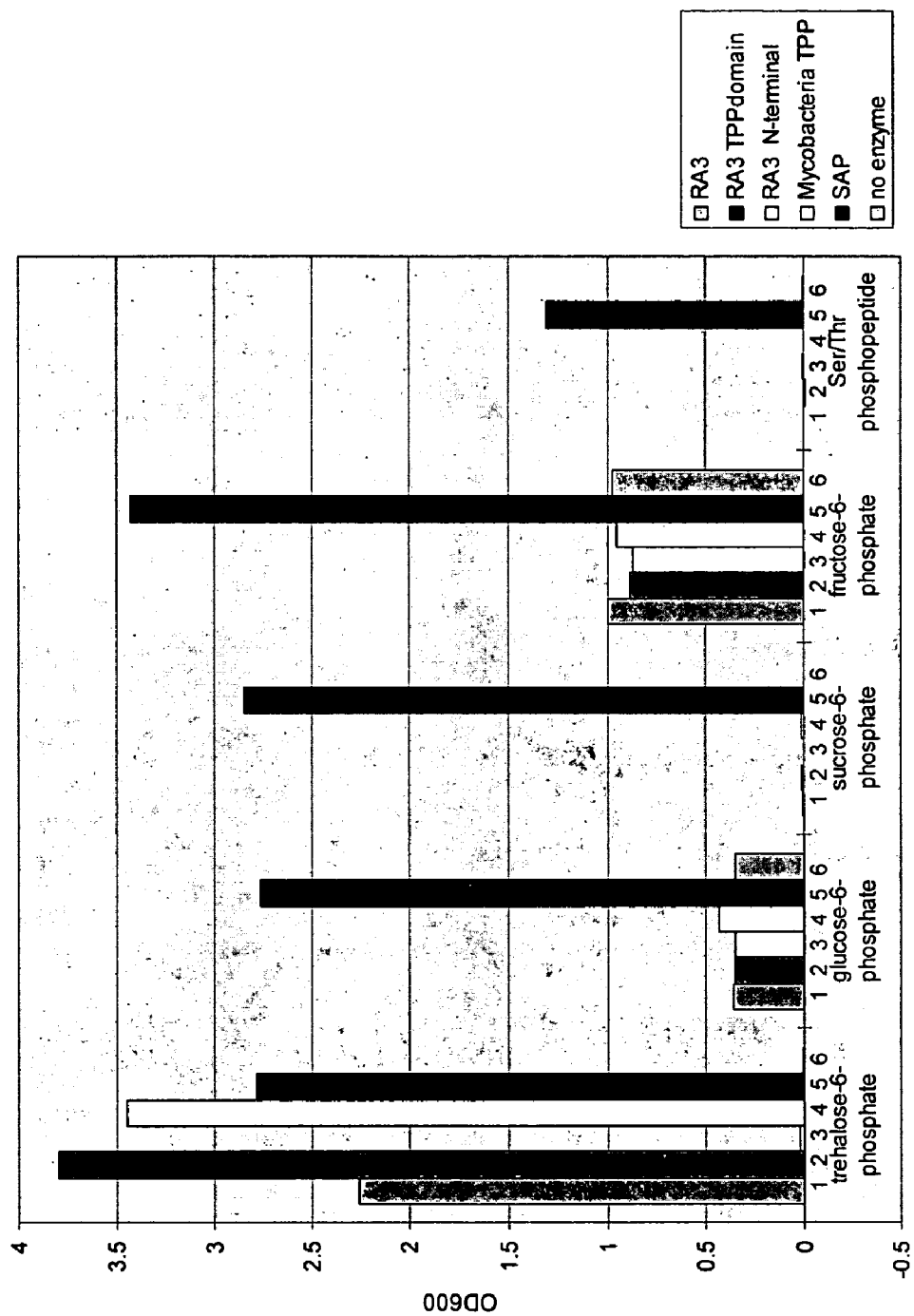

FIG. 9 shows phosphate release, measured as $OD_{600}$, following treatment of various phosphorylated substrates. For each substrate, shown left to right, respectively, is the activity due to each of the following proteins: 1) His-tagged RA3 full-length protein (SEQ ID NO:61); 2) His-tagged RA3 TPP-domain fragment (SEQ ID NO:62); 3) His-tagged RA3 N-terminal fragment (SEQ ID NO:63); 4) His-tagged *Mycobacterium tuberculosis* TPP (Edavana et al., *Arch Biochem Biophys* 426:250-257 (2004)); 5) shrimp alkaline phosphatase (SAP; Roche Applied Science); 6) no protein.

Figure 10:
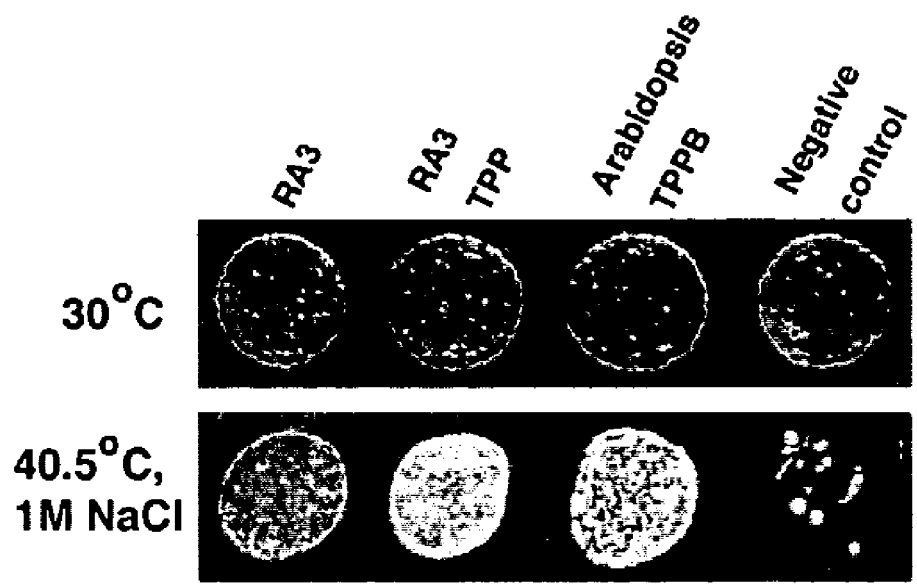

FIG. 10 shows growth of a yeast tps2 mutant (yeast strain YSH6.106.-8C) transformed with an RA3 protein, RA3 TPP-domain fragment, a positive control (*Arabidopsis* trehalose-6-phosphate phosphatase gene, AtTPPB), and a negative control (empty yeast vector). Transformed cells were assayed for growth on selective media at 40.5° C. in the presence of 1 M NaCl, as well as at 30° C.

SEQ ID NO:1 is the nucleotide sequence of the csu597 forward primer.

SEQ ID NO:2 is the nucleotide sequence of the csu597 reverse primer.

SEQ ID NO:3 is the nucleotide sequence of the umc1412 forward primer.

SEQ ID NO:4 is the nucleotide sequence of the umc1412 reverse primer.

SEQ ID NO:5 is the nucleotide sequence of the a14 forward primer.

SEQ ID NO:6 is the nucleotide sequence of the a14 reverse primer.

SEQ ID NO:7 is the nucleotide sequence of the n20 forward primer.

SEQ ID NO:8 is the nucleotide sequence of the n20 reverse primer.

SEQ ID NO:9 is the nucleotide sequence of the cb.g1E forward primer.

SEQ ID NO:10 is the nucleotide sequence of the cb.g1E reverse primer.

SEQ ID NO:11 is the nucleotide sequence of the NS346 primer.

SEQ ID NO:12 is the nucleotide sequence of the NS347 primer.

SEQ ID NO:13 is the nucleotide sequence of the NS362 primer.

SEQ ID NO:14 is the nucleotide sequence of the NS363 primer.

SEQ ID NO:15 is the genomic nucleotide sequence containing the RAMOSA3 gene.

SEQ ID NO:16 is the nucleotide sequence of the NS432 forward primer used to amplify the cDNA containing the RAMOSA3 open-reading frame.

SEQ ID NO:17 is the nucleotide sequence of the NS411 reverse primer used to amplify the cDNA containing the RAMOSA3 open-reading frame.

SEQ ID NO:18 is the nucleotide sequence of the protein-coding region deduced from the PCR product obtained using the primers of SEQ ID NOS:16 & 17 to amplify maize cDNA.

SEQ ID NO:19 is the amino acid sequence of the RAMOSA3 polypeptide.

SEQ ID NO:20 is the nucleotide sequence of the 5' UTR-exon2 forward primer.

SEQ ID NO:21 is the nucleotide sequence of the 5' UTR-exon2 reverse primer.

SEQ ID NO:22 is the nucleotide sequence of the exon3-exon4 forward primer.

SEQ ID NO:23 is the nucleotide sequence of the exon3-exon4 reverse primer.

SEQ ID NO:24 is the nucleotide sequence of the exon5-exon7 forward primer.

SEQ ID NO:25 is the nucleotide sequence of the exon5-exon7 reverse primer.

SEQ ID NO:26 is the nucleotide sequence of the exon8-exon10 forward primer.

SEQ ID NO:27 is the nucleotide sequence of the exon8-exon10 reverse primer.

SEQ ID NO:28 is the nucleotide sequence of the exon11-3' UTR forward primer.

SEQ ID NO:29 is the nucleotide sequence of the exon11-3' UTR reverse primer.

SEQ ID NO:30 is the nucleotide sequence of a region in exon7 of the ra3-ref mutant gene, that contains a 4 base pair insertion relative to the sequence of SEQ ID NO:15.

SEQ ID NO:31 is the deduced amino acid sequence of the mutant ra3-ref RAMOSA3 polypeptide, which has a frameshift after amino acid 249, relative to SEQ ID NO:19, and a premature stop codon after 305 amino acids.

SEQ ID NO:32 is the nucleotide sequence of an ILS-1-like transposon element present in the 5'-UTR region of the ra3-fea1 mutant gene.

SEQ ID NO:33 is the nucleotide sequence of a region of exon7 in the ra3-fea1 mutant gene, that contains a 4 base pair insertion relative to the sequence of SEQ ID NO:15.

SEQ ID NO:34 is the deduced amino acid sequence of the mutant ra3-fea1 RAMOSA3 polypeptide, which has a frame-shift after amino acid 258 relative to SEQ ID NO:19, and a premature stop codon after 305 amino acids.

SEQ ID NO:35 is the nucleotide sequence of a region of exon6 of the ra3-EV mutant gene, that contains a 4 base pair insertion relative to SEQ ID NO:15.

SEQ ID NO:36 is the deduced amino acid sequence of the mutant ra3-EV RAMOSA3 polypeptide, which has a frame-shift after amino acid 224 relative to SEQ ID NO:19, and a premature stop codon after 305 amino acids.

SEQ ID NO:37 is the nucleotide sequence of a region of exon10 of the ra3-NI mutant gene, that contains a 141 base pair insertion relative to SEQ ID NO:15.

SEQ ID NO:38 is the deduced amino acid sequence of the mutant ra3-NI RAMOSA3 polypeptide, which has a different amino acid sequence after amino acid 333 relative to SEQ ID NO:19, and a premature stop codon after 335 amino acids.

SEQ ID NO:39 is the nucleotide sequence of a region between exon6 and exon7 of the ra3-bre mutant gene, that contains a 10 base pair insertion relative to SEQ ID NO:15.

SEQ ID NO:40 is the deduced amino acid sequence of the mutant ra3-bre RAMOSA3 polypeptide, which has a frame-shift after amino acid 241 and a premature stop codon after 243 amino acids.

SEQ ID NO:41 is the nucleotide sequence of region of exon6 of the ra3-JL mutant gene, that contains a deletion and rearrangement relative to SEQ ID NO:15.

SEQ ID NO:42: is the deduced amino acid sequence of the mutant ra3-JL RAMOSA3 polypeptide, which has a different protein sequence after amino acid 217 and a premature stop codon after 246 amino acids.

SEQ ID NO:43 is the nucleotide sequence of a region of exon6 of the ra3-NS mutant gene, that contains a 2 base pair insertion relative to SEQ ID NO:15.

SEQ ID NO:44 is the deduced amino acid sequence of the mutant ra3-NS RAMOSA3 polypeptide, which has a frame-shift after amino acid 222 and a premature stop codon after 299 amino acids.

SEQ ID NO:45 is the amino acid sequence of the conserved "A-domain" phosphatase box, as described in Vogel et al. (*Plant J.* 13:673-683 (1998)) and in U.S. Patent Publication 2004-0229364-A1, the entire contents of which are herein incorporated by reference.

SEQ ID NO:46 is the amino acid sequence of the conserved "B-domain" phosphatase box, as described in Vogel et al. (*Plant J.* 13:673-683 (1998)) and in U.S. Patent Publication 2004-0229364-A1.

SEQ ID NO:47 is the genomic nucleotide sequence containing the SISTER OF RAMOSA3 (SRA) gene.

SEQ ID NO:48 is the nucleotide sequence of the protein-coding region of the SRA gene.

SEQ ID NO:49 is the amino acid sequence of the SRA polypeptide.

SEQ ID NO:50 is a nucleotide sequence contained in the clone my.cs1.pk0072.d4, which is a cDNA clone containing a fragment of the SRA gene.

SEQ ID NO:51 is the amino acid sequence of the rice trehalose-6-phosphate phosphatase polypeptide corresponding to NCBI GI NO. 33146623.

SEQ ID NO:52 is the amino acid sequence for the *Arabidopsis* AtTPPA polypeptide corresponding to NCBI GI NO. 2944178.

SEQ ID NO:53 is the amino acid sequence for the *Arabidopsis* AtTPPB polypeptide corresponding to NCBI GI NO. 2944180.

SEQ ID NO:54 is the amino acid sequence for a corn trehalose-6-phosphate phosphatase polypeptide that is cited as SEQ ID NO:16 in U.S. Patent Publication 2004-0229364-A1, the entire contents of which are herein incorporated by reference.

SEQ ID NO:55 is the amino acid sequence for a soybean trehalose-6-phosphate phosphatase polypeptide that is cited as SEQ ID NO:20 in U.S. Patent Publication 2004-0229364-A1.

SEQ ID NO:56 is the nucleotide sequence of the NS487 primer.

SEQ ID NO:57 is the nucleotide sequence of the NS429 primer.

SEQ ID NO:58 is the nucleotide sequence of the NS483 primer.

SEQ ID NO:59 is the nucleotide sequence of the NS485 primer.

SEQ ID NO:60 is the nucleotide sequence of the NS488 primer.

SEQ ID NO:61 is the amino acid sequence of the His-tagged RA3 protein produced in *E. coli*. SEQ ID NO:61 consists of a 37-aa N-terminal region that contains six consecutive histidine residues, followed by the 361-aa residues of the RA3 protein (SEQ ID NO:19).

SEQ ID NO:62 is the amino acid sequence of the His-tagged RA3 TPP-domain fragment produced in *E. coli*. SEQ ID NO:62 consists of a 35-aa N-terminal region that contains six consecutive histidine residues, followed by amino acid residues 78-361 of the RA3 protein (SEQ ID NO:19).

SEQ ID NO:63 is the amino acid sequence of the His-tagged RA3 N-terminal fragment produced in *E. coli*. SEQ ID NO:63 consists of a 34-aa N-terminal region that contains six consecutive histidine residues, followed by amino acid residues 1-78 of the RA3 protein (SEQ ID NO:19).

SEQ ID NO:64 is the nucleotide sequence of the NS489 primer.

SEQ ID NO:65 is the nucleotide sequence of the NS490 primer.

SEQ ID NO:66 is the nucleotide sequence of the NS500 primer.

SEQ ID NO:67 is the nucleotide sequence of the DNA fragment encoding a RA3 TPP-domain fragment, that was shown to rescue growth of the yeast tps2 mutant at the non-permissive temperature. SEQ ID NO:67 consists of an ATG start codon followed by nucleotides 235-1086 of SEQ ID NO:18.

SEQ ID NO:68 is the amino acid sequence of the RA3 TPP-domain fragment encoded by SEQ ID NO:67. SEQ ID NO:68 consists of a start methionine residue followed by amino acid residues 79-361 of SEQ ID NO:19.

SEQ ID NO:69 is the amino acid sequence of the SRA TPP-domain fragment, and corresponds to amino acids 76-370 of SEQ ID NO:49.

SEQ ID NO:70 corresponds to amino acids 92-385 of SEQ ID NO:52 (*Arabidopsis* AtTPPA); this polypeptide fragment has been shown to have enzymatic activity (Vogel et al. (1998) *Plant J* 13(5):673-683).

SEQ ID NO:71 corresponds to amino acids 92-374 of SEQ ID NO:53 (*Arabidopsis* AtTPPB).

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219(2):345-373 (1984) which are herein incorporated by reference. The symbols and format used for nucleotide and amino acid sequence data comply with the rules set forth in 37 C.F.R. §1.822. The sequence descriptions and Sequence Listing attached hereto comply with the rules governing nucleotide and/or amino acid sequence disclosures in patent applications as set forth in 37 C.F.R. §1.821-1.825.

DETAILED DESCRIPTION OF THE INVENTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

The term "RAMOSA3 (RA3) gene" is a gene of the present invention and refers to a non-heterologous form of a full-length RAMOSA3 (RA3) polynucleotide. In a preferred embodiment, the RAMOSA3 gene comprises SEQ ID NO:15 or 18.

"RAMOSA3 (RA3) polypeptide" refers to a polypeptide of the present invention and may comprise one or more amino acid sequences, in glycosylated or non-glycosylated form. In a preferred embodiment, the RAMOSA3 (RA3) polypeptide comprises SEQ ID NO:19. A "RAMOSA3 (RA3) protein" comprises a RAMOSA3 (RA3) polypeptide.

"SISTER OF RAMOSA3 (SRA) gene" is a gene of the present invention and refers to a non-heterologous form of a full-length SISTER OF RAMOSA3 (SRA) polynucleotide. In a preferred embodiment, the SISTER OF RAMOSA3 (SRA) gene comprises SEQ ID NO:47 or 48.

"SISTER OF RAMOSA3 (SRA) polypeptide" refers to a polypeptide of the present invention and may comprise one or more amino acid sequences, in glycosylated or non-glycosylated form. In a preferred embodiment, the SISTER OF RAMOSA3 (SRA) polypeptide comprises SEQ ID NO:49. A "SISTER OF RAMOSA3 (SRA) protein" comprises a SISTER OF RAMOSA3 (SRA) polypeptide.

"Transgenic" includes any cell, cell line, callus, tissue, plant part or plant, the genome of which has been altered by the presence of a heterologous nucleic acid, such as a recombinant DNA construct, including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. Preferably, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably and is a polymer of RNA or DNA that is single or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from a mRNA template using the enzyme reverse transcriptase. The cDNA can be single-stranded or converted into the double-stranded form using the Klenow fragment of DNA polymerase 1.

"Mature" protein refers to a post-translationally processed polypeptide; i.e., one from which any pre- or pro-peptides present in the primary translation product have been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

"Allele" is one of several alternative forms of a gene occupying a given locus on a chromosome. Different alleles of a gene differ in their DNA sequence. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

"Contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well-established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

The term "amplified" means the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Diagnostic Molecular Microbiology: Principles and Applications, D. H. Persing et al., Ed., American Society for Microbiology, Washington, D.C. (1993). The product of amplification is termed an amplicon.

The term "chromosomal location" includes reference to a length of a chromosome which may be measured by reference to the linear segment of DNA which it comprises. The chromosomal location can be defined by reference to two unique DNA sequences, i.e., markers.

The term "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes in that pair to be followed. A genotype may be defined by use of one or a plurality of markers.

Sequence alignments and percent identity calculations may be determined using a variety of comparison methods designed to detect homologous sequences including, but not limited to, the Megalign program of the LASARGENE bioinformatics computing suite (DNASTAR Inc., Madison, Wis.). Unless stated otherwise, multiple alignment of the sequences provided herein were performed using the Clustal V method of alignment (Higgins and Sharp (1989) CABIOS. 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Unless otherwise stated, "BLAST" sequence identity/similarity values provided herein refer to the value obtained using the BLAST 2.0 suite of programs using default parameters (Altschul et al., *Nucleic Acids Res.* 25:3389-3402 (1997)). Software for performing BLAST analyses is publicly available, e.g., through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci.* USA 89:10915 (1989)).

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

Turning now to preferred embodiments:

The present invention includes isolated polynucleotides.

In one preferred embodiment, an isolated polynucleotide comprises: (a) a nucleic acid sequence encoding a polypeptide having an amino acid sequence of at least 80%, 85%, 90%, 95%, 96%, 97%, 98%, 99% or 100% sequence identity, based on the Clustal V method of alignment, when compared to SEQ ID NO:19, wherein expression of said polypeptide in a plant transformed with said isolated polynucleotide results in alteration of the branching of the tassel, ear, or both, of said transformed plant when compared to a control plant not comprising said isolated polynucleotide; or (b) a complement of the nucleotide sequence, wherein the complement and the nucleotide sequence consist of the same number of nucleotides and are 100% complementary. Preferably, expression of said polypeptide results in a decrease in the branching of the tassel, ear, or both, and even more preferably, the plant is maize.

In another preferred embodiment, an isolated polynucleotide comprises: (a) a nucleic acid sequence encoding a polypeptide having an amino acid sequence of at least 80%, 85%, 90%, 95%, 96%, 97%, 98%, 99% or 100% sequence identity, based on the Clustal V method of alignment, when compared to SEQ ID NO:19, wherein expression of said polypeptide in a plant transformed with said isolated polynucleotide results in alteration of pollen shed of said transformed plant when compared to a control plant not comprising said isolated polynucleotide; or (b) a complement of the nucleotide sequence, wherein the complement and the nucleotide sequence consist of the same number of nucleotides and are 100% complementary. Preferably, expression of said polypeptide results in a decrease in pollen shed, and even more preferably, the plant is maize.

In another preferred embodiment, an isolated polynucleotide comprises: (a) a nucleotide sequence encoding a polypeptide associated with branching of the tassel, ear, or both, of a plant (preferably maize), wherein said polypeptide has an amino acid sequence of at least 80%, 85%, 90%, 95%, 96%, 97%, 98%, 99% or 100% sequence identity, based on the Clustal V method of alignment, when compared to SEQ ID NO:19, or (b) a complement of the nucleotide sequence, wherein the complement and the nucleotide sequence consist of the same number of nucleotides and are 100% complementary.

In another preferred embodiment, an isolated polynucleotide comprises: (a) a nucleotide sequence encoding a polypeptide associated with pollen shed of a plant (preferably maize), wherein said polypeptide has an amino acid sequence of at least 80%, 85%, 90%, 95%, 96%, 97%, 98%, 99% or 100% sequence identity, based on the Clustal V method of alignment, when compared to SEQ ID NO:19, or (b) a complement of the nucleotide sequence, wherein the complement and the nucleotide sequence consist of the same number of nucleotides and are 100% complementary.

A polypeptide is "associated with branching" or "associated with pollen shed" in that the absence of the polypeptide in a plant results in an increase in branching or pollen shed of the plant when compared to a plant that expresses the polypeptide.

In another preferred embodiment, an isolated polynucleotide comprises: (a) a nucleic acid sequence encoding a polypeptide having an amino acid sequence of at least 80%, 85%, 90%, 95%, 96%, 97%, 98%, 99% or 100% sequence identity, based on the Clustal V method of alignment, when compared to SEQ ID NO:19, wherein expression of said polypeptide in a plant exhibiting a ramosa3 mutant phenotype results in an decrease of branching of the tassel, ear, or both of the plant; or (b) a complement of the nucleotide sequence, wherein the complement and the nucleotide sequence consist of the same number of nucleotides and are 100% complementary. Preferably, the plant is maize.

In another preferred embodiment, an isolated polynucleotide comprises: (a) a nucleic acid sequence encoding a polypeptide having an amino acid sequence of at least 80%, 85%, 90%, 95%, 96%, 97%, 98%, 99% or 100% sequence identity, based on the Clustal V method of alignment, when compared to SEQ ID NO:19, wherein expression of said polypeptide in a plant exhibiting a ramosa3 mutant phenotype results in an decrease of pollen shed of the plant; or (b) a complement of the nucleotide sequence, wherein the complement and the nucleotide sequence consist of the same number of nucleotides and are 100% complementary. Preferably, the plant is maize.

In another preferred embodiment, an isolated polynucleotide comprises: (a) a nucleic acid sequence encoding a polypeptide having trehalose-6-phosphate phosphatase activity, wherein the polypeptide has an amino acid sequence of at least 65%, 70%, 75%, 80%, 85%, 90%, 95%, 96%, 97%, 98%, 99% or 100% sequence identity, based on the Clustal V method of alignment, when compared to SEQ ID NO:19, 49, 68 or 69; or (b) a complement of the nucleotide sequence, wherein the complement and the nucleotide sequence consist of the same number of nucleotides and are 100% complementary. Preferably, when compared to SEQ ID NO:68 or 69, the polypeptide has an amino acid sequence of at least 70%, 75%, 80%, 85%, 90%, 95%, 96%, 97%, 98%, 99% or 100% sequence identity, based on the Clustal V method of alignment.

The present invention also includes isolated polypeptides.

In a preferred embodiment, an isolated polypeptide comprises an amino acid sequence of at least 80%, 85%, 90%, 95%, 96%, 97%, 98%, 99% or 100% sequence identity, based on the Clustal V method of alignment, when compared to SEQ ID NO:19, wherein expression of said polypeptide in a plant transformed with an isolated polynucleotide encoding said polypeptide results in alteration of the branching of the tassel, ear, or both, of the plant, when compared to a control plant not comprising said expressed polypeptide. Preferably, expression of said polypeptide results in a decrease in the branching, and even more preferably, the plant is maize.

In another preferred embodiment, an isolated polypeptide comprises an amino acid sequence of at least 80%, 85%, 90%, 95%, 96%, 97%, 98%, 99% or 100% sequence identity, based on the Clustal V method of alignment, when compared to SEQ ID NO:19, wherein expression of said polypeptide in a plant transformed with an isolated polynucleotide encoding said polypeptide results in alteration of pollen shed of the plant, when compared to a control plant not comprising said expressed polypeptide. Preferably, expression of said polypeptide results in a decrease in the pollen shed, and even more preferably, the plant is maize.

In another preferred embodiment, an isolated polypeptide comprises an amino acid sequence of at least 80%, 85%, 90%, 95%, 96%, 97%, 98%, 99% or 100% sequence identity, based on the Clustal V method of alignment, when compared to SEQ ID NO:19, wherein expression of said polypeptide in a plant exhibiting a ramosa3 mutant phenotype results in an decrease of branching of the tassel, ear, or both, of the plant. Preferably, the plant is maize.

In another preferred embodiment, an isolated polypeptide comprises an amino acid sequence of at least 80%, 85%, 90%, 95%, 96%, 97%, 98%, 99% or 100% sequence identity, based on the Clustal V method of alignment, when compared to SEQ ID NO:19, wherein expression of said polypeptide in a plant exhibiting a ramosa3 mutant phenotype results in an decrease of pollen shed of the plant. Preferably, the plant is maize.

Another preferred embodiment included within the present invention is an isolated polypeptide associated with branching of the tassel, ear, or both, of a plant (preferably maize), wherein said polypeptide has an amino acid sequence of at least 80%, 85%, 90%, 95%, 96%, 97%, 98%, 99% or 100% sequence identity, based on the Clustal V method of alignment, when compared to SEQ ID NO:19.

Another preferred embodiment is an isolated polypeptide associated with pollen shed of a plant (preferably maize), wherein said polypeptide has an amino acid sequence of at least 80%, 85%, 90%, 95%, 96%, 97%, 98%, 99% or 100% sequence identity, based on the Clustal V method of alignment, when compared to SEQ ID NO:19.

Still another preferred embodiment is an isolated polypeptide having trehalose-6-phosphate phosphatase activity, wherein the polypeptide has an amino acid sequence of at least 65%, 70%, 75%, 80%, 85%, 90%, 95%, 96%, 97%, 98%, 99% or 100% sequence identity, based on the Clustal V method of alignment, when compared to SEQ ID NO:19, 49, 68 or 69.

It is understood, as those skilled in the art will appreciate, that the invention encompasses more than the specific exemplary sequences. Alterations in a nucleic acid fragment which result in the production of a chemically equivalent amino acid at a given site, but do not effect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

The present invention also includes a recombinant DNA construct comprising a polynucleotide operably linked to a promoter that is functional in said plant, wherein said polynucleotide comprises an isolated polynucleotide of the present invention, such as a preferred polynucleotide as described above.

In one preferred embodiment, a recombinant DNA construct comprises a polynucleotide operably linked to a promoter that is functional in said plant, wherein said polynucleotide encodes a polypeptide having an amino acid sequence of at least 65%, 70%, 75%, 80%, 85%, 90%, 95%, 96%, 97%, 98%, 99% or 100% sequence identity, based on the Clustal V method of alignment, when compared to SEQ ID NO:19, 49, 68 or 69. Preferably, when compared to SEQ ID NO:68 or 69, the polypeptide has an amino acid sequence of at least 70%, 75%, 80%, 85%, 90%, 95%, 96%, 97%, 98%, 99% or 100% sequence identity, based on the Clustal V method of alignment.

In another preferred embodiment, a recombinant DNA construct comprises a polynucleotide operably linked to a promoter that is functional in said plant, wherein said polynucleotide encodes a polypeptide having an amino acid sequence of at least 80%, 85%, 90%, 95%, 96%, 97%, 98%, 99% or 100% sequence identity, based on the Clustal V method of alignment, when compared to SEQ ID NO:19.

The present invention also includes a suppression DNA construct.

A suppression construct preferably comprises a promoter functional in a plant operably linked to (a) all or part of (i) a nucleic acid sequence encoding a polypeptide having an amino acid sequence of at least 50% sequence identity, or any integer up to and including 100% sequence identity, based on the Clustal V method of alignment, when compared to SEQ ID NO:19, 49, 68 or 69, or (ii) a full complement of the nucleic acid sequence of (a)(i); (b) a region derived from all or part of a sense strand or antisense strand of a target gene of interest, said region having a nucleic acid sequence of at least 50% sequence identity, based on the Clustal V method of alignment, when compared to said all or part of a sense strand or antisense strand from which said region is derived, and wherein said target gene of interest encodes a RAMOSA3 (RA3) polypeptide or a SISTER OF RAMOSA3 (SRA) polypeptide; or (c) a nucleic acid sequence of at least 50% sequence identity, or any integer up to and including 100% identity, based on the Clustal V method of alignment, when compared to SEQ ID NO:15, 18, 47, 48 or 67. The suppression DNA construct preferably comprises a cosuppression construct, antisense construct, viral-suppression construct, hairpin suppression construct, stem-loop suppression construct, double-stranded RNA-producing construct, RNAi construct, or small RNA construct (e.g., an siRNA construct or an mRNA construct).

As used herein, "suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The term "suppression" includes lower, reduce, decline, decrease, inhibit, eliminate and prevent. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50% or any integer between 50% and 100% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and mRNA (microRNA) constructs.

"Antisense inhibition" refers to the production of antisense RNA transcripts capable of suppressing the expression of the target protein. "Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns, or the coding sequence.

"Cosuppression" refers to the production of sense RNA transcripts capable of suppressing the expression of the target protein. "Sense" RNA refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see Vaucheret et al. (1998) Plant J. 16:651-659; and Gura (2000) Nature 404:804-808).

A number of promoters can be used in recombinant DNA constructs and suppression DNA constructs of the present invention. The promoters can be selected based on the desired outcome, and may include constitutive, tissue-specific, inducible, or other promoters for expression in the host organism.

High level, constitutive expression of the candidate gene under control of the 35S promoter may have pleiotropic affects. However, tissue specific and/or stress-specific expression may eliminate undesirable affects but retain the ability to enhance drought tolerance. This affect has been observed in Arabidopsis (Kasuga et al. (1999) Nature Biotechnol. 17:287-91). As such, candidate gene efficacy may be tested when driven by different promoters.

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al., Nature 313:810-812 (1985)); rice actin (McElroy et al., Plant Cell 2:163-171 (1990)); ubiquitin (Christensen et al., Plant Mol. Biol. 12:619-632 (1989) and Christensen et al., Plant Mol. Biol. 18:675-689 (1992)); pEMU (Last et al., Theor. Appl. Genet. 81:581-588 (1991)); MAS (Velten et al., EMBO J. 3:2723-2730 (1984)); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

In choosing a promoter to use in the methods of the invention, it may be desirable to use a tissue-specific or developmentally regulated promoter. A preferred tissue-specific or developmentally regulated promoter is a DNA sequence which regulates the expression of a DNA sequence selectively in the cells/tissues of a plant critical to tassel development, seed set, or both, and limits the expression of such a DNA sequence to the period of tassel development or seed maturation in the plant. Any identifiable promoter may be used in the methods of the present invention which causes the desired temporal and spatial expression.

Promoters which are seed or embryo specific and may be useful in the invention include soybean Kunitz trysin inhibitor (Kti3, Jofuku and Goldberg, Plant Cell 1:1079-1093 (1989)), patatin (potato tubers) (Rocha-Sosa, M., et al. (1989) EMBO J. 8:23-29), convicilin, vicilin, and legumin (pea cotyledons) (Rerie, W. G., et al. (1991) Mol. Gen. Genet. 259:149-157; Newbigin, E. J., et al. (1990) Planta 180:461-470; Higgins, T. J. V., et al. (1988) Plant. Mol. Biol.

11:683-695), zein (maize endosperm) (Schemthaner, J. P., et al. (1988) EMBO J. 7:1249-1255), phaseolin (bean cotyledon) (Segupta-Gopalan, C., et al. (1985) Proc. Natl. Acad. Sci. U.S.A. 82:3320-3324), phytohemagglutinin (bean cotyledon) (Voelker, T. et al. (1987) EMBO J. 6:3571-3577), B-conglycinin and glycinin (soybean cotyledon) (Chen, Z-L, et al. (1988) EMBO J. 7:297-302), glutelin (rice endosperm), hordein (barley endosperm) (Marris, C., et al. (1988) Plant Mol. Biol. 10:359-366), glutenin and gliadin (wheat endosperm) (Colot, V., et al. (1987) EMBO J. 6:3559-3564), and sporamin (sweet potato tuberous root) (Hattori, T., et al. (1990) Plant Mol. Biol. 14:595-604). Promoters of seed-specific genes operably linked to heterologous coding regions in chimeric gene constructions maintain their temporal and spatial expression pattern in transgenic plants. Such examples include *Arabidopsis thaliana* 2S seed storage protein gene promoter to express enkephalin peptides in *Arabidopsis* and *Brassica napus* seeds (Vanderkerckhove et al., Bio/Technology 7:L929-932 (1989)), bean lectin and bean beta-phaseolin promoters to express luciferase (Riggs et al., Plant Sci. 63:47-57 (1989)), and wheat glutenin promoters to express chloramphenicol acetyl transferase (Colot et al., EMBO J. 6:3559-3564 (1987)).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Promoters which are timed to stress include the following: 1) the RD29A promoter (Kasuga et al. (1999) Nature Biotechnol. 17:287-91); 2) barley promoter, B22E; expression of B22E is specific to the pedicel in developing maize kernels ("Primary Structure of a Novel Barley Gene Differentially Expressed in Immature Aleurone Layers". Klemsdae, S. S. et al., Mol. Gen. Genet. 228(1/2):9-16 (1991)); and 3) maize promoter, Zag2 ("Identification and molecular characterization of ZAG1, the maize homolog of the *Arabidopsis* floral homeotic gene AGAMOUS", Schmidt, R. J. et al., Plant Cell 5(7):729-737 (1993)). Zag2 transcripts can be detected 5 days prior to pollination to 7 to 8 DAP, and directs expression in the carpel of developing female inflorescences and CimI which is specific to the nucleus of developing maize kernels. CimI transcript is detected 4 to 5 days before pollination to 6 to 8 DAP. Other useful promoters include any promoter which can be derived from a gene whose expression is maternally associated with developing female florets.

Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters". New promoters of various types useful in plant cells are constantly being discovered; numerous examples may be found in the compilation by Okamuro, J. K., and Goldberg, R. B., Biochemistry of Plants 15:1-82 (1989).

Particularly preferred promoters may include: RIP2, mLIP15, ZmCOR1, Rab17, CaMV 35S, RD29A, SAM synthetase, ubiquitin, CaMV 19S, nos, Adh, sucrose synthase, R-alele, or root cell promoter.

Recombinant DNA constructs and suppression DNA constructs of the present invention may also include other regulatory sequences, including but not limited to, translation leader sequences, introns, and polyadenylation recognition sequences. In another preferred embodiment of the present invention, a recombinant DNA construct of the present invention further comprises an enhancer or silencer.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell Biol.* 8:4395-4405 (1988); Callis et al., *Genes Dev.* 1:1183-1200 (1987). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds., Springer, New York (1994).

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

A translation leader sequence is a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) Molecular Biotechnology 3:225).

Any plant can be selected for the identification of regulatory sequences and genes to be used in creating recombinant DNA constructs and suppression DNA constructs of the present invention. Examples of suitable plant targets for the isolation of genes and regulatory sequences would include but are not limited to alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassaya, castorbean, cauliflower, celery, cherry, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radiscchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini. Particularly preferred plants for the identification of regulatory sequences are *Arabidopsis*, corn, wheat, soybean, and cotton.

The present invention also includes a plant comprising in its genome a recombinant DNA construct of the present invention (such as a preferred construct discussed above). Preferably, the recombinant DNA construct is stably integrated into the genome of the plant.

The present invention also includes a plant whose genome comprises a disruption (e.g., an insertion, such as a transposable element, or sequence mutation) of at least one gene (which may be heterologous or endogenous to the genome) encoding a polypeptide selected from the group consisting of a RAMOSA3 (RA3) polypeptide or a SISTER OF RAMOSA3 (SRA) polypeptide.

Also included in the present invention are any progeny of a plant of the present invention, and any seed obtained from such a plant or its progeny. Progeny includes subsequent generations obtained by self-pollination or out-crossing of a plant. Progeny also includes hybrids and inbreds. Preferably, in hybrid seed propagated crops, mature transgenic plants can be self-crossed to produce a homozygous inbred plant. The inbred plant produces seed containing the newly introduced recombinant DNA construct. These seeds can be grown to produce plants that would exhibit increased drought tolerance, or used in a breeding program to produce hybrid seed, which can be grown to produce plants that would exhibit increased drought tolerance. Preferably, the seeds are maize.

Preferably, a plant of the present invention is a monocotyledonous or dicotyledonous plant, more preferably, a maize or soybean plant, even more preferably a maize plant, such as a maize hybrid plant or a maize inbred plant. The plant may also be sunflower, sorghum, canola, wheat, alfalfa, cotton, rice, barley or millet.

Particularly preferred embodiments of plants of the present invention include:

1. A plant (preferably maize or soybean, more preferably a plant exhibiting a ramosa3 mutant phenotype) comprising in its genome a recombinant DNA construct comprising an isolated polypeptide having an amino acid sequence of at least 80%, 85%, 90%, 95%, 96%, 97%, 98%, 99% or 100% sequence identity, based on the Clustal V method of alignment, when compared to SEQ ID NO:19, wherein said plant exhibits alteration (preferably a decrease) of branching of the tassel, ear, or both, of said plant when compared to a control plant not comprising said recombinant DNA construct.

2. A plant (preferably maize or soybean, more preferably a plant exhibiting a ramosa3 mutant phenotype) comprising in its genome a recombinant DNA construct comprising an isolated polypeptide having an amino acid sequence of at least 80%, 85%, 90%, 95%, 96%, 97%, 98%, 99% or 100% sequence identity, based on the Clustal V method of alignment, when compared to SEQ ID NO:19, wherein said plant exhibits alteration (preferably a decrease) of pollen shed of said plant when compared to a control plant not comprising said recombinant DNA construct.

3. A plant (preferably maize or soybean, more preferably a plant exhibiting a ramosa3 mutant phenotype) comprising in its genome a recombinant DNA construct comprising an isolated polypeptide having an amino acid sequence of at least 65%, 70%, 75%, 80%, 85%, 90%, 95%, 96%, 97%, 98%, 99% or 100% sequence identity, based on the Clustal V method of alignment, when compared to SEQ ID NO:19, 49, 68 or 69, wherein said plant exhibits increased trehalose-6-phosphate phosphatase activity when compared to a control plant not comprising said recombinant DNA construct.

4. A plant (preferably maize or soybean, more preferably a plant exhibiting a ramosa3 mutant phenotype) comprising in its genome a recombinant DNA construct comprising an isolated polypeptide having an amino acid sequence of at least 65%, 70%, 75%, 80%, 85%, 90%, 95%, 96%, 97%, 98%, 99% or 100% sequence identity, based on the Clustal V method of alignment, when compared to SEQ ID NO:19, 49, 68 or 69, wherein said plant exhibits increased environmental stress tolerance (preferably drought tolerance) when compared to a control plant not comprising said recombinant DNA construct.

5. A plant (preferably maize or soybean) comprising in its genome:
    a suppression DNA construct comprising a promoter functional in a plant operably linked to:
    (a) all or part of (i) a nucleic acid sequence encoding a polypeptide having an amino acid sequence of at least 50% sequence identity, or any integer up to and including 100% sequence identity, based on the Clustal V method of alignment, when compared to SEQ ID NO:19, 49, 68 or 69, or (ii) a full complement of the nucleic acid sequence of (a)(i); or
    (b) a region derived from all or part of a sense strand or antisense strand of a target gene of interest, said region having a nucleic acid sequence of at least 50% sequence identity, based on the Clustal V method of alignment, when compared to said all or part of a sense strand or antisense strand from which said region is derived, and wherein said target gene of interest encodes a polypeptide selected from the group consisting of a RAMOSA3 (RA3) polypeptide or a SISTER OF RAMOSA3 (SRA) polypeptide,
    and wherein said plant exhibits increased branching of the tassel, ear, or both, and/or increased pollen shed, and/or reduced trehalose-6-phosphate phosphatase activity when compared to a control plant not comprising said suppression DNA construct. The suppression DNA construct preferably comprises a cosuppression construct, antisense construct, viral-suppression construct, hairpin suppression construct, stem-loop suppression construct, double-stranded RNA-producing construct, RNAi construct, or small RNA construct (e.g., an siRNA construct or an mRNA construct).

6. A plant (preferably maize or soybean) whose genome comprises a disruption (e.g., an insertion, such as a transposable element, or sequence mutation) of at least one gene (which may be heterologous or endogenous to the genome) encoding a polypeptide selected from the group consisting of a RAMOSA3 (RA3) polypeptide or a SISTER OF RAMOSA3 (SRA) polypeptide, wherein said disruption results in said plant exhibiting increased branching of the tassel, ear, or both, and/or increased pollen shed, and/or reduced trehalose-6-phosphate phosphatase activity when compared to a control plant not comprising said disruption. Preferably, relative to SEQ ID NO:15, the disruption comprises any one of the insertions shown in SEQ ID NOs:30, 32, 33, 35, 37, 39 or 43, or the deletion and rearrangement shown in SEQ ID NO:41.

7. Any progeny of the above plants 1-6, any seeds of the above plants 1-6, any seeds of progeny of the above plants 1-6, and cells from any of the above plants 1-6 and progeny.

The present invention also includes methods for altering branching of the tassel, ear, or both, of a plant; methods for altering pollen shed of a plant; methods for altering trehalose-6-phosphate phosphatase activity in a plant; and methods for increasing environmental stress tolerance (preferably drought tolerance) in a plant. Preferably, the plant is a monocotyledonous or dicotyledonous plant, more preferably, a maize or soybean plant, even more preferably a maize plant. The plant may also be sunflower, sorghum, canola, wheat, alfalfa, cotton, rice, barley or millet.

In one preferred embodiment, a method for altering branching of the tassel, ear, or both, of a plant, comprises: (a) introducing into a regenerable plant cell a recombinant DNA construct to produce transformed plant cells, said recombinant DNA construct comprising a polynucleotide operably linked to a promoter that is functional in a plant, wherein said polynucleotide encodes a polypeptide having an amino acid sequence of at least 80%, 85%, 90%, 95%, 96%, 97%, 98%, 99% or 100% sequence identity, based on the Clustal V method of alignment, when compared to SEQ ID NO:19; and (b) regenerating a transgenic plant from said transformed plant cell, wherein said transgenic plant comprises in its genome said recombinant DNA construct and wherein said transgenic plant exhibits an alteration in branching of the tassel, ear, or both, when compared to a control plant not comprising said recombinant DNA construct. The method may further comprise (c) obtaining a progeny plant derived from said transgenic plant, wherein said progeny plant comprises in its genome the recombinant DNA construct. Preferably, the transgenic plant or progeny thereof exhibits a decrease in branching of the tassel, ear, or both.

In another preferred embodiment, a method for altering pollen shed of a plant, comprises: (a) introducing into a regenerable plant cell a recombinant DNA construct to produce transformed plant cells, said recombinant DNA construct comprising a polynucleotide operably linked to a promoter that is functional in a plant, wherein said polynucleotide encodes a polypeptide having an amino acid sequence of at least 80%, 85%, 90%, 95%, 96%, 97%, 98%, 99% or 100% sequence identity, based on the Clustal V method of alignment, when compared to SEQ ID NO:19; and (b) regenerating a transgenic plant from said transformed plant cell, wherein said transgenic plant comprises in its genome said recombinant DNA construct and wherein said transgenic plant exhibits an alteration in pollen shed, when compared to a control plant not comprising said recombinant DNA construct. The method may further comprise (c) obtaining a progeny plant derived from said transgenic plant, wherein said progeny plant comprises in its genome the recombinant DNA construct. Preferably, the transgenic plant or progeny thereof exhibits a decrease in pollen shed.

Another preferred method of the present invention is a method for altering trehalose-6-phosphate phosphatase activity in a plant, comprising: (a) introducing into a regenerable plant cell a recombinant DNA construct to produce transformed plant cells, said recombinant DNA construct comprising a polynucleotide operably linked to a promoter that is functional in a plant, wherein said polynucleotide encodes a polypeptide having an amino acid sequence of at least 65%, 70%, 75%, 80%, 85%, 90%, 95%, 96%, 97%, 98%, 99% or 100% sequence identity, based on the Clustal V method of alignment, when compared to SEQ ID NO:19, 49, 68 or 69; and (b) regenerating a transgenic plant from said transformed plant cell, wherein said transgenic plant comprises in its genome said recombinant DNA construct and wherein said transgenic plant exhibits an alteration in trehalose-6-phosphate phosphatase activity, when compared to a control plant not comprising said recombinant DNA construct. The method may further comprise (c) obtaining a progeny plant derived from said transgenic plant, wherein said progeny plant comprises in its genome the recombinant DNA construct. Preferably, the transgenic plant or progeny thereof exhibits an increase in trehalose-6-phosphate phosphatase activity.

In another preferred embodiment, a method for increasing environmental stress tolerance (preferably drought tolerance) of a plant, comprises: (a) introducing into a regenerable plant cell a recombinant DNA construct to produce transformed plant cells, said recombinant DNA construct comprising a polynucleotide operably linked to a promoter that is functional in a plant, wherein said polynucleotide encodes a polypeptide having an amino acid sequence of at least 65%, 70%, 75%, 80%, 85%, 90%, 95%, 96%, 97%, 98%, 99% or 100% sequence identity, based on the Clustal V method of alignment, when compared to SEQ ID NO:19, 49, 68 or 69; and (b) regenerating a transgenic plant from said transformed plant cell, wherein said transgenic plant comprises in its genome said recombinant DNA construct and wherein said transgenic plant exhibits an increase in environmental stress tolerance (preferably drought tolerance), when compared to a control plant not comprising said recombinant DNA construct. The method may further comprise (c) obtaining a progeny plant derived from said transgenic plant, wherein said progeny plant comprises in its genome the recombinant DNA construct.

In yet another preferred embodiment, a method for increasing branching of the tassel, ear, or both, and/or increasing pollen shed, and/or reducing trehalose-6-phosphate phosphatase activity a plant, comprises: (a) introducing into a regenerable plant cell a suppression DNA construct to produce transformed plant cells, said suppression DNA construct comprising a promoter functional in a plant operably linked to (i) all or part of (A) a nucleic acid sequence encoding a polypeptide having an amino acid sequence of at least 50% sequence identity, or any integer up to and including 100% sequence identity, based on the Clustal V method of alignment, when compared to SEQ ID NO:19, 49, 68 or 69, or (B) a full complement of the nucleic acid sequence of (i)(A), or (ii) a region derived from all or part of a sense strand or antisense strand of a target gene of interest, said region having a nucleic acid sequence of at least 50% sequence identity, based on the Clustal V method of alignment, when compared to said all or part of a sense strand or antisense strand from which said region is derived, and wherein said target gene of interest encodes a polypeptide selected from the group consisting of a RAMOSA3 (RA3) polypeptide or a SISTER OF RAMOSA3 (SRA) polypeptide; and (b) regenerating a transgenic plant from said transformed plant cell, wherein said transgenic plant comprises in its genome said suppression DNA construct and wherein said transgenic plant exhibits increased branching of the tassel, ear, or both, and/or increased pollen shed, and/or reduced trehalose-6-phosphate phosphatase activity when compared to a control plant not comprising said suppression DNA construct. The method may further comprise (c) obtaining a progeny plant derived from said transgenic plant, wherein said progeny plant comprises in its genome the suppression DNA construct.

The introduction of recombinant DNA constructs of the present invention into plants may be carried out by any suitable technique, including but not limited to direct DNA uptake, chemical treatment, electroporation, microinjection, cell fusion, infection, vector mediated DNA transfer, bombardment, or *Agrobacterium* mediated transformation.

Preferred techniques are set forth below in Example 6 for transformation of maize plant cells and in Example 7 for transformation of soybean plant cells.

Other preferred methods for transforming dicots, primarily by use of *Agrobacterium tumefaciens*, and obtaining transgenic plants include those published for cotton (U.S. Pat. No. 5,004,863, U.S. Pat. No. 5,159,135, U.S. Pat. No. 5,518,908); soybean (U.S. Pat. No. 5,569,834, U.S. Pat. No. 5,416,011, McCabe et. al., Bio/Technology 6:923 (1988), Christou et al., Plant Physiol. 87:671 674 (1988)); Brassica (U.S. Pat. No. 5,463,174); peanut (Cheng et al., Plant Cell Rep. 15:653 657 (1996), McKently et al., Plant Cell Rep. 14:699 703 (1995)); papaya; and pea (Grant et al., Plant Cell Rep. 15:254 258, (1995)).

Transformation of monocotyledons using electroporation, particle bombardment, and *Agrobacterium* have also been reported and are included as preferred methods, for example, transformation and plant regeneration as achieved in asparagus (Bytebier et al., Proc. Natl. Acad. Sci. (USA) 84:5354, (1987)); barley (Wan and Lemaux, Plant Physiol 104:37 (1994)); *Zea mays* (Rhodes et al., Science 240:204 (1988), Gordon-Kamm et al., Plant Cell 2:603 618 (1990), Fromm et al., BiolTechnology 8:833 (1990), Koziel et al., BiolTechnology 11: 194, (1993), Armstrong et al., Crop Science 35:550 557 (1995)); oat (Somers et al., BiolTechnology 10: 15 89 (1992)); orchard grass (Horn et al., Plant Cell Rep. 7:469 (1988)); rice (Toriyama et al., TheorAppl. Genet. 205:34, (1986); Part et al., Plant Mol. Biol. 32:1135 1148, (1996); Abedinia et al., Aust. J. Plant Physiol. 24:133 141 (1997); Zhang and Wu, Theor. Appl. Genet. 76:835 (1988); Zhang et al. Plant Cell Rep. 7:379, (1988); Battraw and Hall, Plant Sci. 86:191 202 (1992); Christou et al., BiolTechnology 9:957 (1991)); rye (De la Pena et al., Nature 325:274 (1987)); sugarcane (Bower and Birch, Plant J. 2:409 (1992)); tall fescue (Wang et al., BiolTechnology 10:691 (1992)), and wheat (Vasil et al., Bio/Technology 10:667 (1992); U.S. Pat. No. 5,631,152).

There are a variety of methods for the regeneration of plants from plant tissue. The particular method of regeneration will depend on the starting plant tissue and the particular plant species to be regenerated.

The regeneration, development, and cultivation of plants from single plant protoplast transformants or from various transformed explants is well known in the art (Weissbach and Weissbach, In: Methods for Plant Molecular Biology, (Eds.), Academic Press, Inc. San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous isolated nucleic acid fragment that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

Assays to detect proteins may be performed by SDS-polyacrylamide gel electrophoresis or immunological assays. Assays to detect levels of substrates or products of enzymes may be performed using gas chromatography or liquid chromatography for separation and UV or visible spectrometry or mass spectrometry for detection, or the like.

Determining the levels of mRNA of the enzyme of interest may be accomplished using northern-blotting or RT-PCR techniques. Once plants have been regenerated, and progeny plants homozygous for the transgene have been obtained, plants will have a stable phenotype that will be observed in similar seeds in later generations.

The present invention also includes a method for determining whether a plant exhibits a ramosa3 mutant genotype comprising: (a) isolating genomic DNA from a subject; (b) performing a PCR on the isolated genomic DNA using the primer pair consisting of NS432 (SEQ ID NO:16) and NS411 (SEQ ID NO:17); and (c) analyzing results of the PCR for the presence of a larger DNA fragment as an indication that the subject exhibits the ramosa3 mutant genotype.

Also included in the present invention is a method for determining whether a plant exhibits a ramosa3 mutant genotype comprising: (a) isolating genomic DNA from a subject; (b) performing a PCR on the isolated genomic DNA using any one of the following primer pairs: SEQ ID NOS:16 and 17; SEQ ID NOS:20 and 21; SEQ ID NOS:22 and 23; SEQ ID NOS:24 and 25; SEQ ID NOS:26 and 27 or SEQ ID NOS:28 and 29; and (c) analyzing the results of the PCR for the presence of a larger or smaller DNA fragment, relative to a non-mutant fragment, as an indication that the subject exhibits the ramosa3 mutant genotype.

Another method included in the present invention is a method for selecting a first maize plant by marker assisted selection of a quantitative trait locus ("QTL") associated with branching of the tassel, ear or both, the method comprising: determining the presence of a locus in the first maize plant, wherein the locus hybridizes with a first nucleic acid that is genetically linked to a nucleic acid sequence having at least 90% sequence identity, based on the Clustal V method of alignment, when compared to SEQ ID NO:15; and selecting the first maize plant comprising the locus that hybridizes with the first nucleic acid; thereby selecting the maize plant containing a QTL associated with branching of the tassel, ear or both.

As described above, the present invention includes, among other things, compositions and methods for modulating (i.e., increasing or decreasing) the level of polypeptides of the present invention in plants. In particular, the polypeptides of the present invention can be expressed at developmental stages, in tissues, and/or in quantities which are uncharacteristic of non-recombinantly engineered plants. In addition to altering (increasing or decreasing) branching, pollen shed or trehalose-6-phosphate phosphatase activity, it is believed that increasing or decreasing the level of polypeptides of the present invention in plants also can also have an impact on yield by altering the numbers of fruits and seeds produced by the inflorescences (due to extra branches) or by making plants more compact allowing them to be grown under stringent conditions, e.g., planted at high density or under adverse weather conditions, such as drought. Thus, the present invention also provides utility in such exemplary applications as improvement of yield or growth under stressful conditions.

The isolated nucleic acids and proteins and any embodiments of the present invention can be used over a broad range of plant types, particularly monocots such as the species of the Family Graminiae including *Sorghum bicolor* and *Zea mays*. The isolated nucleic acid and proteins of the present invention can also be used in species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica,*

*Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Triticum, Bambusa, Dendrocalamus,* and *Melocanna.*

EXAMPLES

The present invention is further illustrated in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Phenotypic Analysis of ra3 Mutants

A mutant line with branched inflorescences was isolated in a non-targeted Mutator (Mu) transposon tagging family, and found to be an allele of ramosa3 (ra3). Although ra3 is a classical mutant of maize, first described in 1954 by H. S. Perry (see also, Table 1 of Veit et al. *Plant Cell* 5:1205-1215 (1993)), it had not been characterized in detail. Only the mature inflorescence phenotype had been reported, and there was some confusion about the map location, as explained below in Example 2.

To analyze ra3 mutant phenotypes, ra3 reference allele plants (ra3-ref, Maize Genetics CoOp Stock Center) were introgressed into B73 for at least 3 generations. During vegetative development, no differences were observed in ra3 plants compared to wild type sibs. In the inflorescence stage, ra3 mutants had irregular long branches in the ears, whereas wild type sib ears had a more compact and organized rachis. Also, irregular seed rows were present in contrast to the neatly organized rows in wild-type ears. See FIG. 1. As shown on FIG. 1, wild-type ear (A) has nicely arranged rows and no long branches, whereas ra3 mutant ears (B) have long branches and irregular rows of kernels. Occasionally, ra3 ears are covered in long branches (B, right). Wild type tassels normally have long branches at their base (C), and ra3 mutant tassels (D) have more branches.

Mutant ra3 ears also had "upside-down" or inverted embryo orientations, which may indicate indeterminacy in the spikelet axis. These defects in ra3 ears were usually seen only at the base, though occasionally the ears were irregularly branched along their whole length (FIG. 1B). As in the ear, ra3 tassels had more branches than wild-type tassels, although overall the developmental defects appeared to be milder than in the ears.

To determine how these defects in the mature inflorescences arise, scanning electron microscopy (SEM) was used to follow early ear and tassel development. The development of ears is described as follows. During the vegetative to inflorescence transition stage, there was no difference between ra3 and wild-type (FIG. 2A, E), and the ra3 inflorescence meristem (IM) initiated spikelet pair meristems (SPMs) as in wild-type (FIG. 2B, F). The first defects that were observed in immature ra3 ears were enlarged and irregular sized SPMs, when the ear primordia were around 1.5 mm long. Slightly later in development, when the ear primordia were around 2 mm long, the conversion of SPMs to indeterminate meristems that produce additional SPMs was observed (FIG. 2F, arrow 1). Because this SPM produced additional SPMs, we chose to call it "branch meristem*" (BM*), to reflect its similarity to the BMs at the base of normal tassels. As ear development proceeded, the ra3 SPMs made 3-4 glumes before the conversion to a BM* (FIG. 2G, arrows 2), while wild-type SMs made only 2 glumes that subtended the SM (arrows 2, FIG. 2C). Sometimes, floral meristems (FMs), rather than SMs, were produced inside these extra glumes in ra3 mutants (FIG. 2G). In summary, the SPMs that converted to BM* in ra3 ears had two possible identities, SPM* or a mixture of SPM and SM (SPM*+SM*). In this scheme, SPM* produced several glumes containing only SPMs and SMs, whereas "SPM*+SM*" produced several glumes subtending FMs.

Mutant ra3 SMs also showed other types of identity defects. For example, they often made multiple FMs (arrows 3, FIG. 2H), whereas wild-type SMs produce only two FMs. Mutant ra3 SMs can even convert to BM* identity after making several FMs. As in mature ears (FIG. 1), usually only the meristems in the lower half of the ear showed these defects.

In ra3 tassels, similar developmental defects as in ra3 ears were observed. For example, they also produced more indeterminate SPMs. This resulted in about double the number of long branches in ra3 tassels (wild-type 6.8±1.4; ra3 13.6±2.8 branches).

In summary, ra3 ears and tassels showed a range of phenotypic defects; a summary for the ear is presented in FIG. 3. The developmental analysis showed that in general RA3 functions to impose determinacy and identity on the different meristem types in the inflorescences. Although the IMs are normal, the SPMs, SMs and FMs are all more indeterminate in ra3 mutants compared to wild type.

Example 2

Mapping and Isolation of ra3

According to the maize genetic map available, in 2004, at the Maize Genetics and Genomics Database, ra3 was listed as being mapped to chromosome 4; however, we were unable to reproduce those results. To address this discrepancy, ra3 and sib DNAs were provided for analysis by the the Missouri Maize Mapping Project [Coe, E., Cone, K., McMullen, M., Chen, S. S., Davis, G., Gardiner, J., Liscum, E., Polacco, M., Paterson, A., Sanchez-Villeda, H., Soderlund, C., and Wing, R., *Access to the maize genome: an integrated physical and genetic map*. Plant Physiol, 2002. 128(1): p. 9-12.].

Using bulk segregant analysis, ra3 was mapped to chromosome 7, bin 4.

For more detailed mapping studies, larger mapping populations were constructed using the ra3-ref allele and an allele ("ra3-fea1") that was isolated from a Mu line carrying a fasciated ear mutant (fea1, [Jackson, D. and Hake, S., *The genetics of ear fasciation in maize*. Maize Genetics Cooperation Newsletter, 1999. 73: p. 2]).

The ra3 and fea1 mutations segregated independently in this line, indicating that these mutations are in different genes. F2s of each ra3 allele crossed to B73 were made, and high-resolution mapping was conducted using simple sequence repeat (SSR), restriction fragment length polymorphism (RFLP), cleaved amplified polymorphic sequences (CAPS) and derived CAPS (dCAPS) markers (FIG. 4).

By analyzing 74 ra3-ref mutants in the F2, one recombinant between marker csu597 (SEQ ID NOS:1 & 2) and ra3 and two recombinants in different individuals between marker umc1412 (SEQ ID NOS:3 & 4) and ra3 were identified, placing the ra3 locus between these two markers. To further delimit the ra3 region, a larger number of recombinants were screened, and new CAPS markers, a14 (SEQ ID NOS:5 & 6) and n20 (SEQ ID NOS:7 & 8) were created using BAC end sequences covering part of the ra3 region. DNA amplified from ra3-ref and B73 using these sets of primers gave polymorphisms when digested with Fok1 for a14 and HindIII for n20. Nine recombinants out of 873 ra3 mutants between a14 and ra3 and 10 recombinants between n20 and ra3 were obtained. The number of cross overs indicated that the genetic distance between ra3 and a14 was 0.7+/−0.2 cM and the genetic distance between ra3 and n20 was 0.6+/−0.2 cM.

This region of the maize genome was covered by three BAC clones, c0387K01, b0505C08 and b0063D15 [Cone, K. C. et al., Genetic, physical, and informatics resources for maize. On the road to an integrated map. Plant Physiol, 2002. 130(4): p. 1598-605]. New markers were made from these BACs by screening for non-repetitive DNA fragments. Southern blots were made of each BAC clone digested with several restriction enzymes, and the blot was probed first with maize genomic DNA, and after imaging, probed again with the BAC DNA. Upon comparison of the two blot images, bands were identified that had a signal with the BAC hybridization but not with total genomic DNA hybridization. These bands were cataloged as being non-repetitive, and designated as "cold bands" (cb, FIG. 4). These cold bands were used either as RFLP probes or, after sequencing, were converted into d-CAPS markers. The d-CAPS marker, cb.g1E, was made from the sequence of cold band e; the forward and reverse primers for cb.g1E are given as SEQ ID NO:9 and SEQ ID NO:10, respectively. Using these additional markers, it was determined that the ra3 locus was positioned on the BAC c0387K01 (FIG. 4).

The nucleotide sequence of BAC c0387K01 was determined and this sequence information was used to design primers for amplification of DNA from the recombinants identified earlier. NS346 (SEQ ID NO:11) and NS347 (SEQ ID NO:12) were one primer pair; NS362 (SEQ ID NO:13) and NS363 (SEQ ID NO:14) was a second primer pair. These two primer pairs were used to generate PCR product length polymorphisms, which were used to delimit the RA3 locus to a single predicted gene (FIG. 4).

Example 3

RA3 and SRA Gene Structure and Phylogenetic Analysis

The nucleotide sequence shown in SEQ ID NO:15 was deduced from BAC c038K01, and encodes the RA3 gene with 3 kb of sequence upstream (5') of the ATG initiation codon, and 7.5 kb downstream (3') of the TGA stop codon. Note that exons in SEQ ID NO:15 are displayed only for the region from the start codon to the stop codon, and are not shown for the 5' or 3' Untranslated Regions (5'- and 3'-UTRs).

The cDNA sequence corresponding to the RA3 region was isolated by reverse transcription of poly(A)-RNA followed by PCR. The Quiagen OneStep RT-PCR kit was used according to the manufacturers specifications. The primer set used was NS432 (SEQ ID NO:16) and NS411 (SEQ ID NO:17). SEQ ID NO:18 is the nucleotide sequence of the protein-coding region deduced from the PCR product obtained using the NS432 and NS411 primers. The corresponding amino acid sequence of the RAMOSA3 polypeptide is shown as SEQ ID NO:19.

The RA3 gene encodes a predicted protein of 361 amino acids with significant similarity to trehalose-6-phosphate phosphatases (TPPs). The predicted polypeptide has a non-conserved N-terminal region of ~80 amino acids followed by the TPP domain which contains two "phosphatase boxes" (see FIG. 5, part A, region labeled "3") [Goddijn, O. J. and van Dun, K., Trehalose metabolism in plants. Trends Plant Sci, 1999. 4(8): p. 315-319; Thaller, M. C., Schippa, S., and Rossolini, G. M., Conserved sequence motifs among bacterial, eukaryotic, and archaeal phosphatases that define a new phosphohydrolase superfamily. Protein Sci, 1998. 7(7): p. 1647-52; Vogel, G., Aeschbacher, R. A., Muller, J., Boller, T., and Wiemken, A., Trehalose-6-phosphate phosphatases from Arabidopsis thaliana: identification by functional complementation of the yeast tps2 mutant. Plant J, 1998. 13(5): p. 673-83]. FIG. 5, part A contains an "A-domain" (SEQ ID NO:45) and a "B-domain" (SEQ ID NO:46), as designated by Vogel et al. (1998) Plant J 13(5):673-83.

RA3 is very similar in the TPP domain to the functional TPPs, AtTPPA and AtTPPB, from Arabidopsis, and the A- and B-domains of RA3 and AtTPPB are identical. In a comparison of plant TPP proteins to the corresponding yeast protein, RA3 is actually more similar to yeast TPS2 than is the Arabidopsis AtTPPA (20% vs. 16% identity).

Adjacent to RA3 there was a highly similar TPP gene, which we have designated SISTER OF RAMOSA3 (SRA). The genomic DNA sequence containing the SRA gene is shown in SEQ ID NO:47. The nucleotide sequence of the protein-coding region of the SRA gene is shown in SEQ ID NO:48, and the corresponding amino acid sequence of the SRA polypeptide is shown in SEQ ID NO:49. A cDNA clone, my.cs1.pk0072.d4, was prepared from RNA isolated from the leaf and sheath of 5-week old Zea mays L. plants, and it contains a fragment of the SRA gene. Part of the nucleotide sequence of the cDNA insert of clone my.cs1.pk0072.d4 is presented in SEQ ID NO:50.

In the region of conserved synteny in rice, only a single rice TPP gene, gi33146623 (SEQ ID NO:43), is found. RA3 and SRA have 60.4 and 59.3% overall sequence identity, respectively, with the rice TPP (Table 1). Genbank and the maize sequence assemblies available at the Maize Genetics and Genomics Database and at The Institute for Genomic Research Maize Database were examined for the presence of closely related homologs to RA3 and SRA. Because the maize proteins are not yet annotated we named them "ZmRA3 Like" ("ZmRA3L").

A phylogenetic analysis of TPP genes from Arabidopsis, rice and maize is shown in a neighbor-joining tree (FIG. 5, part B). [Swofford, D., PAUP-A COMPUTER-PROGRAM FOR PHYLOGENETIC INFERENCE USING MAXIMUM PARSIMONY. JOURNAL OF GENERAL PHYSIOLOGY, 1993. 102: p. A9] The tree indicates that RA3, SRA and gi33146623 (SEQ ID NO:43) are most closely related, and RA3 and SRA are likely paralogs. TPPB, a functional TPP from *Arabidopsis* (At1g78090; SEQ ID NO:53 corresponding to NCBI GI NO. 2944180) is the most closely related *Arabidopsis* protein.

FIGS. 6A-6D show a sequence alignment of the amino acid sequences for the following trehalose-6-phosphate phosphatases: RA3 (SEQ ID NO:19); SRA (SEQ ID NO:49); rice TPP (SEQ ID NO:51); *Arabidopsis* TPPA (SEQ ID NO:52); *Arabidopsis* TPPB (SEQ ID NO:53); corn TPP (SEQ ID NO:54); and soybean TPP (SEQ ID NO:55). Also shown are alignments with two truncated forms of *Arabidopsis* TPPA and TPPB, in which the N-terminal 91 amino acids have been removed from each. An asterisk above an amino acid residue indicates that the position is totally conserved among the given SEQ ID NOs, with respect to the *Arabidopsis thaliana* AtTPPB sequence. Below the sequences are shown two domains, A and B, that are conserved among trehalose-6-phosphate phosphatases, as described in Vogel et al. (1998) *Plant J* 13(5):673-683. The given sequence for each conserved domain is taken from the *Arabidopsis thaliana* AtTPPB amino acid sequence at these positions. FIGS. 6A-6D indicate that regions of high sequence similarity are located in the carboxy-terminal 70% of the consensus sequence. Vogel et al. have noted that the AtTPPA and AtTPPB proteins have high sequence conservation to each other except for the amino-terminal 100 amino acids, which they note have features in common with chloroplast transit peptides. Vogel et al. have shown enzyme activity for AtTPPA, AtTPPB, and a truncated AtTPPA polypeptide that is missing the first 91 amino acids.

The data in Table 1 show the percent identity for each pair of amino acid sequences from the group consisting of SEQ ID NOS:19, 49, 51, 52, 53, 54, 55, an enzymatically active fragment of SEQ ID NO:52 (AtTPPA) in which the first 91 amino acids are missing (Vogel et al. (1998) *Plant J* 13(5): 673-683), and a corresponding truncated AtTPPB polypeptide in which the first 91 amino acids have been removed. From this comparison of percent identities, the RA3 and SRA polypeptides were found to have a higher percent identity to the AtTPPB truncated polypeptide, than the AtTPPA truncated polypeptide.

TABLE 1

Percent Sequence Identity of Amino Acid Sequences of Plant Trehalose-6-Phosphate Phosphatases With Each Other

| SEQ ID NO: | Percent Identity to SEQ ID NO: | | | | | | | | |
|---|---|---|---|---|---|---|---|---|---|
| | 19 | 49 | 51 | 52 | 53 | 54 | 55 | 52t* | 53t** |
| 19 | — | 60.4 | 60.4 | 46.0 | 49.0 | 47.4 | 46.3 | 53.1 | 60.1 |
| 49 | 60.4 | — | 59.3 | 43.0 | 47.6 | 45.0 | 45.1 | 51.7 | 58.7 |
| 51 | 60.4 | 59.3 | — | 44.5 | 48.1 | 47.5 | 45.1 | 53.4 | 59.4 |
| 52 | 46.0 | 43.0 | 44.5 | — | 46.5 | 55.3 | 60.2 | 100.0 | 56.9 |
| 53 | 49.0 | 47.6 | 48.1 | 46.5 | — | 48.0 | 46.0 | 54.8 | 100.0 |
| 54 | 47.4 | 45.0 | 47.5 | 55.3 | 48.0 | — | 54.2 | 60.5 | 59.4 |
| 55 | 46.3 | 45.1 | 45.1 | 60.2 | 46.0 | 54.2 | — | 65.6 | 56.5 |
| 52t* | 53.1 | 51.7 | 53.4 | 100.0 | 54.8 | 60.5 | 65.6 | — | 56.9 |
| 53t** | 60.1 | 58.7 | 59.4 | 56.9 | 100.0 | 59.4 | 56.5 | 56.9 | — |

*52t refers to a truncation of the AtTPPA polypeptide (SEQ ID NO:52), in which 91 amino acids have been removed from the amino terminus.
**53t refers to a truncation of the AtTPPB polypeptide (SEQ ID NO:53), in which 91 amino acids have been removed from the amino terminus.

Example 4

Sequence Analysis of ra3 Mutant Alleles

To confirm that the predicted locus encodes RA3, seven ra3 alleles were sequenced. These ra3 alleles were either preexisting alleles or were isolated from targeted screens. Each had a lesion in the candidate gene, indicating that it encodes RA3 (Table 2).

Coding regions of mutant alleles ra3-ref, ra3-fea1, ra3-EV, ra3-NI, ra3-bre, ra3-JL and ra3-NS were sequenced following amplification using the following primer sets: 5'UTR-exon2 forward and reverse primers (SEQ ID NO:20 & 21, respectively); exon3-exon4 forward and reverse primers (SEQ ID NO:22 & 23, respectively); exon5-exon7 forward and reverse primers (SEQ ID NO:24 & 25, respectively); exon8-exon10 forward and reverse primers (SEQ ID NO:26 & 27, respectively); and exon11-3'UTR forward and reverse primers (SEQ ID NO:28 & 29, respectively).

The ra3-ref mutant allele has a 4 bp insertion in exon7 (SEQ ID NO:30). This results in a frame-shift after amino acid 249 and a premature stop codon after 305 amino acids. The predicted ra3-ref polypeptide is shown in SEQ ID NO:31.

The ra3-fea1 mutant allele contains the following two mutations: 1) an insertion of an ILS-1-like transposon element in the 5'-UTR region of the ra3-fea1 mutant gene (SEQ ID NO:32); and 2) a 4 bp insertion in the coding sequence of exon7 (SEQ ID NO:33), leading to a frame-shift after amino acid 258 and a premature stop codon after 305 amino acids. The predicted amino acid sequence of the ra3-fea1 polypeptide is shown in SEQ ID NO:34.

The ra3-EV mutant allele carries a 4 bp insertion in exon6 (SEQ ID NO:35). This results in a frame-shift after amino acid 224 and a premature stop codon after 305 amino acids. The predicted amino acid sequence of the ra3-EV polypeptide is shown in SEQ ID NO:36.

The ra3-NI mutant allele has an insertion of 141 bp in exon10 (SEQ ID NO:37), leading to a different protein sequence after amino acid 333 and a premature stop codon after 335 amino acids. The predicted amino acid sequence of the ra3-NI polypeptide is shown in SEQ ID NO:38.

The ra3-bre mutant allele has a 10 bp insertion between exon6 and exon7 (SEQ ID NO:39), leading to a frame-shift after amino acid 241 and a premature stop codon after 243 amino acids. The predicted amino acid sequence of the ra3-bre polypeptide is shown in SEQ ID NO:40.

The ra3-JL mutant allele has a deletion and rearrangement in exon6 (SEQ ID NO:41), leading to a different protein sequence after amino acid 217 and a premature stop codon after 246 amino acids. The predicted amino acid sequence of the ra3-JL polypeptide is shown in SEQ ID NO:42.

The ra3-NS mutant allele has a 2 bp insertion in exon6 (SEQ ID NO:43), leading to a frame-shift after amino acid 222 and a premature stop codon after 299 amino acids. The predicted amino acid sequence of the ra3-NS polypeptide is shown in SEQ ID NO:44.

The nature of some alleles was unusual, for example some alleles obtained from transposon screens had insertions of only a few nucleotides, possibly reflecting abortive transposition events. Both ra3-ref and ra3-fea1 had a 4 bp insertion in exon 7, at different positions, and ra3-fea1 also contained a transposon in the 5' region. In each allele the mutation caused a frame-shift, and a premature stop codon.

TABLE 2

Seven ra3 Alleles Have Mutations in the Candidate Locus.

| Allele | Source | Lesion |
|---|---|---|
| ra3-ref | Maize Genetics Stock Center | 4 bp insertion into exon 7 |

TABLE 2-continued

Seven ra3 Alleles Have Mutations in the Candidate Locus.

| Allele | Source | Lesion |
|---|---|---|
| ra3-fea1 | Mu transposon stock (D. Jackson) | ~2 kb ILS-like transposon between TATA box and exon 1; 4 bp insertion into exon 7 |
| ra3-EV | Ac-Ds stock (E. Vollbrecht) | 4 bp insertion into exon 6 |
| ra3-NI | EMS screen (N. Inada) | 141 bp insertion into exon 10 |
| ra3-bre | Unknown (E. Irish) | 10 bp insertion in cDNA, between exon 6 and exon 7 |
| ra3-JL | Mu transposon screen | Deletion and rearrangement in exon 6 |
| ra3-NS | Spin transposon screen | 2 bp insertion into exon 6 |

Each mutant allele has a stop codon before the second phosphatase box, except for ra3-NI, which has a stop codon after the second phosphatase box. This correlates with phenotype, since ra3-NI mutants have the mildest phenotype.

Example 5

RA3 Gene Expression Profile

RT-PCR analysis was used to determine where and when during development RA3 and SRA are expressed. First, RT-PCR primers were tested on the ra3 alleles. In mRNA isolated from 1 cm long ear primordia, a transcript was detected in wild type (B73) ears and in ra3-EV, ra3-NI and ra3-bre. However, no transcript was detected in mRNA from ra3-fea1 immature ears, indicating the specificity of these primers for RA3 (FIG. 7A). During development, RA3 was expressed most strongly during early female and male inflorescence development, and peaked at around 2-5 mm in ear and tassel development. At this stage, SPM and SM are being initiated on the developing inflorescences. Very low levels of RA3 transcript were detected in root or vegetative apex, and were not detected in leaf (FIG. 7B). On the other hand, SRA was expressed more evenly throughout development, with a slightly higher expression in root and larger tassel primordia (FIG. 7B).

Additionally, in situ hybridization was used to determine if RA3 expression was spatially regulated during early inflorescence development. RA3 expression was observed in ear primordia in a cup-shaped group of cells at the base of SPMs, SMs and FMs, and at the boundary between upper and lower florets (FIG. 8). This expression is specific for RA3, as it was not seen in ra3-ref ears. Together with the developmental analysis, this highly restricted expression patter suggests an important developmental role for RA3 in maize inflorescence development.

In summary, the RA3 gene of maize is expressed preferentially in restricted domains at early stages of inflorescence development. Phenotypic analysis suggests that RA3 acts at this stage to restrict the determinacy and identity of different meristem types in the inflorescence.

Example 6

Prophetic Example

Expression of Recombinant DNA in Monocot Cells

A recombinant DNA construct comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a recombinant DNA construct encoding, in the 5' to 3' direction, the maize 27 kD zein promoter, a cDNA fragment encoding the instant polypeptides, and the 10 kD zein 3' region.

The recombinant DNA construct described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from cauliflower mosaic virus (Odell et al. (1985) Nature 313:810-812) and the 3' region of the nopaline synthase gene from the T-DNA of the Ti plasmid of *Agrobacterium tumefaciens*.

The particle bombardment method (Klein et al. (1987) *Nature* 327:70-73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialaphos (5 mg per liter) and lacks casein or proline. The tissue continues to grow slowly on this medium. After an additional 2 weeks the tissue can be transferred to fresh N6 medium containing bialaphos. After 6 weeks, areas of about 1 cm in diameter of actively growing callus can be identified on some of the plates containing the bialaphos supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833-839).

Example 7

Prophetic Example

Expression of Recombinant DNA in Dicot Cells

An expression cassette composed of the promoter from the B-conglycinin or glycinin genes (Chen, Z-L, et al. (1988) EMBO J. 7:297-302), 5-prime to the cDNA fragment, can be constructed and be used for expression of the instant polypeptides in transformed soybean. The pinII terminator can be placed 3-prime to the cDNA fragment. Such construct may be used to overexpress the instant polypeptides. It is realized that one skilled in the art could employ different promoters and/or 3-prime end sequences to achieve comparable expression results.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos, which produce secondary embryos, are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from cauliflower mosaic virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µL spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 8

Prophetic Example

Expression of Recombinant DNA in Microbial Cells

The cDNAs encoding the instant polypeptides can be inserted into the T7 E. coli expression vector pBT430. This vector is a derivative of pET-3a (Rosenberg et al. (1987) Gene 56:125-135) which employs the bacteriophage T7 RNA polymerase/T7 promoter system. Plasmid pBT430 is constructed by first destroying the EcoRI and HindIII sites in pET-3a at their original positions. An oligonucleotide adaptor containing EcoRI and Hind III sites is inserted at the BamHI site of pET-3a. This creates pET-3aM with additional unique cloning sites for insertion of genes into the expression vector. Then, the NdeI site at the position of translation initiation is converted to an NcoI site using oligonucleotide-directed mutagenesis. The DNA sequence of pET-3aM in this region, 5'-CATATGG, is converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 µg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 µL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25° C. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 9

RAMOSA3 Protein—In Vitro

Trehalose-6-Phosphate Phosphatase Activity

Protein expression and in vitro phosphatase assays. To produce recombinant proteins for in vitro phosphatase assays, E. coli expression vectors were constructed containing polynucleotides encoding either the RA3 full-length protein, the RA3 TPP-domain fragment or the RA3 N-terminal fragment. DNA fragments encoding either the RA3 full-length protein, the RA3 TPP-domain fragment or the RA3 N-terminal fragment were amplified, respectively, using the following primer pairs:

```
RA3 Full-Length Protein:
NS487 (SEQ ID NO:56):
CGAGCCATGACGAAGCAC
and
NS429 (SEQ ID NO:57):
ATAAGCGCCTCTTTGCTGTTG;

RA3 TPP-Domain Fragment:
NS483 (SEQ ID NO:58):
GGCGACTGGATGGAGAAGCA
and
NS429 (SEQ ID NO:57):
ATAAGCGCCTCTTTGCTGTTG.

RA3 N-Terminal Fragment:
NS485 (SEQ ID NO:59):
GTGCGCGGATCCAGCCATGACGAAGCACGCCGCCTACTC
and
N5488 (SEQ ID NO:60):
CTTCTCGAATTCTCAGCCGTGCTCGGCGTCGGCG.
```

PCR fragments were cloned into the vector pCR T7/NT-TOPO, which introduces an N-terminal histidine tag into the recombinant protein (Invitrogen). His-tagged recombinant proteins were expressed in E. coli and purified by a batch purification method (Qiagen). The proteins were used at a concentration of 70 ng/µl for phosphatase assays using sugar phosphates (Sigma) at a concentration of 2 mM, or ser/thr phosphopeptide as described (Klutts, S. et al. "Purification, cloning, expression, and properties of mycobacterial trehalose-phosphate phosphatase" J Biol Chem 278:2093-2100 (2003)). Sugar phosphate phosphatase activity was measured using the following four sugar phosphates: trehalose-6-phosphate, glucose-6-phosphate, fructose-6-phosphate and sucrose-6-phosphate. Phosphate release was measured as $OD_{600}$ (serine/threonine phosphatase assay system, Promega).

His-tagged RA3 full-length protein (SEQ ID NO:61), His-tagged RA3 TPP-domain fragment (SEQ ID NO:62) and the His-tagged Mycobacterium tuberculosis trehalose-6-phosphate phosphatase (Edavana et al., Arch Biochem Biophys 426:250-257 (2004)) each catalyzed phosphate release from trehalose-6-phosphate (T6P) but not from the other sugar phosphates or the ser/thr phosphopeptide used as a reporter of protein phosphatase activity (FIG. 9). The His-tagged RA3 N-terminal fragment (SEQ ID NO:63) had no phosphatase activity and the non-specific phosphatase, shrimp alkaline phosphatase (SAP; Roche Applied Science), showed phosphatase activity against all substrates (FIG. 9).

This in vitro activity data supports the assignment of T6P phosphatase activity to the RA3 protein.

The His-tagged RA3 TPP-domain fragment (SEQ ID NO:62) consists of a 35-aa N-terminal region that contains six consecutive histidine residues, followed by amino acid residues 78-361 of the RA3 protein (SEQ ID NO:19). The in vitro activity data (FIG. 9) indicates that amino acid residues 78-361 of the RA3 protein are sufficient to convey T6P phosphatase activity.

Example 10

RAMOSA3 Protein—In Vivo

Trehalose-6-Phosphate Phosphatase Activity

Complementation of yeast tps2 mutant: To complement a yeast mutant deficient in trehalose-6-phosphate phosphatase, DNA fragments encoding RA3 full-length protein and RA3 TPP-domain fragment each were cloned into a yeast expression vector. DNA fragments encoding either the RA3 full-length protein or the RA3 TPP-domain fragment were amplified, respectively, using the following primer pairs:

```
RA3 Full-Length Protein:
NS489 (SEQ ID NO:64):
AAGGAAAAAAGCGGCCGCGCCATGACGAAGCACGCCGCCTACTC
and
NS490 (SEQ ID NO:65):
ACGAGGTCGTGCCTGCCGCTCATGGTTGGCGCGCCCCCTTCT;
or RA3 TPP-Domain Fragment:
NS490 (SEQ ID NO:65):
ACGAGGTCGTGCCTGCCGCTCATGGTTGGCGCGCCCCCTTCT
and
NS500 (SEQ ID NO:66):
CGCGCCGCCGGCGGCCGCGACATGGACTGGATGGAGAAGCACCCGTC.
```

The DNA fragments encoding RA3 full-length protein and the RA3 TPP-domain fragment were cloned into a yeast shuttle vector, pFL6, in which high-level expression is driven by the phosphoglycerate kinase promoter (Minet, M., Dufour, M. E. & Lacroute, F. "Complementation of *Saccharomyces cerevisiae* auxotrophic mutants by *Arabidopsis thaliana* cDNAs" Plant J 2:417-422 (1992)). The *Arabidopsis* TPPB gene was used as a positive control. The empty yeast vector transformed into the yeast mutant served as a negative control. The constructs were transformed into the yeast strain YSH6.106.-8C, which has a deletion of the tps2 gene and hence lacks TPP activity. This mutant strain is sensitive to high temperature and salt concentrations (De Virgilio, C. et al. "Disruption of TPS2, the gene encoding the 100-kDa subunit of the trehalose-6-phosphate synthase/phosphatase complex in *Saccharomyces cerevisiae*, causes accumulation of trehalose-6-phosphate and loss of trehalose-6-phosphate phosphatase activity" *Eur. J. Biochem* 212: 315-323 (1993)). The yeast TPP mutant grows normally at 30° C., but has very slow growth at elevated temperature (40° C.), especially in the presence of an osmotic stress such as 1 M NaCl. Transformed cells were assayed for growth on selective media at 40.5° C., the non-permissive temperature, in the presence of 1 M NaCl, as well as at 30° C.

RA3 full-length protein (SEQ ID NO:19) and RA3 TPP-domain fragment (SEQ ID NO:68) each rescued growth at the non-permissive temperature (FIG. 10). Consequently, RA3 protein functions as a T6P phosphatase in vivo.

The RA3 TPP-domain fragment (SEQ ID NO:68) expressed in the yeast mutant consists of a start methionine residue followed by amino acid residues 79-361 of the RA3 protein (SEQ ID NO:19). The data in FIG. 10 indicates that amino acid residues 79-361 of the RA3 protein are sufficient to convey T6P phosphatase activity in vivo.

The invention claimed is:

1. An isolated polynucleotide comprising:
   (a) a nucleic acid sequence encoding a polypeptide having trehalose-6-phosphate phosphatase activity, wherein the polypeptide has an amino acid sequence of at least 90% sequence identity, based on the Clustal V method of alignment, when compared to SEQ ID NO:19; or
   (b) a complement of the nucleotide sequence, wherein the complement and the nucleotide sequence consist of the same number of nucleotides and are 100% complementary.

2. A recombinant DNA construct comprising the polynucleotide of claim 1 operably linked to a promoter that is functional in a plant.

3. A method for altering trehalose-6-phosphate phosphatase activity in a plant, comprising:

(a) introducing into a regenerable plant cell the recombinant DNA construct of claim 2 to produce a transformed plant cell; and
   (b) regenerating a transgenic plant from said transformed plant cell, wherein said transgenic plant comprises in its genome said recombinant DNA construct wherein said polynucleotide is expressed and wherein said transgenic plant exhibits an alteration in trehalose-6-phosphate phosphatase activity, when compared to a control plant not expressing said recombinant DNA construct.

4. The method of claim 3, further comprising (c) obtaining a progeny plant from said transgenic plant, wherein said progeny plant comprises in its genome the recombinant DNA construct.

5. The method of claim 3, wherein the transgenic plant exhibits an increase in trehalose-6-phosphate phosphatase activity.

6. The polynucleotide of claim 1, wherein the amino acid sequence of the polypeptide has at least 95% sequence identity, based on the Clustal V method of alignment, when compared to SEQ ID NO:19.

7. The polynucleotide of claim 1 wherein the amino acid sequence of the polypeptide comprises SEQ ID NO:19.

8. The polynucleotide of claim 1 wherein the nucleotide sequence comprises SEQ ID NO:18.

* * * * *

SEQUENCE LISTING

<160> NUMBER OF SEQ ID NOS: 71

<210> SEQ ID NO 1
<211> LENGTH: 23
<212> TYPE: DNA
<213> ORGANISM: Artificial
<220> FEATURE:
<223> OTHER INFORMATION: csu597 forward primer

<400> SEQUENCE: 1
attgcagaga ggctcaggaa gag                                          23

<210> SEQ ID NO 2
<211> LENGTH: 23
<212> TYPE: DNA
<213> ORGANISM: Artificial
<220> FEATURE:
<223> OTHER INFORMATION: csu597 reverse primer

<400> SEQUENCE: 2
gctactgtct tccacaacgc aac                                          23

<210> SEQ ID NO 3
<211> LENGTH: 24

```
<212> TYPE: DNA
<213> ORGANISM: Artificial
<220> FEATURE:
<223> OTHER INFORMATION: umc1412 forward primer

<400> SEQUENCE: 3
gcatctgtag ccttttttgtg tgtg                                      24

<210> SEQ ID NO 4
<211> LENGTH: 22
<212> TYPE: DNA
<213> ORGANISM: Artificial
<220> FEATURE:
<223> OTHER INFORMATION: umc1412 reverse primer

<400> SEQUENCE: 4
ctcagcttgc aggttatcgc tt                                         22

<210> SEQ ID NO 5
<211> LENGTH: 23
<212> TYPE: DNA
<213> ORGANISM: Artificial
<220> FEATURE:
<223> OTHER INFORMATION: a14 forward primer

<400> SEQUENCE: 5
atttgctttg gagagaggag atc                                        23

<210> SEQ ID NO 6
<211> LENGTH: 23
<212> TYPE: DNA
<213> ORGANISM: Artificial
<220> FEATURE:
<223> OTHER INFORMATION: a14 reverse primer

<400> SEQUENCE: 6
aagaggtccc tgtacacagc ttg                                        23

<210> SEQ ID NO 7
<211> LENGTH: 23
<212> TYPE: DNA
<213> ORGANISM: Artificial
<220> FEATURE:
<223> OTHER INFORMATION: n20 forward primer

<400> SEQUENCE: 7
gatcctcagc tttaagtgac ctc                                        23

<210> SEQ ID NO 8
<211> LENGTH: 24
<212> TYPE: DNA
<213> ORGANISM: Artificial
<220> FEATURE:
<223> OTHER INFORMATION: n20 reverse primer

<400> SEQUENCE: 8
tctcgttgca gagataccat acca                                       24

<210> SEQ ID NO 9
<211> LENGTH: 22
<212> TYPE: DNA
<213> ORGANISM: Artificial
<220> FEATURE:
<223> OTHER INFORMATION: cb.g1E forward primer

<400> SEQUENCE: 9
```

```
gtgctgtggt ccttcaattc tg                                              22

<210> SEQ ID NO 10
<211> LENGTH: 20
<212> TYPE: DNA
<213> ORGANISM: Artificial
<220> FEATURE:
<223> OTHER INFORMATION: cb.g1E reverse primer

<400> SEQUENCE: 10
gcgcagatca cggctcccat                                                 20

<210> SEQ ID NO 11
<211> LENGTH: 21
<212> TYPE: DNA
<213> ORGANISM: Artificial
<220> FEATURE:
<223> OTHER INFORMATION: NS346 primer

<400> SEQUENCE: 11
aagcagccca agaacaaca a                                                21

<210> SEQ ID NO 12
<211> LENGTH: 21
<212> TYPE: DNA
<213> ORGANISM: Artificial
<220> FEATURE:
<223> OTHER INFORMATION: NS347 primer

<400> SEQUENCE: 12
cttttgcatc gggaagaagt g                                               21

<210> SEQ ID NO 13
<211> LENGTH: 21
<212> TYPE: DNA
<213> ORGANISM: Artificial
<220> FEATURE:
<223> OTHER INFORMATION: NS362 primer

<400> SEQUENCE: 13
acgtgtagcc acacacagtc g                                               21

<210> SEQ ID NO 14
<211> LENGTH: 21
<212> TYPE: DNA
<213> ORGANISM: Artificial
<220> FEATURE:
<223> OTHER INFORMATION: NS363 primer

<400> SEQUENCE: 14
gcaacgacat acaccacgag a                                               21

<210> SEQ ID NO 15
<211> LENGTH: 14753
<212> TYPE: DNA
<213> ORGANISM: Zea mays
<220> FEATURE:
<221> NAME/KEY: misc_feature
<222> LOCATION: (834)..(873)
<223> OTHER INFORMATION: n is a, c, g, or t
<220> FEATURE:
<221> NAME/KEY: misc_feature
<222> LOCATION: (11666)..(11705)
<223> OTHER INFORMATION: n is a, c, g, or t

<400> SEQUENCE: 15
aaaagcagta aatgccaacc aacagcgtag ggccacccgc tttatataga cgacggggcg     60
```

-continued

```
cataagtcga ggggtgatgt catttcttgc tcactgtggt gtggaccaaa agatgcaatc      120
cttatttctg aagctctata atctttatca ttttcaataa caatctccag ggatgtgttt      180
ttcggacctt cagcgcagtg cctcccttga ttattttga agtttgagct cgttgtgaga       240
agtgaactaa ttttgcgagg tactactatt gggggccctc atagccaaag gtcctcgaaa      300
tattatacta ataggtgaac atacctctaa tatagtctac aggtaaaaat gcttcagctt      360
cttcggaatc aacacataag gaagcgacga agttaaaagc ttatgcttca ttgggtcggt     420
tgataagttg atacgaaggg gagaggaagc ttcgtctcca aagcatcaac acacaaaaca     480
gaaggagtcg agaagattcc agaaggttgg ttgtcatggt tcaagaaaaa agtcgatatt     540
aaccttaaaa gagttgtagc tcacatgtat aggatctaag gcatgaatg taattttata       600 cgaagctgta tctcaccact ataaatagga gcacaatgcc atgcatatgg acacttttgg      660
agtcggtgaa agacatcaat agctcatact ttgaagctat tctattttg cctttgtgta      720 tctagcttag caagatcgaa ggtatacaga caaaatgtct attgtatcat gtaattcaga     780
acaacaaaag gtaaattgat ctcgactaaa ttaatttgtt gaattatcat tatnnnnnnn     840
nnnnnnnnnn nnnnnnnnnn nnnnnnnnnn nnntaggggg ccatgttgct tgatgccaag      900
aggcgcaaag aggcgccaaa ggcatatact gtggcgtgtc gtagggtgtg agtggcctag     960
gagcatcatt tctcaggtgt gtcgagacat aggaatgacc tagaggttgg actcgtgggt     1020
ggcccgaggc acaaggggcc ctagatctta cttatgtatg tgttgtcatg tgttctagca    1080
agctaatcta ggaatacct tgtatgggcc aaatgtagtg tataagtctt acatttttg     1140 aggtcgatga aggccctatg gtcataaagt cccaagagcg gtgacccttc catcgtgggt    1200
cctagagtca atttctttgg gagggattat tcggcacttc ttggtagcag ccgtggtata    1260
accttaccta ggagctaacg gtaagataac atatctacta atgattcaat attatatgtg    1320
gttctatgag gtgaccaat gaaatggcac acaccatctg tgtcagcttc aattatatat     1380
taacaatcaa ttttgctatt tgatatgata tttctttaat attttatac ttaaatctca     1440 accacgaagt ttttaattgt atttaactaa aatcagtcag taatctttcg atgatcaaag     1500
gtaaccaact aagaaggtta cttgcaagga accatgacac ttgtaatggt ggttgtaaat    1560
acagatacta catcatcatc tgcccataag gtattctaga atacttagcg cagtttacat    1620
gcaacatgtg agtacatatg gtggttatgt aggagacaca actggttgct acatggcaac    1680
ttcaacaatt tgttcagtta ttcatgcatc aaaaactatt gtcattccat caccgcaatt    1740
tggttggcct aggtagttat tcagagcttc tagtattctc actttaaaat catcaatgaa    1800
cacatacata tagcttgttg tactcataaa actatagcgt aaagcaatat atctactgct    1860
cattcaagaa tatatgtggt tttataaaga tggaccaatt aaaggtgcac tcaatctatg    1920
tcatctatgg tgaaaaggtg aaacttctat atatattaac aaccaatttt gctacatgat    1980
acgatatctg taataataat tttatactta attatgcacc gctatatttt taaattatat    2040
ctttatctaa aaccgaaagc ttttccgtga ttaatggtaa ccggtataga aggttgctta    2100
aaaggaacca caacacttgg catggcagta gtaaatatag gcactatacc attgtctggc    2160
cacaaaggta ctttagcaca ctccgcatat ctttcgtaca atgtgttgat acatatggtg    2220
gatatctaga ggacattgct tgttgttaca tcacaacttc aacaattata gtcattcatg    2280
catcagaaat cactggcatt ccttcaccac aatttgtttg gcccaagtaa cttattaata   2340
gcttttggta tcccccctct ctaaaatcac taatgataac atacacatag cttgatttac    2400
```

```
tcatgaaact atagcataaa gtaatctatc tagtgcccat tgaagaatat acgtggttct    2460
atggagatga accgatgaaa cgcgcactca agctatgtta tcttcggtgc gaaggcacaa    2520
cttctatatt gacatccaat tttgctatct gatatggtat ctctaataat attttttatac   2580 gtaaatatcc gccgttaaat ctgcaccgct atgttttat aattatattt atttgaaacc     2640
gaaagctttt ccgtgattaa tggtaaccgg ctaaaaagat tacttataag aaagcttaag    2700
atctttaaca tgaatgaatg ccatacatca aggatactat gccatcctat atatgtccac    2760
aaatatactc tagcatgacg gtaatataat gggatatata taccctcata aatcatggat    2820
actatttgta aggactttgg tatttgtaca gtcattcatg catcagaaac tactaaaaag    2880
caaaatgaaa agttaatcta tgtagatttt gcattgcatt cccctcaacc aagcaagcat    2940
ccagaggaac gaaggacaaa tgttattcaa ttttgtattg cttccctc aaccaagcaa      3000 gcagcccaaa gaacaacaaa tggcattccc atgagagaaa aaaaaatac ttgtaggtgg     3060 ggccaccctc ccctacctat atatacccct gttcacgccg ttcccaagac cacaccacca    3120
gtccatccat cctgcgctgc gctgcgctcg tgacaagcat cgcaagcagc tcctcctcct    3180 cccctgtag ccaacacctt cctgttccgg gcgcagtagc ggctgtcggc cctcgatctg     3240
acgagccatg acgaagcacg ccgcctactc cagcgaggac gtggtcgcgg ccgtggcggc    3300
gccggcgccg gccggccggc atttcacgtc gttccaggcg ctgaagggcg cgcccctcga    3360
ctgcaagaag cacgccgccg tggacctgtc cgcgtccggg gcggccgtcg tgggcggcgg    3420
cccctggttt gagtccatga aggcttcgtc gccgcggcgc gccgccgacg ccgagcacgg    3480
cgactggatg gtatgtactg tactgtactc ccggccgcgc gtcttctctc tctctttctc    3540
tctatctgtc tgcacctgca cgcgacgaga tcgatcggcc cgcgcctcac tttccgtctg    3600
caggagaagc acccgtccgc attggcccag ttcgagccgc tgcttgccgc cgccaagggg    3660
aagcagatcg tgatgttcct ggactacgac ggcaccctgt caccgatcgt cgaggacccc    3720
gaccgcgccg tcatgtcgga ggaggtcagc gagcaaccct cgccccccgg gccgttttct    3780
cacttcttcc cgatgcaaaa gattccattt ttcttttctg ttctatttta gttaaaaata    3840
aattaacgga cgataaatat tcggagttat aacaatataa agaaatgaa aagaaaaaaa     3900 agttgctctt ttcctactat ggcagtagca gagcatgctc tgttcgtttt cgttttcgtt    3960
ccctggaact gtcggtccct gtgtttacct taacctgctg ctgtaattaa tatatatagt    4020
aaccgaatga cggacccccc ccccccccc ctctgtgatt tgatttcctc tgtggcctcg     4080
ctcagatgag agaagccgtg cggcgcgtcg ccgagcactc cccaccgcg attgtgagcg     4140 gaagatgcag ggacaaggta cattattccg attcggatcc cgtcaactcc tctccgttcc    4200
gttctttctt ttcgctgctt caaattatta ctgtgtccat ctctgtatgt tgaagaagaa    4260
tgtgtggtgt ggactcggcc ttggcgcctt gtagttgcac gctgtatagc ccgcgcttcc    4320
ttgcacacac acgacacgag ctagaaaagg aatcttccag gtttcctttt tctacccggc    4380 gagtttaaa atctcacctc actcactcac gcgtccgtaa daccgtgacg gcgtctggct     4440
gtgcgatcgg accggacgga gccacggagg aggaggagga ggaggaggag gaggaggag     4500 aggaggagga gggagggagc tgatgagaag cgcgggcgtc tgcttttgtt ttgtttctca    4560
tctaggcttc gctcgctcgc ctccttgcac cttttctcct gccgttcttt ctttttttct    4620
ctttattatt tgtctgcacc cgctgcggct acctttcttt ccttcttctg cgagtccgca    4680
cgcctttagt tttgtttgct agtagctagt agtagcactc tgggaaagcg gcagtagtag    4740
tacgtaacgt acctgggga agtggagtgg tgtatttatg gccatggcct tggtgcaatt    4800
```

```
tataggtgct caacttcgtg aagctgacgg agctgtacta cgccgggagc catggcatgg      4860
acatccaggg ccccgccgcc tgcaggcagc ccaaccacgt ccagcaggca atgtttccc       4920 tctcacatgc atgatgcatt gtcgatcgta accccttga ctgactgacc ttcaggtcgt       4980
acacacgcag gctgaagccg cagctgtcca ttaccaagct gcgagtgagt cctgccggt       5040 catcgaaagg gtaactaaac tccatgcaac tatatacgca agcatctata tatatatccg      5100
tcgtcgatcg tccgtcttca tcagatcgtt tatatattgc catgcaggtg ttccgcacgc      5160
tgacggccaa gatggagtcc atcgccggcg ccagggtgga gcacaacaag tactgcctgt      5220
ccgtccactt ccgctgcgtc cgggaggagg tatatatatg tatagatcaa ttatattatt      5280
ctgtgccggc cgggcctgtt gatttctttt tagttattat tcatacacac gttggattca      5340
cctcggcagg aatggaatgc cgtgaacgag gaggtcaggt cggtgctcag ggagtacccg      5400
aacctcaagc tcactcacgg cagaaaggtg aggaggcatc gtacgtacgt atcgatcaca      5460
tcagatgata tatatggatc ggaataatat tagtattatg ctcagtcctg ctgtatatta      5520
gttccccgcc tcccgatcga tcgatcgatc gatccagcag aatatcattg agcaactagt      5580
agtaccagta gtttattata ctcactccgt tctttttat ttattgcgtt ttagttcaaa       5640
aatgaacgac aaatattcga gaacggctca tatcttcgca aaacaaaact ttctttcaga      5700
caaaacatga cggtgcatgc agtagtgtga gcacgtactt aatttattta tgttttataa     5760
tggaataaga aattgtatat actatatata tactagtaaa attagctagg ttgcctatta      5820
tcagcagtga gctagctagc aagacaaatt aaagcagcag gtcggtggtg gtggcggtgg      5880
cgaccttgtc gtgttctcgc tcgtcgtgct ggtagctcta gagagtacga cgtgcatgca      5940
tgcacaagca caggggcgca gtgatagatg gtgataatgc atgctcacgc acactagtgc      6000
cttcttctca tatgcatata tgcaggtgct ggagattcgt ccgtccatca agtgggacaa      6060
gggcaaggcc ctcgagttct tgctcaagtc tcttggtaga tctctctctc tctctctatc      6120
tgcaaaccaa ataaactata tgcgcacaca catatatggt gcacatgtat atatactagt      6180
attcttaacc atttgaactt ttgttttttc aggctatgct gggcgcaacg acgtcttccc      6240
gatttacatc ggagatgatc gcactgacga ggacgctttc aaggtaaaaa ataaaaaaag      6300
aagctagcag aaaaggtagat agtaggaaat taacttcgtg ttggaaaatg aaaagagaga    6360
agctataggt gagctaataa actctcttgt cgccatgctg taggtgctcc gcaacatggg      6420
gcagggcatc ggaatcctgg tgtccaagct tcctaaggag acggcggcat cctactcgct      6480
gagtgaccct gccgaggtaa gaatctccac gtccgaaaac gataccggcc ggccgtctgt      6540
gtttgtctat aggggatcgg aacctcatca cttgtgacgg tgactactgc caactagcta      6600
agctagaaag ctagaccagt cacatctaga caatcttttt cgttacccat gcatatgctt      6660
tatttgttgt tgggtaattg atgggtttga taatgattaa ctctcgcgag accaaagcta      6720
gctggttgtt gacgtgcttg tggattaatt attaaccgat cgttttacg tacgtgtggt      6780 gttttatcat gacgtgtgtg taggtcaagg agttcctccg caagctggcc ataagaagg      6840 gggcgcgcca accatgaaaa tgaagacgac ctcgtgcatg catgtagcta agctaggcat      6900
ggcgtggacg atggatggat ggacgagcac aacagcaaag aggcgcttat tagctacaac      6960
tactggcctt ttttgttgtt ttcttttgc tcctacctat gcatagatag tagtctctac      7020
tctctactct ctacctagca acaacaacaa cctagctgat gcgcgcatgc atgcatgcat      7080
tggtcgtcgc ttactacatg catggccatt cagtgcagtg cgtgtgtgcg atggcggaga      7140
```

| | |
|---|---|
| aacaacctag ctagctagct gctcgatcga tcgatcggcc ttgtcttgga agaaggcggc | 7200 |
| agggaggggg tccctgtgta actgctgggg atccgatata tcgatctgtc cttccggccg | 7260 |
| gcaagatctt gtaattagcc gctgtggtac tagctagcag ctagagagaa atggataaca | 7320 |
| aaacaaataa catgcgtcgt cgtcttcgtc tccgttcatt ctcgtccctc tggatcctag | 7380 |
| agcctgtatg tacatgcgtg gtcagacgac ggtcgatctg ttggcaacgc gcgcagcagt | 7440 |
| ctagctagct agtctgtgtg tgtgtgtgtg taggtggtgg gcacgcctgc ctatgcacag | 7500 |
| atgacacgac gtacgtacac gtacacgtat tgatgctgct ggatcgatat cgcaattact | 7560 |
| ttggttggtg cggcaaacct gaaaaccagc agtggggagg tggtggaagg aaaggaaccg | 7620 |
| aaagaacacg atgcacagtg cgtgcgcagt ttggagtgga ccagctctag ccaggtggta | 7680 |
| gcggctgctt gcattgcttg ttgtaaatgc agcatgcacc tgtgtgtcag aagcatgcat | 7740 |
| gcgggagtcg tcggagtgag tcagcaggcc ggtcgatcgg tcgccctgcc ggcacgagcg | 7800 |
| aggtagccta gccctgcgct gaatcatatc tccagataga tagatagata gatagataga | 7860 |
| cagattgtat tcaatgtaga gtttgcaatg ggtagctctg tggccggcta cctatctatc | 7920 |
| tatctatcta tctaccagct gaagatatat agtatgattc agcacaatat aatagcaacg | 7980 |
| acatacacca cgagagagag cgacaaaagt atttatcgtc agaaggcagg agaaaaaata | 8040 |
| tatttatcta tcggatgatc aattaattga tcgtcatgaa tagcgtggag ccaaaagaga | 8100 |
| tgtgggatat gctgcctggg agctagctaa gcatgcatgc ggtatgtagg ggtacaagtc | 8160 |
| cttggccagt agccgtgcca cctttgccgc aggcaggcag gcaggcaggc gcagcgtcgg | 8220 |
| gtcgggtcgg gtactgtggg tgaaaacggc aaggatccat gcacatggcc ccctgcgcat | 8280 |
| gcgccgggga cgccaacggt ggcgcgcagg ccggccgcgg ccgggcatga ttgaatgcgc | 8340 |
| gcacaggagc tagctagcga ggccctggca cgtaccggcc ggtgctgccg ctgcgccggg | 8400 |
| cgagcgctcc tcgccggccg cgcagcagtc gccttgttag cttttcgggg gccgcagact | 8460 |
| gagactgaga ctgcatgcgc gcggacggag ggagcgccag gccacatgcc ctctctgacc | 8520 |
| aggcgctgcc gccggccctc gctcggtcgg gcctctcccg tttccctgcc gctgcgtgca | 8580 |
| gcgattcggc gtatcagccg ccggagctgc tggaaccctg ctgcttactg gctacaggct | 8640 |
| gctcactgcg gtgcggtgca ggccggccgt tggaggtgat gaccacacaa catgtgggcc | 8700 |
| atgcatgcat ccatcaccca ttcggcacag tagtctcgct cgctcggaac gaagaatgca | 8760 |
| acgactgtgt gtggctacac gtccatatat atatatactc catgcaaatg gaactacaag | 8820 |
| aacgtttctg aaaatttatt tggttcatta acgatctctg ctgctcaaaa taaaatctct | 8880 |
| ttaactcgat ctgctgacca ccccacccca ctcgtaccaa ttaatataat acagactatg | 8940 |
| caaaatagat accatcagta gttttttaaa ttttcatgga atatatatac acagtacgtg | 9000 |
| taccataaat agttttcaat cttttttatta tacgtatttt gaaaccaagg ggttataaac | 9060 |
| acatgcatgc atatatcttt cccgccctca acatacacat gcatgcatat gcgtgtggcg | 9120 |
| tgcccgacaa tgacggtgtg tgtgggcggg atgggcaacc actggcaccc gtgcctctgg | 9180 |
| accaggagca tcgcggcgcg acagctaata taacatcacg cacgcaaggt acttttgatg | 9240 |
| cggccctcga actggtagca tagaaatata tatatgcttg ctgcagtgta ctcgtagatg | 9300 |
| cccttagccc ggaaagctca tcatcagtag tgtgtgtgct caagtctagc tagctagcgc | 9360 |
| acaacgaggc aagttaagcc acaccacagc tatagtatat attttgtagt ttaaagaagg | 9420 |
| aacaattaat agcacaggac cacagttagt caagcgagat cggtcttgag tgtcccagca | 9480 |
| gcagccacat acatagaaac cggccggact caacttggaa aagccaagca aggccacgta | 9540 |

```
gcagcagatc gacccgtacg cggttttacc aattccttat gcacgcagca gccctaaaga    9600
ttctctgctg ggtcatgtat gcattgcatg atcatactac atatatgtac tattacacat    9660
gtggactggt atatatacta gtcgtttaat tacatgcatg gcggggacct ggctaataat    9720
gccgatggct ttgctccatc tttttaccgg cgcacgcgtg gaaagatgca ggtggtggtg    9780
caagctaagt tgctttgtgc gcaaaagaat ctggcaccgg ccggcgccac cggcacatga    9840
cacactaccg gccgtcggcg gcgttggaat aattggccgg cgacgtcgac gatgccaaaa    9900
gacggcttcc cggccaacca cttaacctcg aataaaccct gcatgcagca gggaaagcac    9960
ggccgctttt gcaggttttc atacataata acaaatcatt ggcgtgtgat ctagctagca   10020
aggcgggtgg gggccgggca cagctagcta gcactaccag cccttgcgaa ttgaacaata   10080
acaaattcgc aaccaatatc tctctctctt taatttacct ctctcggctg atgaaccctg   10140
atatttttaa gcctgtcaca cttggaggct acaaggagag agatcacatg cgcgccagtc   10200
agggccgccc cacgcaagca agaagatcgc cacgcattgt aaagctagct ttggcggccg   10260
agatcctggt ataaagcatg caacaagtgc caaattaaaa gagcgcgtta ggctggccaa   10320
tgcagtggca tcatgcaagg cctggcacat gcatggtctc tctctctctc tctctctctc   10380
aaaggtaata ccgtggcttc tttagctcct agtagagctc acagtcacag cattattcag   10440
tgctgtggtc cttcaattct gttgcttgca ccaatactct actatggttt tgtactctgt   10500
atggttttct gtaatatcgg tcggcgtcgg cccgcgtagg cgtcacgcga gctgagatct   10560
cgctagctag ctctgcattg ttcctttcgg tgcgtggtgt tggattattg ggagccgtga   10620
tctgcgcgcg ctgtgctact tgttaagcta ggttaaagac gacacggccg gggatcgtat   10680
ctgcacgccc agatttgatc ctattttgtt tgaccattca ccttttttgta gtacgagtat   10740 atttctattc tattctctag ggtttaattt tgcttgacag catgcatgca gtttccacat   10800
tccacacact gtatgtagaa ttctagagtc ctttaatttg caatagtgta gtgtaggtag   10860
atgctatgaa taattttcta ccagtaggca gtatgtgtgg tagtttaggt cggggctctg   10920
cctatgtgta cgtgtatata ttaatatgta tattggaaaa tcaaaatcat atatattata   10980
tagagcccag tgctcttaat agataaacta tatatatata tatatatata tatatatata   11040
tatatatata tatatatata tatatatata tatatatata tatccttttt cttggaagaa   11100
aaaaagtaga taatgattca taaatgcagc aatttacttt gtccattcaa gcaacaagca   11160
ccttcttcga aaacttttga tggaacgaag ccatgcatgt tctacgtgat tcaaagccaa   11220
taagcaagga ttgatacagt actactgtgc accaccctgc agtgccacag tctctagcta   11280
cgacgaaaga tcgaaggaaa ggtgaggctg ctgaggcaca ccatgcatat gcatcttctt   11340
cattcatgga gagagagaga gagagagaga gactactgac acgtatggag tggaacaaca   11400
gtggctggcc ggctagcatg cgccctcgtc ggtgggcatc gcgtcgtcgt ccaactgttg   11460
ctgcaggcgc gcgcgggcgc ttcggccggc atgcgtgcgt gtctcgctgc tccctccccc   11520
atgatgctac gcacgcagac ggccggagga gatcagaggt cctaccgatg aacaaagcgt   11580
gcgatcgacc atatggcctc ttgcccccac acgtttgctg ttcttggctt ctggcagaaa   11640
atggctagct agtgacaacc agcgcnnnnn nnnnnnnnnn nnnnnnnnnn nnnnnnnnnn   11700 nnnngtgta ggtagatgct atgaataatt ttctaccagt aggcagtatg tgtggtagtt   11760
taggtcgggg ctctgcctat gtgtacgtgt atatattaat atgtatattg gaaaatcaaa   11820
atcatatata ttatatagag cccagtgctc ttaatagata aactatatat atatatatat   11880
```

-continued

```
atatatatat atccttttc ttggaagaaa aaaagtagat aatgattcat aaatgcagca    11940
atttactttg tccattcaag caacaagcac cttcttcgaa aacttttgat ggaacgaagc    12000
catgcatgtt ctacgtgatt caaagccaat aagcaaggat tgatacagta ctactgtgca    12060
ccaccctgca gtgccacagt ctctagctac gacgaaagat cgaaggaaag gtgaggctgc    12120
tgaggcacac catgcatatg catcttcttc attcatggag agagagagag agagagagag    12180
actactgaca cgtatggagt ggaacaacag tggctggccg gctagcatgc gccctcgtcg    12240
gtggcatcg cgtcgtcgtc caactgttgc tgcaggcgcg cgcgggcgct tcggccggca    12300
tgcgtgcgtg tctcgctgct ccctccccca tgatgctacg cacgcagacg gccggaggag    12360
atcagaggtc ctaccgatga acaaagcatg cgatcgacca tatggcctct gcccccaca    12420
cgtttgctgt tcttggcttc tggcagaaca atggctagct agtgacgacc agcgcgcgcg    12480
gcagctgaag catgcagcag tatcactgtc acatcatgac acagttaaaa ttctgcatac    12540
agaagttgtc tccccccccc ccccccctc agttattagc tggggtagct gttttgtttc    12600
atagttgcgc gtactatttt aatttaagca gacggcaaaa ctgtaaataa aatcgagtgc    12660
gtcttcggtt ctgtttcgta tagcctgtgg tgtatcggac ttcggacctc ctagaggccc    12720
gtactctgaa atgaggccca gcccacgtac aaggctacgc ctacacagta ggcaccatgc    12780
aacacataca cagtaaccca cttgtcacat cggcaccggt atcccacggt cccatgccac    12840
gttggcccag cgcccccggc cgcctccatc atcactagtt cgtcaccatt ctaggtactc    12900
cactaggtta tgtaaaatag gacacgccaa attgtagatg acacaatgtg acaatattat    12960
gcagagtaat gtttgaaata tgagatctga tagaagatag tcttagtgtt gataatatgg    13020
gccaaccttt ttggactagt gttggagcga aagtcgacca cccctcggtc agacttcttt    13080
aatatcaatc gaataggttt tgtcgcaggt atagaaagcg aagggtacct cgaccagtat    13140
cagaatcgag gtcttcgact ggagttgaca gagacgtcgg agcgaagggc cgcactgtta    13200
aaaggggc tcattgtagc ctcgcgaagg cgcccccatc gtcttggaca gttctgaacg    13260
acgacagtcc tggcgaggtc gaaggctcgg tttcgcagga cgaagggtgc cgcgcgcggg    13320
cgaaggccac gccacccaac ggtgggaccc aggccacgtt tcgtcgtcat ttgcgcccat    13380
ttgtaagccc ctcctcgcgg taggtttcgt agtgtgtcta atcaaattat acttatcatc    13440
actataatga ccatgtaagg aggaatattc tggagctgta gcaagtaacc aggggcccat    13500
gccacgttgg cccagcgccc tcggccgcct ccatcatcac taggtcatca ccattctagg    13560
tactccacta ggttatgtaa aataggacac accaagttgt agatgacacg acgtgacaat    13620
attttgcata gtaatgtttg aaatatgaga tgtgacagga gatagtctta gtgttgataa    13680
tataggccaa acttttggg ctagtgttgg agcgaaagtc gaccacccct cgatcagact    13740
tctttaatat caatcgaata ggttttgtcg caggtataga agcgaatgg tacctcgacc    13800
agtaccagaa tcgaggtctt cggccggagc tgccagagac gttggagcga aagaccgcac    13860
tattaaaaag gaggctcatt gtagcctcgc gaaggcgctc ccatcggctt ggacagttct    13920
gaaccatgac agtcatggca aggtcgaagg ctcggcttcg cagggcgaag ggtgccgtgc    13980
gcgggcgacc tctctggacg acgcaaaggc ggccatcgcc gagaaaaaaa ggcaagacaa    14040
tcctcgctga tgtcgccccc aagatgcacc cgaaaacaac gatgagccaa tcaacaacaa    14100
gtgtccccga accaagaacc cgccgacccc cgaaggcacc gttcacacat gcaattctga    14160
aggcctcccc caagctgacg acatcatcaa ggacagcgat gtcctatgca tctcagctga    14220
agaccagctc aaattacgag cacttcgtat aaaaaacaat catctataaa aatagaaaga    14280
```

-continued

```
gaacccgcgg ccaagaggta gcgaacaaat atgcaggcca agaaagacaa aattgctcaa    14340
gaagaggagc aaaaggctaa ggagctagag cagcaaatcg atgaaatgct gggcgaagac    14400
ctctgccacc agcaacgagc cgcaacactc aatctaaacc ttcgtctcct ccacgtacca    14460
accttcgcac tagctgcctt ccaagggcta aattaccttt tcgagtgaag ctctctctca    14520
ccacaacttt agacctcccc ttggccgcaa aattacaaag cagacactta ccccaagtag    14580
aacaacattg cagacccaac tcagtacatc atgagctatc aggtcgcaat cgcatcatct    14640
gggggacgac accactatgg ccaagccatt catcatagcc ctcaaggggc cagctctcac    14700
attttattca aggttgctgc cgttatcaat tgattcatgg aagactctcc gca           14753
```

```
<210> SEQ ID NO 16
<211> LENGTH: 21
<212> TYPE: DNA
<213> ORGANISM: Artificial
<220> FEATURE:
<223> OTHER INFORMATION: NS432 forward primer

<400> SEQUENCE: 16
tcgtgacaag catcgcaagc a                                                21

<210> SEQ ID NO 17
<211> LENGTH: 21
<212> TYPE: DNA
<213> ORGANISM: Artificial
<220> FEATURE:
<223> OTHER INFORMATION: NS411 reverse primer

<400> SEQUENCE: 17
gcgcatcagc taggttgttg t                                                21

<210> SEQ ID NO 18
<211> LENGTH: 1086
<212> TYPE: DNA
<213> ORGANISM: Zea mays
<220> FEATURE:
<221> NAME/KEY: CDS
<222> LOCATION: (1)..(1086)

<400> SEQUENCE: 18 atg acg aag cac gcc gcc tac tcc agc gag gac gtg gtc gcg gcc gtg     48
Met Thr Lys His Ala Ala Tyr Ser Ser Glu Asp Val Val Ala Ala Val
1               5                   10                  15 gcg gcg ccg gcg ccg gcc ggc cgg cat ttc acg tcg ttc cag gcg ctg     96
Ala Ala Pro Ala Pro Ala Gly Arg His Phe Thr Ser Phe Gln Ala Leu
            20                  25                  30 aag ggc gcg ccc ctc gac tgc aag aag cac gcc gcc gtg gac ctg tcc    144
Lys Gly Ala Pro Leu Asp Cys Lys Lys His Ala Ala Val Asp Leu Ser
        35                  40                  45 gcg tcc ggg gcg gcc gtc gtg ggc ggc ggc ccc tgg ttt gag tcc atg    192
Ala Ser Gly Ala Ala Val Val Gly Gly Gly Pro Trp Phe Glu Ser Met
    50                  55                  60 aag gct tcg tcg ccg cgg cgc gcc gcc gac gcc gag cac ggc gac tgg    240
Lys Ala Ser Ser Pro Arg Arg Ala Ala Asp Ala Glu His Gly Asp Trp
65                  70                  75                  80 atg gag aag cac ccg tcc gca ttg gcc cag ttc gag ccg ctg ctt gcc    288
Met Glu Lys His Pro Ser Ala Leu Ala Gln Phe Glu Pro Leu Leu Ala
                85                  90                  95 gcc gcc aag ggg aag cag atc gtg atg ttc ctg gac tac gac ggc acc    336
Ala Ala Lys Gly Lys Gln Ile Val Met Phe Leu Asp Tyr Asp Gly Thr
            100                 105                 110
```

```
ctg tca ccg atc gtc gag gac ccc gac cgc gcc gtc atg tcg gag gag      384
Leu Ser Pro Ile Val Glu Asp Pro Asp Arg Ala Val Met Ser Glu Glu
        115                 120                 125 atg aga gaa gcc gtg cgg cgc gtc gcc gag cac ttc ccc acc gcg att      432
Met Arg Glu Ala Val Arg Arg Val Ala Glu His Phe Pro Thr Ala Ile
130                 135                 140 gtg agc gga aga tgc agg gac aag gtg ctc aac ttc gtg aag ctg acg      480
Val Ser Gly Arg Cys Arg Asp Lys Val Leu Asn Phe Val Lys Leu Thr
145                 150                 155                 160 gag ctg tac tac gcc ggg agc cat ggc atg gac atc cag ggc ccc gcc      528
Glu Leu Tyr Tyr Ala Gly Ser His Gly Met Asp Ile Gln Gly Pro Ala
                165                 170                 175 gcc tgc agg cag ccc aac cac gtc cag cag gct gaa gcc gca gct gtc      576
Ala Cys Arg Gln Pro Asn His Val Gln Gln Ala Glu Ala Ala Ala Val
            180                 185                 190 cat tac caa gct gcg agt gag ttc ctg ccg gtc atc gaa gag gtg ttc      624
His Tyr Gln Ala Ala Ser Glu Phe Leu Pro Val Ile Glu Glu Val Phe
        195                 200                 205 cgc acg ctg acg gcc aag atg gag tcc atc gcc ggc gcc agg gtg gag      672
Arg Thr Leu Thr Ala Lys Met Glu Ser Ile Ala Gly Ala Arg Val Glu
210                 215                 220 cac aac aag tac tgc ctg tcc gtc cac ttc cgc tgc gtc cgg gag gag      720
His Asn Lys Tyr Cys Leu Ser Val His Phe Arg Cys Val Arg Glu Glu
225                 230                 235                 240 gaa tgg aat gcc gtg aac gag gag gtc agg tcg gtg ctc agg gag tac      768
Glu Trp Asn Ala Val Asn Glu Glu Val Arg Ser Val Leu Arg Glu Tyr
                245                 250                 255 ccg aac ctc aag ctc act cac ggc aga aag gtg ctg gag att cgt ccg      816
Pro Asn Leu Lys Leu Thr His Gly Arg Lys Val Leu Glu Ile Arg Pro
            260                 265                 270 tcc atc aag tgg gac aag ggc aag gcc ctc gag ttc ttg ctc aag tct      864
Ser Ile Lys Trp Asp Lys Gly Lys Ala Leu Glu Phe Leu Leu Lys Ser
        275                 280                 285 ctt ggc tat gct ggg cgc aac gac gtc ttc ccg att tac atc gga gat      912
Leu Gly Tyr Ala Gly Arg Asn Asp Val Phe Pro Ile Tyr Ile Gly Asp
290                 295                 300 gat cgc act gac gag gac gct ttc aag gtg ctc cgc aac atg ggg cag      960
Asp Arg Thr Asp Glu Asp Ala Phe Lys Val Leu Arg Asn Met Gly Gln
305                 310                 315                 320 ggc atc gga atc ctg gtg tcc aag ctt cct aag gag acg gcg gca tcc     1008
Gly Ile Gly Ile Leu Val Ser Lys Leu Pro Lys Glu Thr Ala Ala Ser
                325                 330                 335 tac tcg ctg agt gac cct gcc gag gtc aag gag ttc ctc cgc aag ctg     1056
Tyr Ser Leu Ser Asp Pro Ala Glu Val Lys Glu Phe Leu Arg Lys Leu
            340                 345                 350 gcc aat aag aag ggg gcg cgc caa cca tga                             1086
Ala Asn Lys Lys Gly Ala Arg Gln Pro
        355                 360

<210> SEQ ID NO 19
<211> LENGTH: 361
<212> TYPE: PRT
<213> ORGANISM: Zea mays

<400> SEQUENCE: 19

Met Thr Lys His Ala Ala Tyr Ser Ser Glu Asp Val Val Ala Ala Val
1               5                   10                  15

Ala Ala Pro Ala Pro Ala Gly Arg His Phe Thr Ser Phe Gln Ala Leu
            20                  25                  30
```

-continued

Lys Gly Ala Pro Leu Asp Cys Lys Lys His Ala Ala Val Asp Leu Ser
            35                  40                  45

Ala Ser Gly Ala Ala Val Val Gly Gly Pro Trp Phe Glu Ser Met
    50                  55                  60

Lys Ala Ser Ser Pro Arg Arg Ala Ala Asp Ala Glu His Gly Asp Trp
65                  70                  75                  80

Met Glu Lys His Pro Ser Ala Leu Ala Gln Phe Glu Pro Leu Leu Ala
                85                  90                  95

Ala Ala Lys Gly Lys Gln Ile Val Met Phe Leu Asp Tyr Asp Gly Thr
            100                 105                 110

Leu Ser Pro Ile Val Glu Asp Pro Asp Arg Ala Val Met Ser Glu Glu
            115                 120                 125

Met Arg Glu Ala Val Arg Arg Val Ala Glu His Phe Pro Thr Ala Ile
    130                 135                 140

Val Ser Gly Arg Cys Arg Asp Lys Val Leu Asn Phe Val Lys Leu Thr
145                 150                 155                 160

Glu Leu Tyr Tyr Ala Gly Ser His Gly Met Asp Ile Gln Gly Pro Ala
                165                 170                 175

Ala Cys Arg Gln Pro Asn His Val Gln Gln Ala Glu Ala Ala Ala Val
            180                 185                 190

His Tyr Gln Ala Ala Ser Glu Phe Leu Pro Val Ile Glu Glu Val Phe
        195                 200                 205

Arg Thr Leu Thr Ala Lys Met Glu Ser Ile Ala Gly Ala Arg Val Glu
    210                 215                 220

His Asn Lys Tyr Cys Leu Ser Val His Phe Arg Cys Val Arg Glu Glu
225                 230                 235                 240

Glu Trp Asn Ala Val Asn Glu Glu Val Arg Ser Val Leu Arg Glu Tyr
                245                 250                 255

Pro Asn Leu Lys Leu Thr His Gly Arg Lys Val Leu Glu Ile Arg Pro
            260                 265                 270

Ser Ile Lys Trp Asp Lys Gly Lys Ala Leu Glu Phe Leu Leu Lys Ser
    275                 280                 285

Leu Gly Tyr Ala Gly Arg Asn Asp Val Phe Pro Ile Tyr Ile Gly Asp
    290                 295                 300

Asp Arg Thr Asp Glu Asp Ala Phe Lys Val Leu Arg Asn Met Gly Gln
305                 310                 315                 320

Gly Ile Gly Ile Leu Val Ser Lys Leu Pro Lys Glu Thr Ala Ala Ser
                325                 330                 335

Tyr Ser Leu Ser Asp Pro Ala Glu Val Lys Glu Phe Leu Arg Lys Leu
            340                 345                 350

Ala Asn Lys Lys Gly Ala Arg Gln Pro
            355                 360

<210> SEQ ID NO 20
<211> LENGTH: 21
<212> TYPE: DNA
<213> ORGANISM: Artificial
<220> FEATURE:
<223> OTHER INFORMATION: 5' UTR-exon2 forward primer

<400> SEQUENCE: 20
aagcagccca agaacaaca a                                              21

<210> SEQ ID NO 21
<211> LENGTH: 21
<212> TYPE: DNA

```
<213> ORGANISM: Artificial
<220> FEATURE:
<223> OTHER INFORMATION: 5' UTR-exon2 reverse primer

<400> SEQUENCE: 21
cttttgcatc gggaagaagt g                                            21

<210> SEQ ID NO 22
<211> LENGTH: 22
<212> TYPE: DNA
<213> ORGANISM: Artificial
<220> FEATURE:
<223> OTHER INFORMATION: exon3-exon4 forward primer

<400> SEQUENCE: 22
actgtcggtc cctgtgttta cc                                           22

<210> SEQ ID NO 23
<211> LENGTH: 21
<212> TYPE: DNA
<213> ORGANISM: Artificial
<220> FEATURE:
<223> OTHER INFORMATION: exon3-exon4 reverse primer

<400> SEQUENCE: 23
ctgtcagtca aggggttac g                                             21

<210> SEQ ID NO 24
<211> LENGTH: 21
<212> TYPE: DNA
<213> ORGANISM: Artificial
<220> FEATURE:
<223> OTHER INFORMATION: exon5-exon7 forward primer

<400> SEQUENCE: 24
gcaccgtcat gttttgtctg a                                            21

<210> SEQ ID NO 25
<211> LENGTH: 21
<212> TYPE: DNA
<213> ORGANISM: Artificial
<220> FEATURE:
<223> OTHER INFORMATION: exon5-exon7 reverse primer

<400> SEQUENCE: 25
cgtaaccccc ttgactgact g                                            21

<210> SEQ ID NO 26
<211> LENGTH: 22
<212> TYPE: DNA
<213> ORGANISM: Artificial
<220> FEATURE:
<223> OTHER INFORMATION: exon8-exon10 forward primer

<400> SEQUENCE: 26
tcggacgtgg agattcttac ct                                           22

<210> SEQ ID NO 27
<211> LENGTH: 20
<212> TYPE: DNA
<213> ORGANISM: Artificial
<220> FEATURE:
<223> OTHER INFORMATION: exon8-exon10 reverse primer

<400> SEQUENCE: 27
cttgtcgtgt tctcgctcgt                                              20
```

<210> SEQ ID NO 28
<211> LENGTH: 21
<212> TYPE: DNA
<213> ORGANISM: Artificial
<220> FEATURE:
<223> OTHER INFORMATION: exon11-3' UTR forward primer

<400> SEQUENCE: 28
ggatcggaac ctcatcactt g                                              21

<210> SEQ ID NO 29
<211> LENGTH: 21
<212> TYPE: DNA
<213> ORGANISM: Artificial
<220> FEATURE:
<223> OTHER INFORMATION: exon11-3' UTR reverse primer

<400> SEQUENCE: 29
ggatccccag cagttacaca g                                              21

<210> SEQ ID NO 30
<211> LENGTH: 81
<212> TYPE: DNA
<213> ORGANISM: Zea mays

<400> SEQUENCE: 30
gaatggaatg ccgtgaacga ggagctaggt caggtcggtg ctcagggagt acccgaacct    60
caagctcact cacggcagaa a                                              81

<210> SEQ ID NO 31
<211> LENGTH: 305
<212> TYPE: PRT
<213> ORGANISM: Zea mays

<400> SEQUENCE: 31

Met Thr Lys His Ala Ala Tyr Ser Ser Glu Asp Val Val Ala Ala Val
1               5                   10                  15

Ala Ala Pro Ala Pro Ala Gly Arg His Phe Thr Ser Phe Gln Ala Leu
            20                  25                  30

Lys Gly Ala Pro Leu Asp Cys Lys Lys His Ala Val Asp Leu Ser
        35                  40                  45

Ala Ser Gly Ala Ala Val Val Gly Gly Gly Pro Trp Phe Glu Ser Met
    50                  55                  60

Lys Ala Ser Ser Pro Arg Arg Ala Ala Asp Ala Glu His Gly Asp Trp
65                  70                  75                  80

Met Glu Lys His Pro Ser Ala Leu Ala Gln Phe Glu Pro Leu Leu Ala
                85                  90                  95

Ala Ala Lys Gly Lys Gln Ile Val Met Phe Leu Asp Tyr Asp Gly Thr
            100                 105                 110

Leu Ser Pro Ile Val Glu Asp Pro Asp Arg Ala Val Met Ser Glu Glu
        115                 120                 125

Met Arg Glu Ala Val Arg Arg Val Ala Glu His Phe Pro Thr Ala Ile
    130                 135                 140

Val Ser Gly Arg Cys Arg Asp Lys Val Leu Asn Phe Val Lys Leu Thr
145                 150                 155                 160

Glu Leu Tyr Tyr Ala Gly Ser His Gly Met Asp Ile Gln Gly Pro Ala
                165                 170                 175

Ala Cys Arg Gln Pro Asn His Val Gln Gln Ala Glu Ala Ala Val

-continued

```
                    180                 185                 190
His Tyr Gln Ala Ala Ser Glu Phe Leu Pro Val Ile Glu Glu Val Phe
            195                 200                 205

Arg Thr Leu Thr Ala Lys Met Glu Ser Ile Ala Gly Ala Arg Val Glu
    210                 215                 220

His Asn Lys Tyr Cys Leu Ser Val His Phe Arg Cys Val Arg Glu Glu
225                 230                 235                 240

Glu Trp Asn Ala Val Asn Glu Leu Gly Gln Val Gly Ala Gln Gly
                245                 250                 255

Val Pro Glu Pro Gln Ala His Ser Arg Gln Lys Gly Ala Gly Asp Ser
            260                 265                 270

Ser Val His Gln Val Gly Gln Gly Gln Gly Pro Arg Val Leu Ala Gln
        275                 280                 285

Val Ser Trp Leu Cys Trp Ala Gln Arg Arg Leu Pro Asp Leu His Arg
    290                 295                 300

Arg
305

<210> SEQ ID NO 32
<211> LENGTH: 868
<212> TYPE: DNA
<213> ORGANISM: Zea mays
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t
<220> FEATURE:
<221> NAME/KEY: misc_feature
<222> LOCATION: (113)..(113)
<223> OTHER INFORMATION: n is a, c, g, or t
<220> FEATURE:
<221> NAME/KEY: misc_feature
<222> LOCATION: (124)..(124)
<223> OTHER INFORMATION: n is a, c, g, or t
<220> FEATURE:
<221> NAME/KEY: misc_feature
<222> LOCATION: (134)..(134)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
```

-continued

```
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (193)..(193)
<223> OTHER INFORMATION: n is a, c, g, or t
<220> FEATURE:
<221> NAME/KEY: misc_feature
<222> LOCATION: (214)..(214)
<223> OTHER INFORMATION: n is a, c, g, or t
<220> FEATURE:
<221> NAME/KEY: misc_feature
<222> LOCATION: (238)..(238)
<223> OTHER INFORMATION: n is a, c, g, or t
<220> FEATURE:
<221> NAME/KEY: misc_feature
<222> LOCATION: (242)..(242)
<223> OTHER INFORMATION: n is a, c, g, or t
<220> FEATURE:
<221> NAME/KEY: misc_feature
<222> LOCATION: (244)..(244)
<223> OTHER INFORMATION: n is a, c, g, or t
<220> FEATURE:
<221> NAME/KEY: misc_feature
<222> LOCATION: (269)..(269)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (311)..(311)
<223> OTHER INFORMATION: n is a, c, g, or t
<220> FEATURE:
<221> NAME/KEY: misc_feature
<222> LOCATION: (335)..(335)
<223> OTHER INFORMATION: n is a, c, g, or t
<220> FEATURE:
<221> NAME/KEY: misc_feature
<222> LOCATION: (338)..(338)
<223> OTHER INFORMATION: n is a, c, g, or t
<220> FEATURE:
<221> NAME/KEY: misc_feature
<222> LOCATION: (428)..(428)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (453)..(453)
<223> OTHER INFORMATION: n is a, c, g, or t
<220> FEATURE:
<221> NAME/KEY: misc_feature
<222> LOCATION: (467)..(467)
<223> OTHER INFORMATION: n is a, c, g, or t
<220> FEATURE:
<221> NAME/KEY: misc_feature
<222> LOCATION: (474)..(474)
<223> OTHER INFORMATION: n is a, c, g, or t
<220> FEATURE:
<221> NAME/KEY: misc_feature
<222> LOCATION: (476)..(476)
<223> OTHER INFORMATION: n is a, c, g, or t
<220> FEATURE:
<221> NAME/KEY: misc_feature
<222> LOCATION: (489)..(489)
```

```
<223> OTHER INFORMATION: n is a, c, g, or t
<220> FEATURE:
<221> NAME/KEY: misc_feature
<222> LOCATION: (496)..(496)
<223> OTHER INFORMATION: n is a, c, g, or t
<220> FEATURE:
<221> NAME/KEY: misc_feature
<222> LOCATION: (499)..(499)
<223> OTHER INFORMATION: n is a, c, g, or t
<220> FEATURE:
<221> NAME/KEY: misc_feature
<222> LOCATION: (517)..(517)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (589)..(589)
<223> OTHER INFORMATION: n is a, c, g, or t
<220> FEATURE:
<221> NAME/KEY: misc_feature
<222> LOCATION: (771)..(772)
<223> OTHER INFORMATION: n is a, c, g, or t
<220> FEATURE:
<221> NAME/KEY: misc_feature
<222> LOCATION: (779)..(779)
<223> OTHER INFORMATION: n is a, c, g, or t
<220> FEATURE:
<221> NAME/KEY: misc_feature
<222> LOCATION: (786)..(786)
<223> OTHER INFORMATION: n is a, c, g, or t
<220> FEATURE:
<221> NAME/KEY: misc_feature
<222> LOCATION: (796)..(796)
<223> OTHER INFORMATION: n is a, c, g, or t
<220> FEATURE:
<221> NAME/KEY: misc_feature
<222> LOCATION: (801)..(801)
<223> OTHER INFORMATION: n is a, c, g, or t
<220> FEATURE:
<221> NAME/KEY: misc_feature
<222> LOCATION: (805)..(805)
<223> OTHER INFORMATION: n is a, c, g, or t
<220> FEATURE:
<221> NAME/KEY: misc_feature
<222> LOCATION: (808)..(808)
<223> OTHER INFORMATION: n is a, c, g, or t
<220> FEATURE:
<221> NAME/KEY: misc_feature
<222> LOCATION: (810)..(810)
<223> OTHER INFORMATION: n is a, c, g, or t
<220> FEATURE:
<221> NAME/KEY: misc_feature
<222> LOCATION: (812)..(812)
<223> OTHER INFORMATION: n is a, c, g, or t
<220> FEATURE:
<221> NAME/KEY: misc_feature
<222> LOCATION: (816)..(816)
<223> OTHER INFORMATION: n is a, c, g, or t
<220> FEATURE:
<221> NAME/KEY: misc_feature
<222> LOCATION: (825)..(825)
<223> OTHER INFORMATION: n is a, c, g, or t
<220> FEATURE:
<221> NAME/KEY: misc_feature
<222> LOCATION: (834)..(834)
<223> OTHER INFORMATION: n is a, c, g, or t
<220> FEATURE:
<221> NAME/KEY: misc_feature
<222> LOCATION: (836)..(836)
<223> OTHER INFORMATION: n is a, c, g, or t
<220> FEATURE:
<221> NAME/KEY: misc_feature
```

-continued

```
<222> LOCATION: (842)..(842)
<223> OTHER INFORMATION: n is a, c, g, or t
<220> FEATURE:
<221> NAME/KEY: misc_feature
<222> LOCATION: (848)..(848)
<223> OTHER INFORMATION: n is a, c, g, or t
<220> FEATURE:
<221> NAME/KEY: misc_feature
<222> LOCATION: (861)..(861)
<223> OTHER INFORMATION: n is a, c, g, or t
<220> FEATURE:
<221> NAME/KEY: misc_feature
<222> LOCATION: (866)..(866)
<223> OTHER INFORMATION: n is a, c, g, or t

<400> SEQUENCE: 32
ncncnctacc ggaatttggc tctttgccga gngccatatt ctttgccgag ggttttttttt      60 cgggcactcg gcaaanaagc tctttgccga gngtcncgca aaaaacnctc ggnaaaataa     120
aacnctcgac aaanaanatc tttgccgagn gtctttttttt gacnctcggc aaagggctct    180
ttgccgagng ccncaaatac aacactcggc aaanagctct ttgccgaggg ttttttcncc     240
ancnctaggc aaagacaatt taaaaatcnc attttaaagt agtaaattaa ttcaaangaa     300
aaagttttca nctacaaatt tgtataactc atcangangt acaatttata tattgaacat     360
ttcttcatat gacaaaataa aaataaattt gttcataaaa cctatatctc tctcgagagt     420
ttatgaanct agaanagaga cgtataaaat tgngcatatt gttaaancca tcangngaga     480
tcaacaaang accaancanc caaaataaac tttgtanatc ttganaagtt atagaagttt     540
atagttgaca actttttcnt ttgaagtcat attgtcaacg aaaactacnt ctgaatttaa     600
aaatttaaaa atttgaattt tgaaaacgac ttccaaagaa aaaaccacca acatgaaagt     660
tgtaggtatt gaagagttat gaaactttgt agttgacaat gttttggtt tgaaatcatc      720 ttgttatgca aaactatgtt ttgaattttg aaatttgaat ttttcaactg nnccgggang     780 gaaaanccccc caaanaaaag ntggnggncn tngaanttaa tgaanctttg tagntngaca    840
antttttnga tttgaaaccc nctaanct                                        868

<210> SEQ ID NO 33
<211> LENGTH: 81
<212> TYPE: DNA
<213> ORGANISM: Zea mays

<400> SEQUENCE: 33
gaatggaatg ccgtgaacga ggaggtcagg tcggtgctca gggagtaccc ggccgaacct      60
caagctcact cacggcagaa a                                                81

<210> SEQ ID NO 34
<211> LENGTH: 305
<212> TYPE: PRT
<213> ORGANISM: Zea mays

<400> SEQUENCE: 34

Met Thr Lys His Ala Ala Tyr Ser Ser Glu Asp Val Val Ala Val
1               5                  10                  15

Ala Ala Pro Ala Pro Ala Gly Arg His Phe Thr Ser Phe Gln Ala Leu
            20                  25                  30

Lys Gly Ala Pro Leu Asp Cys Lys Lys His Ala Ala Val Asp Leu Ser
        35                  40                  45

Ala Ser Gly Ala Ala Val Val Gly Gly Gly Pro Trp Phe Glu Ser Met
    50                  55                  60
```

```
Lys Ala Ser Ser Pro Arg Arg Ala Ala Asp Ala Glu His Gly Asp Trp
 65                  70                  75                  80

Met Glu Lys His Pro Ser Ala Leu Ala Gln Phe Glu Pro Leu Leu Ala
                 85                  90                  95

Ala Ala Lys Gly Lys Gln Ile Val Met Phe Leu Asp Tyr Asp Gly Thr
            100                 105                 110

Leu Ser Pro Ile Val Glu Asp Pro Asp Arg Ala Val Met Ser Glu Glu
        115                 120                 125

Met Arg Glu Ala Val Arg Arg Val Ala Glu His Phe Pro Thr Ala Ile
    130                 135                 140

Val Ser Gly Arg Cys Arg Asp Lys Val Leu Asn Phe Val Lys Leu Thr
145                 150                 155                 160

Glu Leu Tyr Tyr Ala Gly Ser His Gly Met Asp Ile Gln Gly Pro Ala
                165                 170                 175

Ala Cys Arg Gln Pro Asn His Val Gln Gln Ala Glu Ala Ala Ala Val
            180                 185                 190

His Tyr Gln Ala Ala Ser Glu Phe Leu Pro Val Ile Glu Glu Val Phe
        195                 200                 205

Arg Thr Leu Thr Ala Lys Met Glu Ser Ile Ala Gly Ala Arg Val Glu
    210                 215                 220

His Asn Lys Tyr Cys Leu Ser Val His Phe Arg Cys Val Arg Glu Glu
225                 230                 235                 240

Glu Trp Asn Ala Val Asn Glu Glu Val Arg Ser Val Leu Arg Glu Tyr
                245                 250                 255

Pro Ala Glu Pro Gln Ala His Ser Arg Gln Lys Gly Ala Gly Asp Ser
            260                 265                 270

Ser Val His Gln Val Gly Gln Gly Gln Gly Pro Arg Val Leu Ala Gln
        275                 280                 285

Val Ser Trp Leu Cys Trp Ala Gln Arg Arg Leu Pro Asp Leu His Arg
    290                 295                 300

Arg
305

<210> SEQ ID NO 35
<211> LENGTH: 106
<212> TYPE: DNA
<213> ORGANISM: Zea mays

<400> SEQUENCE: 35
ggtgttccgc acgctgacgg ccaagatgga gtccatcgcc ggcgcgcgcc agggtggagc    60
acaacaagta ctgcctgtcc gtccacttcc gctgcgtccg ggagga                 106

<210> SEQ ID NO 36
<211> LENGTH: 305
<212> TYPE: PRT
<213> ORGANISM: Zea mays

<400> SEQUENCE: 36

Met Thr Lys His Ala Ala Tyr Ser Ser Glu Asp Val Val Ala Ala Val
  1               5                  10                  15

Ala Ala Pro Ala Pro Ala Gly Arg His Phe Thr Ser Phe Gln Ala Leu
             20                  25                  30

Lys Gly Ala Pro Leu Asp Cys Lys Lys His Ala Ala Val Asp Leu Ser
         35                  40                  45

Ala Ser Gly Ala Ala Val Val Gly Gly Gly Pro Trp Phe Glu Ser Met
     50                  55                  60
```

```
Lys Ala Ser Ser Pro Arg Arg Ala Ala Asp Ala Glu His Gly Asp Trp
 65                  70                  75                  80

Met Glu Lys His Pro Ser Ala Leu Ala Gln Phe Glu Pro Leu Leu Ala
                 85                  90                  95

Ala Ala Lys Gly Lys Gln Ile Val Met Phe Leu Asp Tyr Asp Gly Thr
            100                 105                 110

Leu Ser Pro Ile Val Glu Asp Pro Asp Arg Ala Val Met Ser Glu Glu
        115                 120                 125

Met Arg Glu Ala Val Arg Arg Val Ala Glu His Phe Pro Thr Ala Ile
    130                 135                 140

Val Ser Gly Arg Cys Arg Asp Lys Val Leu Asn Phe Val Lys Leu Thr
145                 150                 155                 160

Glu Leu Tyr Tyr Ala Gly Ser His Gly Met Asp Ile Gln Gly Pro Ala
                165                 170                 175

Ala Cys Arg Gln Pro Asn His Val Gln Gln Ala Glu Ala Ala Ala Val
            180                 185                 190

His Tyr Gln Ala Ala Ser Glu Phe Leu Pro Val Ile Glu Glu Val Phe
        195                 200                 205

Arg Thr Leu Thr Ala Lys Met Glu Ser Ile Ala Gly Ala Arg Gln Gly
    210                 215                 220

Gly Ala Gln Gln Val Leu Pro Val Arg Pro Leu Pro Leu Arg Pro Gly
225                 230                 235                 240

Gly Gly Met Glu Cys Arg Glu Arg Gly Gly Gln Val Gly Ala Gln Gly
                245                 250                 255

Val Pro Glu Pro Gln Ala His Ser Arg Gln Lys Gly Ala Gly Asp Ser
            260                 265                 270

Ser Val His Gln Val Gly Gln Gly Gln Gly Pro Arg Val Leu Ala Gln
        275                 280                 285

Val Ser Trp Leu Cys Trp Ala Gln Arg Arg Leu Pro Asp Leu His Arg
    290                 295                 300

Arg
305

<210> SEQ ID NO 37
<211> LENGTH: 234
<212> TYPE: DNA
<213> ORGANISM: Zea mays

<400> SEQUENCE: 37
ggtgctccgc aacatggggc agggcatcgg aatcctggtg tccaagcttc ctaagggttt     60
gtttggataa tctcggattg aaatggattg aggtggtatg tggtgtattg aagtgtaata    120
tgaactaatt ttttttcaat ccccttcaat acaccttaat acacttcaat ccctctgtac    180
ccaaacaaag cctaaggaga cggcggcatc ctactcgctg agtgaccctg ccga           234

<210> SEQ ID NO 38
<211> LENGTH: 335
<212> TYPE: PRT
<213> ORGANISM: Zea mays

<400> SEQUENCE: 38

Met Thr Lys His Ala Ala Tyr Ser Ser Glu Asp Val Val Ala Ala Val
 1               5                  10                  15

Ala Ala Pro Ala Pro Ala Gly Arg His Phe Thr Ser Phe Gln Ala Leu
            20                  25                  30
```

Lys Gly Ala Pro Leu Asp Cys Lys Lys His Ala Ala Val Asp Leu Ser
            35                  40                  45

Ala Ser Gly Ala Ala Val Val Gly Gly Pro Trp Phe Glu Ser Met
 50                  55                  60

Lys Ala Ser Ser Pro Arg Arg Ala Ala Asp Ala Glu His Gly Asp Trp
 65                  70                  75                  80

Met Glu Lys His Pro Ser Ala Leu Ala Gln Phe Glu Pro Leu Leu Ala
                 85                  90                  95

Ala Ala Lys Gly Lys Gln Ile Val Met Phe Leu Asp Tyr Asp Gly Thr
             100                 105                 110

Leu Ser Pro Ile Val Glu Asp Pro Asp Arg Ala Val Met Ser Glu Glu
             115                 120                 125

Met Arg Glu Ala Val Arg Arg Val Ala Glu His Phe Pro Thr Ala Ile
130                 135                 140

Val Ser Gly Arg Cys Arg Asp Lys Val Leu Asn Phe Val Lys Leu Thr
145                 150                 155                 160

Glu Leu Tyr Tyr Ala Gly Ser His Gly Met Asp Ile Gln Gly Pro Ala
                165                 170                 175

Ala Cys Arg Gln Pro Asn His Val Gln Gln Ala Glu Ala Ala Ala Val
            180                 185                 190

His Tyr Gln Ala Ala Ser Glu Phe Leu Pro Val Ile Glu Glu Val Phe
        195                 200                 205

Arg Thr Leu Thr Ala Lys Met Glu Ser Ile Ala Gly Ala Arg Val Glu
        210                 215                 220

His Asn Lys Tyr Cys Leu Ser Val His Phe Arg Cys Val Arg Glu Glu
225                 230                 235                 240

Glu Trp Asn Ala Val Asn Glu Glu Val Arg Ser Val Leu Arg Glu Tyr
                245                 250                 255

Pro Asn Leu Lys Leu Thr His Gly Arg Lys Val Leu Glu Ile Arg Pro
            260                 265                 270

Ser Ile Lys Trp Asp Lys Gly Lys Ala Leu Glu Phe Leu Leu Lys Ser
        275                 280                 285

Leu Gly Tyr Ala Gly Arg Asn Asp Val Phe Pro Ile Tyr Ile Gly Asp
    290                 295                 300

Asp Arg Thr Asp Glu Asp Ala Phe Lys Val Leu Arg Asn Met Gly Gln
305                 310                 315                 320

Gly Ile Gly Ile Leu Val Ser Lys Leu Pro Lys Gly Leu Phe Gly
                325                 330                 335

<210> SEQ ID NO 39
<211> LENGTH: 190
<212> TYPE: DNA
<213> ORGANISM: Zea mays

<400> SEQUENCE: 39
ggtgttccgc acgctgacgg ccaagatgga gtccatcgcc ggcgccaggg tggagcacaa    60
caagtactgc ctgtccgtcc acttccgctg cgtccgggag gagatatata tgaatgga   120 atgccgtgaa cgaggaggtc aggtcggtgc tcagggagta cccgaacctc aagctcactc   180
acggcagaaa                                                         190

<210> SEQ ID NO 40
<211> LENGTH: 243
<212> TYPE: PRT
<213> ORGANISM: Zea mays

<400> SEQUENCE: 40

```
Met Thr Lys His Ala Ala Tyr Ser Ser Glu Asp Val Val Ala Ala Val
1               5                  10                   15

Ala Ala Pro Ala Pro Ala Gly Arg His Phe Thr Ser Phe Gln Ala Leu
             20                  25                  30

Lys Gly Ala Pro Leu Asp Cys Lys Lys His Ala Ala Val Asp Leu Ser
             35                  40                  45

Ala Ser Gly Ala Ala Val Val Gly Gly Gly Pro Trp Phe Glu Ser Met
 50                  55                  60

Lys Ala Ser Ser Pro Arg Arg Ala Ala Asp Ala Glu His Gly Asp Trp
 65                  70                  75                  80

Met Glu Lys His Pro Ser Ala Leu Ala Gln Phe Glu Pro Leu Leu Ala
                 85                  90                  95

Ala Ala Lys Gly Lys Gln Ile Val Met Phe Leu Asp Tyr Asp Gly Thr
            100                 105                 110

Leu Ser Pro Ile Val Glu Asp Pro Asp Arg Ala Val Met Ser Glu Glu
            115                 120                 125

Met Arg Glu Ala Val Arg Arg Val Ala Glu His Phe Pro Thr Ala Ile
130                 135                 140

Val Ser Gly Arg Cys Arg Asp Lys Val Leu Asn Phe Val Lys Leu Thr
145                 150                 155                 160

Glu Leu Tyr Tyr Ala Gly Ser His Gly Met Asp Ile Gln Gly Pro Ala
                165                 170                 175

Ala Cys Arg Gln Pro Asn His Val Gln Gln Ala Glu Ala Ala Ala Val
            180                 185                 190

His Tyr Gln Ala Ala Ser Glu Phe Leu Pro Val Ile Glu Glu Val Phe
            195                 200                 205

Arg Thr Leu Thr Ala Lys Met Glu Ser Ile Ala Gly Ala Arg Val Glu
210                 215                 220

His Asn Lys Tyr Cys Leu Ser Val His Phe Arg Cys Val Arg Glu Glu
225                 230                 235                 240

Ile Tyr Ile
```

<210> SEQ ID NO 41
<211> LENGTH: 85
<212> TYPE: DNA
<213> ORGANISM: Zea mays

<400> SEQUENCE: 41

```
ggtgttccgc acgctgacgg ccaagatgga ggccatcgcc tgcgtccact tccgcttccg    60
tccacttccg ctgcgtccgg gagga                                         85
```

<210> SEQ ID NO 42
<211> LENGTH: 298
<212> TYPE: PRT
<213> ORGANISM: Zea mays

<400> SEQUENCE: 42

```
Met Thr Lys His Ala Ala Tyr Ser Ser Glu Asp Val Val Ala Ala Val
1               5                  10                   15

Ala Ala Pro Ala Pro Ala Gly Arg His Phe Thr Ser Phe Gln Ala Leu
             20                  25                  30

Lys Gly Ala Pro Leu Asp Cys Lys Lys His Ala Ala Val Asp Leu Ser
             35                  40                  45

Ala Ser Gly Ala Ala Val Val Gly Gly Gly Pro Trp Phe Glu Ser Met
```

-continued

```
                50                  55                  60
Lys Ala Ser Ser Pro Arg Arg Ala Ala Asp Ala Glu His Gly Asp Trp
 65                  70                  75                  80

Met Glu Lys His Pro Ser Ala Leu Ala Gln Phe Glu Pro Leu Leu Ala
                 85                  90                  95

Ala Ala Lys Gly Lys Gln Ile Val Met Phe Leu Asp Tyr Asp Gly Thr
            100                 105                 110

Leu Ser Pro Ile Val Glu Asp Pro Asp Arg Ala Val Met Ser Glu Glu
            115                 120                 125

Met Arg Glu Ala Val Arg Val Ala Glu His Phe Pro Thr Ala Ile
130                 135                 140

Val Ser Gly Arg Cys Arg Asp Lys Val Leu Asn Phe Val Lys Leu Thr
145                 150                 155                 160

Glu Leu Tyr Tyr Ala Gly Ser His Gly Met Asp Ile Gln Gly Pro Ala
                165                 170                 175

Ala Cys Arg Gln Pro Asn His Val Gln Gln Ala Glu Ala Ala Ala Val
            180                 185                 190

His Tyr Gln Ala Ala Ser Glu Phe Leu Pro Val Ile Glu Glu Val Phe
        195                 200                 205

Arg Thr Leu Thr Ala Lys Met Glu Ala Ile Ala Cys Val His Phe Arg
210                 215                 220

Phe Arg Pro Leu Pro Leu Arg Pro Gly Gly Gly Met Glu Cys Arg Glu
225                 230                 235                 240

Arg Gly Gly Gln Val Gly Ala Gln Gly Val Pro Glu Pro Gln Ala His
                245                 250                 255

Ser Arg Gln Lys Gly Ala Gly Asp Ser Ser Val His Gln Val Gly Gln
            260                 265                 270

Gly Gln Gly Pro Arg Val Leu Ala Gln Val Ser Trp Leu Cys Trp Ala
            275                 280                 285

Gln Arg Arg Leu Pro Asp Leu His Arg Arg
        290                 295

<210> SEQ ID NO 43
<211> LENGTH: 104
<212> TYPE: DNA
<213> ORGANISM: Zea mays

<400> SEQUENCE: 43
ggtgttccgc acgctgacgg ccaagatgga gtccatcgcc ggcgccacag ggtggagcac      60
aacaagtact gcctgtccgt ccacttccgc tgcgtccggg agga                      104

<210> SEQ ID NO 44
<211> LENGTH: 245
<212> TYPE: PRT
<213> ORGANISM: Zea mays

<400> SEQUENCE: 44

Met Thr Lys His Ala Ala Tyr Ser Ser Glu Asp Val Val Ala Val
  1               5                  10                  15

Ala Ala Pro Ala Pro Ala Gly Arg His Phe Thr Ser Phe Gln Ala Leu
                 20                  25                  30

Lys Gly Ala Pro Leu Asp Cys Lys Lys His Ala Ala Val Asp Leu Ser
             35                  40                  45

Ala Ser Gly Ala Ala Val Val Gly Gly Gly Pro Trp Phe Glu Ser Met
         50                  55                  60
```

```
Lys Ala Ser Ser Pro Arg Arg Ala Ala Asp Ala Glu His Gly Asp Trp
 65                  70                  75                  80
Met Glu Lys His Pro Ser Ala Leu Ala Gln Phe Glu Pro Leu Leu Ala
                 85                  90                  95
Ala Ala Lys Gly Lys Gln Ile Val Met Phe Leu Asp Tyr Asp Gly Thr
            100                 105                 110
Leu Ser Pro Ile Val Glu Asp Pro Asp Arg Ala Val Met Ser Glu Glu
        115                 120                 125
Met Arg Glu Ala Val Arg Arg Val Ala Glu His Phe Pro Thr Ala Ile
130                 135                 140
Val Ser Gly Arg Cys Arg Asp Lys Val Leu Asn Phe Val Lys Leu Thr
145                 150                 155                 160
Glu Leu Tyr Tyr Ala Gly Ser His Gly Met Asp Ile Gln Gly Pro Ala
                165                 170                 175
Ala Cys Arg Gln Pro Asn His Val Gln Gln Ala Glu Ala Ala Ala Val
            180                 185                 190
His Tyr Gln Ala Ala Ser Glu Phe Leu Pro Val Ile Glu Glu Val Phe
        195                 200                 205
Arg Thr Leu Thr Ala Lys Met Glu Ser Ile Ala Gly Ala Thr Gly Trp
210                 215                 220
Ser Thr Thr Ser Thr Ala Cys Pro Ser Thr Ser Ala Ala Ser Gly Arg
225                 230                 235                 240
Arg Asn Gly Met Pro
                245
```

<210> SEQ ID NO 45
<211> LENGTH: 14
<212> TYPE: PRT
<213> ORGANISM: Arabidopsis thaliana

<400> SEQUENCE: 45

```
Leu Asp Tyr Asp Gly Thr Leu Ser Pro Ile Val Glu Asp Pro
1               5                   10
```

<210> SEQ ID NO 46
<211> LENGTH: 10
<212> TYPE: PRT
<213> ORGANISM: Arabidopsis thaliana

<400> SEQUENCE: 46

```
Gly Asp Asp Arg Thr Asp Glu Asp Ala Phe
1               5                   10
```

<210> SEQ ID NO 47
<211> LENGTH: 4439
<212> TYPE: DNA
<213> ORGANISM: Zea mays

<400> SEQUENCE: 47

```
acagcctgag atgcatgcgg gagaggggtc tagtggccag gctggtccga tgttacagga      60
gtggctgacc ggagcttcat gtattctagt ggaatatata tatatatata tatatatata     120
tatatatata tatatatata tatatatata tatctacgaa caatgttgat ataactcact     180
aaagtatttt ttagttaatt ttaccactct acttctttga gttattaaaa tttacctctt     240
gacaaaatta tttatcattt taaattttta tgtgcaaact aagttttcag tttaaatttt     300
gttggttagt agctaatagc ataatttaac atagaaaaac atattatgat ttttaatagt     360
tattttgata ggtttggtat cagataagac aataaacttta gggttttttta aactggtgcc     420
```

| | |
|---|---|
| cttagttttg gtggtgtgct cacctatatc cttagtcgtg ttttttttca gctatgtcat | 480 |
| tccagtgcta tacaaatgat ataaaaataa atgtaataat aaaatattct aacatatttt | 540 |
| taatgttctt aataatagtg gaaaatacaa acttgaaatc aaacttgtac gtgaagaaga | 600 |
| aacgaaaaaa atctgcttcc aatgaaaaaa aatcataatt cgccactatc ttatacattc | 660 |
| ggaggccggt acaattgaga gaaaaaaata tatcgcacta gtgcatcgca ttcaacgtcg | 720 |
| caatcttgct agtacgtatt atatttattt tggatatgaa agacgatcgc actcaggagg | 780 |
| cctgaagtta catagcaaat acagtcggta cgaattatcg tttgtcgatc aatgcaaaga | 840 |
| caagatgcaa tgcatgccac cgctgcctgc ccctgccact gttacaaaac cggtgtcgcg | 900 |
| tccacccaac caagacaccc ggccggccac aactatatag agcccctccc ctccgcagtc | 960 |
| cgcactgccc ggaaccaagc aaccaacgca ttcaggcccc tcgcgcgtgt tctgtctctc | 1020 |
| cgatccagcc agccagccag ccatccattc atccgtgtgg tgtggtcgtc gcctctctcc | 1080 |
| tcctttcctt ctccgatccg cctccagcgt gcagcgtcca cgtcctgatt gttcagtggt | 1140 |
| ttctcgatcg agaccgcgcg cgcgcaatga cgaagcgcac cgccttcgcc gcggacgacg | 1200 |
| cgatcatcgc cgccgccgcc gccgtcacgt cgcagcccgg ccggcggttc acgtcgtacc | 1260 |
| cgccggcgag ggcgcgcggc ggatgcaggc tggccccggc ggtggcggcg gcggcgcgcc | 1320 |
| aggccacgga cgaccccggc gccgctgggt cctggccaga actagtcgtg ccgcggcacg | 1380 |
| ccgacttcga cgactggatg gtacgtaaat acgtgcccgg ccgccgtcgt tcgcgtgcca | 1440 |
| ttcgaccata tacgcctcgc ttgttgtgtc tacgttgtgt ttgtgttgtg ccgatgctcg | 1500 |
| tcaatcgtcg tcgtcgctga catgacctga catgacctga ccgccgcgct gcccacccgt | 1560 |
| accgtacgcg cacaggagaa gcacccgtcg gcattggccg cgttcgagtc ggtgctggcc | 1620 |
| gccgccaaag gcaagaagat cgtcatgttc ctcgactacg acggcaccct gtcgccgatc | 1680 |
| gtcagggacc ccgacagcgc cgtcatgtcc gaggaggtca ggcaataata cctatcesttt | 1740 |
| tctgtttcct atgtggatga aggcgcggag tggcggagca gcagggcatg gtgtgcggct | 1800 |
| ccggcgaacg cacgccatgc atgcacgggc ctagactagc tagctgcttg cctgacgctt | 1860 |
| ttttttttct gtggcacgcc gcagatgcgg gacgcggtga gaggcgtggc cgagcacttc | 1920 |
| ccgacggcga tcgtgagcgg gaggtgtaga gacaaggtac cttttcttcc tccatctctc | 1980 |
| tctctctctc tcttctctct acagttttac atcggtcttt gctggggagt ggggcctcgc | 2040 |
| aatctttgtg aaatgtgctt ttccgttgtg gcttttcagt tattcatcag tgctgtgctg | 2100 |
| aatgctgatg ggtctgttct actctggtgc gatatctagg tgttcaactt cgtgaagctg | 2160 |
| gcggagctgt actacgccgg gagccacggc atggacatca agggcccac agcacagtcc | 2220 |
| aagcacacca aggcaaaggt cagcagctac ccttgtctgt cttccacca ggcctgtaca | 2280 |
| ggcttgagat atatactgac agtcgttct tacagaattt ggcttctttt tgtattccat | 2340 |
| ataaacttaa tctactttcg ttgacttgga aatgcaggcc ggagccgttc tatgccaacc | 2400 |
| tgcgagggcg ttcctgccgg tcattgagga ggtaatttaa tttagttgaa gtttctcctg | 2460 |
| acatgtttac ctgcgagggc gtgctacaag caagcaacac acaggcgtct agctagttcg | 2520 |
| ccagcatgac tcttgctctg tctgcaactt cttctctgca ggtgtaccgc gcgctgacgg | 2580 |
| cgagcacggc gccgatcccc ggcgcgacgg tggagaacaa caagttctgc ctctccgtcc | 2640 |
| acttccgctg cgtccaggag gaggtgagga tgtgtctacg agcacacgca cggaacggaa | 2700 |
| gggtcgttcg ccgccgtctc gcgtaataac tgacacatgc atgtaatatc cggggcagaa | 2760 |

```
atggcgcgct ctggaggagc aggtccggtc ggtgctcaag gagtacccgg acctccgcct    2820
caccaagggc aggaaggtcc tcgagatccg gccgtccatc aagtgggaca agggcaacgc    2880
cctgcagttc ttgctcgagt ctctcggtga gtgcttgtgc ttgcttctca tcgaatcatt    2940
ggattttgct gttcactgcc gacgacgacg taatgacgta taggtgctaa tagtttgcct    3000
gccatgcatg gttcaatttc ctcaaggttt tgctggcagt aacagtgtct tcccgatata    3060
tatcggagac gatagcaccg acgaggacgc gttcaaggta attcctttta gtaacatttg    3120
agtctgacaa acaatccata tgttgcatat gttgtgttta gaccaaggaa ttcatatgtt    3180
gtgtcaagac cgtgaaatta acgatattat gagatgtctc tcaacagcaa tctaagctaa    3240
aaaaaaccat ttttttttc atatgtagct tgttctgac gctactggga aggcaactat    3300
actgacgctt ttgctgtttc cgtcaaactg taacaggtcc tgcgcaactt ggggcaaggg    3360
atcgggatcc tggtgagcaa gattccgaag gagacccgcg catcctactc cctgcgtgaa    3420
ccttctgagg tagcaacact acccactgct accagttatt actgtacagt acgtgcacgg    3480
gctacctagt tcagttcagt tcagttcagt tcagtgcttt aagctgttca ctgaaaaatg    3540
tgaaacagaa ctagcagaaa ccccgcatcg gaaagtcacg gttgctgttg cacttgtgta    3600
ggcacaggcc atgcacgcct tgcccgcgag tgctcgctgt tgctttcgag aaaagctcga    3660
gctgttggac caccccttt cttctactat atatatatat ataatatatg ctctacagct    3720
gtgctttgta tatagctgtg cttttcatga catgtaactg aaccgtcacc gacgtggact    3780
gaacctgtct agtgtgcgtt tggcgctgcg tgcaggtgga ggagttcctg cgcaagttgg    3840
tcagctggtc caaggagagc aggcaacggg actagtcatg gtccagtcag caggcgatgg    3900
aaagctttgc ctagaagcgg tcgacagggc cggctctcgt tttttaagg gccatagacc    3960 aacctcgatg tttaggcctc tgatttttt attgtcaata actgtaataa aatagaggga    4020
aaataataaa aataatttaa tggtaaatta ctgcgaatat cttaagtgag aataaaatct    4080
agagtgttct aaattacgtt tttagattgc gtatagatct aatatctctt aaataaataa    4140
ctccgtccag catatttttt aaaagcaaaa gatcaacatt ttttaacgta tccttctcga    4200
tagaacatgt agctaaaagc tatttaacct ttcttgctac atagttgacc ttaaataact    4260
tctcaataat attagctttg agaaaacttg gtcaaaaaat ccatgtgata cagataaatt    4320
tggataacaa tctacaactg taatgcacat aaggatctca gttacaggca tcaaagcatg    4380
agaaaaaatt acttgcaaga cttaaaattc actgataaaa aatatctgca aattgttttt    4439
```

<210> SEQ ID NO 48
<211> LENGTH: 1113
<212> TYPE: DNA
<213> ORGANISM: Zea mays

<400> SEQUENCE: 48

```
atgacgaagc gcaccgcctt cgccgcggac gacgcgatca tcgccgccgc cgccgccgtc     60
acgtcgcagc ccggccggcg gttcacgtcg tacccgccgg cgagggcgcg cggcggatgc    120
aggctggccc cggcggtggc ggcggcggcg cgccaggcca cggacgaccc cggcgccgct    180
gggtcctggc cagaactagt cgtgccgcgg cacgccgact tcgacgactg gatggagaag    240
cacccgtcgg cattggccgc gttcgagtcg gtgctggccg ccgccaaagg caagaagatc    300
gtcatgttcc tcgactacga cggcacccctg tcgccgatcg tcagggaccc cgacagcgcc    360
gtcatgtccg aggagatgcg ggacgcggtg agaggcgtgg ccgagcactt cccgacggcg    420
atcgtgagcg ggaggtgtag agacaaggtg ttcaacttcg tgaagctggc ggagctgtac    480
```

```
tacgccggga gccacggcat ggacatcaag ggccccacag cacagtccaa gcacaccaag    540
gcaaaggccg gagccgttct atgccaacct gcgagggcgt tcctgccggt cattgaggag    600
gtgtaccgcg cgctgacggc gagcacggcg ccgatcccg gcgcgacggt ggagaacaac     660
aagttctgcc tctccgtcca cttccgctgc gtccaggagg agaaatggcg cgctctggag    720
gagcaggtcc ggtcggtgct caaggagtac ccggacctcc gcctcaccaa gggcaggaag    780
gtcctcgaga tccggccgtc catcaagtgg gacaagggca acgccctgca gttcttgctc    840
gagtctctcg gttttgctgg cagtaacagt gtcttcccga tatatatcgg agacgatagc    900
accgacgagg acgcgttcaa ggtcctgcgc aacttggggc aagggatcgg gatcctggtg    960
agcaagattc cgaaggagac ccgcgcatcc tactccctgc gtgaaccttc tgaggtagca    1020
acactaccca ctgctaccag ttattactgt acagtggagg agttcctgcg caagttggtc    1080
agctggtcca aggagagcag gcaacgggac tag                                 1113
```

<210> SEQ ID NO 49
<211> LENGTH: 370
<212> TYPE: PRT
<213> ORGANISM: Zea mays

<400> SEQUENCE: 49

```
Met Thr Lys Arg Thr Ala Phe Ala Ala Asp Asp Ala Ile Ile Ala Ala
1               5                   10                  15

Ala Ala Val Thr Ser Gln Pro Gly Arg Arg Phe Thr Ser Tyr Pro
            20                  25                  30

Pro Ala Arg Ala Arg Gly Gly Cys Arg Leu Ala Pro Ala Val Ala Ala
        35                  40                  45

Ala Ala Arg Gln Ala Thr Asp Asp Pro Gly Ala Ala Gly Ser Trp Pro
    50                  55                  60

Glu Leu Val Val Pro Arg His Ala Asp Phe Asp Trp Met Glu Lys
65                  70                  75                  80

His Pro Ser Ala Leu Ala Ala Phe Glu Ser Val Leu Ala Ala Ala Lys
                85                  90                  95

Gly Lys Lys Ile Val Met Phe Leu Asp Tyr Asp Gly Thr Leu Ser Pro
            100                 105                 110

Ile Val Arg Asp Pro Asp Ser Ala Val Met Ser Glu Glu Met Arg Asp
        115                 120                 125

Ala Val Arg Gly Val Ala Glu His Phe Pro Thr Ala Ile Val Ser Gly
    130                 135                 140

Arg Cys Arg Asp Lys Val Phe Asn Phe Val Lys Leu Ala Glu Leu Tyr
145                 150                 155                 160

Tyr Ala Gly Ser His Gly Met Asp Ile Lys Gly Pro Thr Ala Gln Ser
                165                 170                 175

Lys His Thr Lys Ala Lys Ala Gly Ala Val Leu Cys Gln Pro Ala Arg
            180                 185                 190

Ala Phe Leu Pro Val Ile Glu Glu Val Tyr Arg Ala Leu Thr Ala Ser
        195                 200                 205

Thr Ala Pro Ile Pro Gly Ala Thr Val Glu Asn Asn Lys Phe Cys Leu
    210                 215                 220

Ser Val His Phe Arg Cys Val Gln Glu Glu Lys Trp Arg Ala Leu Glu
225                 230                 235                 240

Glu Gln Val Arg Ser Val Leu Lys Glu Tyr Pro Asp Leu Arg Leu Thr
                245                 250                 255
```

-continued

```
Lys Gly Arg Lys Val Leu Glu Ile Arg Pro Ser Ile Lys Trp Asp Lys
            260                 265                 270

Gly Asn Ala Leu Gln Phe Leu Leu Glu Ser Leu Gly Phe Ala Gly Ser
        275                 280                 285

Asn Ser Val Phe Pro Ile Tyr Ile Gly Asp Asp Ser Thr Asp Glu Asp
    290                 295                 300

Ala Phe Lys Val Leu Arg Asn Leu Gly Gln Gly Ile Gly Ile Leu Val
305                 310                 315                 320

Ser Lys Ile Pro Lys Glu Thr Arg Ala Ser Tyr Ser Leu Arg Glu Pro
                325                 330                 335

Ser Glu Val Ala Thr Leu Pro Thr Ala Thr Ser Tyr Tyr Cys Thr Val
            340                 345                 350

Glu Glu Phe Leu Arg Lys Leu Val Ser Trp Ser Lys Glu Ser Arg Gln
        355                 360                 365

Arg Asp
    370
```

<210> SEQ ID NO 50
<211> LENGTH: 707
<212> TYPE: DNA
<213> ORGANISM: Zea mays

<400> SEQUENCE: 50

```
gcacgagaag gccggagccg ttctatgcca acctgcgagg gcgttcctgc cggtcattga      60
ggaggtgtac cgcgcgctga cggcgagcac ggcgccgatc cccggcgcga cggtggagaa     120
caacaagttc tgcctctccg tccacttccg ctgcgtccag gaggagaaat ggcgcgctct     180
ggaggagcag gtccggtcgg tgctcaagga gtacccggac ctccgcctca ccaagggcag     240
gaaggtcctc gagatccggc cgtccatcaa gtgggacaag ggcaacgccc tgcagttctt     300
gctcgagtct ctcggttttg ctggcagtaa cagtgtcttc ccgatatata tcggagacga     360
tagcaccgac gaggacgcgt tcaaggtcct gcgcaacttg ggcaagggca tcgggatcct     420
ggtgagcaag attccgaagg agacccgcgc atcctactcc ctgcgtgaac cttctgaggt     480
ggaggagttc ctgcgcaagt tggtcagctg gtccaaggag agcaggcaac gggactagtc     540
atggtccagt cagcaggcga tggaaagctt tgcctagaag cggtcgacag gccggctct      600
cgttttttta agggccatag accaacctcg atgtttaggc ctctgatttt tttattgtca     660
ataactgtaa taaatagag ggaaaataat aaaaataatt taatggt                     707
```

<210> SEQ ID NO 51
<211> LENGTH: 366
<212> TYPE: PRT
<213> ORGANISM: Oryza sativa

<400> SEQUENCE: 51

```
Met Thr Asn His Ala Gly Phe Ala Ala Asp Asp Ala Val Thr Ala Ala
1               5                   10                  15

Val Pro Val Gln Ala Ala Gln Gly Gly Arg His Phe Pro Pro Phe Leu
            20                  25                  30

Ala Pro Ser Ser Arg Leu Thr Asp Cys Lys Lys Ala Ala Ala His Val
        35                  40                  45

Asp Leu Ala Gly Ala Gly Gly Val Ala Thr Val Pro Gly Ser Trp Pro
    50                  55                  60

Arg His Ala Lys Pro Val Ser Gly Ala Glu Leu Asp Asp Trp Met Glu
65                  70                  75                  80
```

```
Lys His Pro Ser Ala Leu Ala Trp Phe Glu Ser Val Ala Ala Ala
                85                  90                  95

Lys Gly Lys Glu Ile Val Val Phe Leu Asp Tyr Asp Gly Thr Leu Ser
            100                 105                 110

Pro Ile Val Ala Asp Pro Asp Arg Ala Phe Met Ser Asp Glu Met Arg
        115                 120                 125

Glu Ala Val Arg Gly Val Ala Lys His Phe Pro Thr Ala Ile Val Ser
    130                 135                 140

Gly Arg Cys Ile Asp Lys Val Phe Asp Phe Val Lys Leu Glu Glu Leu
145                 150                 155                 160

Tyr Tyr Ala Gly Ser His Gly Met Asp Ile Arg Gly Pro Thr Ala Ala
                165                 170                 175

Ala Ser Glu Tyr Asn His Asn Met Lys Ala Lys Gln Gly Asp Ala Val
            180                 185                 190

Thr Phe Gln Pro Ala Ala Asp Phe Leu Pro Val Ile Glu Glu Val Tyr
        195                 200                 205

His Val Leu Lys Glu Arg Met Ala Ser Ile Arg Gly Ser Leu Val Glu
    210                 215                 220

Asn Asn Lys Phe Cys Leu Ser Val His Tyr Arg Cys Val Asp Glu Ala
225                 230                 235                 240

Glu Trp Gly Val Leu Asp Gly Lys Val Arg Ala Val Ile Glu Gly Tyr
                245                 250                 255

Pro Asp Leu Arg Leu Ser Lys Gly Arg Lys Val Leu Glu Ile Arg Pro
            260                 265                 270

Val Ile Asp Trp Asp Lys Gly Ser Ala Leu Gln Phe Leu Lys Ser
        275                 280                 285

Leu Gly Tyr Glu Gly Arg Asn Asn Val Phe Pro Ile Tyr Ile Gly Asp
    290                 295                 300

Asp Arg Thr Asp Glu Asp Ala Phe Lys Val Leu Arg Asn Met Gly Gln
305                 310                 315                 320

Gly Ile Gly Ile Leu Val Thr Lys Val Pro Lys Glu Thr Ala Ala Ser
                325                 330                 335

Tyr Thr Leu Arg Glu Pro Ser Glu Val Lys Glu Phe Leu Arg Lys Leu
            340                 345                 350

Val Lys Ile Lys Ile Asn Gly Asp Lys Gly Leu Ile Gly Lys
        355                 360                 365

<210> SEQ ID NO 52
<211> LENGTH: 385
<212> TYPE: PRT
<213> ORGANISM: Arabidopsis thaliana

<400> SEQUENCE: 52

Met Asp Met Lys Ser Gly His Ser Ser Pro Val Met Thr Asp Ser Pro
1               5                   10                  15

Pro Ile Ser Asn Ser Arg Leu Thr Ile Arg Gln Asn Arg Leu Pro Tyr
            20                  25                  30

Ser Ser Ala Ala Ala Thr Ala Ile Ser Gln Asn Asn Asn Leu Leu Leu
        35                  40                  45

Thr Val Pro Arg Lys Lys Thr Gly Ile Leu Asp Asp Val Lys Ser Asn
    50                  55                  60

Gly Trp Leu Asp Ala Met Lys Ser Ser Pro Pro Thr Ile Leu
65                  70                  75                  80

Asn Lys Asp Asn Leu Ser Asn Asp Ala Thr Asp Met Thr Tyr Arg Glu
                85                  90                  95
```

```
Trp Met Gln Leu Lys Tyr Pro Ser Ala Leu Thr Ser Phe Glu Lys Ile
            100                 105                 110

Met Ser Phe Ala Lys Gly Lys Arg Ile Ala Leu Phe Leu Asp Tyr Asp
        115                 120                 125

Gly Thr Leu Ser Pro Ile Val Glu Glu Pro Asp Cys Ala Tyr Met Ser
    130                 135                 140

Ser Ala Met Arg Ser Ala Val Gln Asn Val Ala Lys Tyr Phe Pro Thr
145                 150                 155                 160

Ala Ile Ile Ser Gly Arg Ser Arg Asp Lys Val Tyr Glu Phe Val Asn
                165                 170                 175

Leu Ser Glu Leu Tyr Tyr Ala Gly Ser His Gly Met Asp Ile Met Ser
            180                 185                 190

Pro Ala Gly Glu Ser Leu Asn His Glu His Ser Arg Thr Val Ser Val
        195                 200                 205

Tyr Glu Gln Gly Lys Asp Val Asn Leu Phe Gln Pro Ala Ser Glu Phe
    210                 215                 220

Leu Pro Met Ile Asp Lys Val Leu Cys Ser Leu Ile Glu Ser Thr Lys
225                 230                 235                 240

Asp Ile Lys Gly Val Lys Val Glu Asp Asn Lys Phe Cys Ile Ser Val
                245                 250                 255

His Tyr Arg Asn Val Glu Glu Lys Asn Trp Thr Leu Val Ala Gln Cys
            260                 265                 270

Val Asp Asp Val Ile Arg Thr Tyr Pro Lys Leu Arg Leu Thr His Gly
        275                 280                 285

Arg Lys Val Leu Glu Ile Arg Pro Val Ile Asp Trp Asp Lys Gly Lys
    290                 295                 300

Ala Val Thr Phe Leu Leu Glu Ser Leu Gly Leu Asn Asn Cys Glu Asp
305                 310                 315                 320

Val Leu Pro Ile Tyr Val Gly Asp Asp Arg Thr Asp Glu Asp Ala Phe
                325                 330                 335

Lys Val Leu Arg Asp Gly Pro Asn His Gly Tyr Gly Ile Leu Val Ser
            340                 345                 350

Ala Val Pro Lys Asp Ser Asn Ala Phe Tyr Ser Leu Arg Asp Pro Ser
        355                 360                 365

Glu Val Met Glu Phe Leu Lys Ser Leu Val Thr Trp Lys Arg Ser Met
    370                 375                 380

Gly
385

<210> SEQ ID NO 53
<211> LENGTH: 374
<212> TYPE: PRT
<213> ORGANISM: Arabidopsis thaliana

<400> SEQUENCE: 53

Met Thr Asn Gln Asn Val Ile Val Ser Asp Arg Lys Pro Ile Leu Gly
1               5                   10                  15

Leu Lys Thr Ile Thr Val Ser Val Ser Asn Ser Pro Leu Phe Ser Asn
            20                  25                  30

Ser Phe Pro Thr Tyr Phe Asn Phe Pro Arg Arg Lys Leu Leu Lys Leu
        35                  40                  45

Leu Glu Ala Ala Asp Lys Asn Asn Leu Val Val Ala Pro Lys Ile Thr
    50                  55                  60

Ser Met Ile Asp Ser Met Arg Asp Ser Ser Pro Thr Arg Leu Arg Ser
```

```
                65                  70                  75                  80
Ser Ser Tyr Asp Ser Asp Ser Asn Asp Asp Lys Thr Ser Trp Ile
                    85                  90                  95
Val Arg Phe Pro Ser Ala Leu Asn Met Phe Asp Glu Ile Val Asn Ala
                100                 105                 110
Ala Lys Gly Lys Gln Ile Val Met Phe Leu Asp Tyr Asp Gly Thr Leu
                115                 120                 125
Ser Pro Ile Val Glu Asp Pro Asp Lys Ala Phe Ile Thr His Glu Met
                130                 135                 140
Arg Glu Val Val Lys Asp Val Ala Ser Asn Phe Pro Thr Ala Ile Val
145                 150                 155                 160
Thr Gly Arg Ser Ile Glu Lys Val Arg Ser Phe Val Gln Val Asn Glu
                165                 170                 175
Ile Tyr Tyr Ala Gly Ser His Gly Met Asp Ile Glu Gly Pro Thr Asn
                180                 185                 190
Glu Asn Ser Asn Gly Gln Ser Asn Glu Arg Val Leu Phe Gln Pro Ala
                195                 200                 205
Arg Glu Phe Leu Pro Met Ile Glu Lys Val Val Asn Ile Leu Glu Glu
            210                 215                 220
Lys Thr Lys Trp Ile Pro Gly Ala Met Val Glu Asn Asn Lys Phe Cys
225                 230                 235                 240
Leu Ser Val His Phe Arg Arg Val Asp Glu Lys Arg Trp Pro Ala Leu
                245                 250                 255
Ala Glu Val Val Lys Ser Val Leu Ile Asp Tyr Pro Lys Leu Lys Leu
                260                 265                 270
Thr Gln Gly Arg Lys Val Leu Glu Ile Arg Pro Thr Ile Lys Trp Asp
            275                 280                 285
Lys Gly Gln Ala Leu Asn Phe Leu Leu Lys Ser Leu Gly Tyr Glu Asn
            290                 295                 300
Ser Asp Asp Val Val Pro Val Tyr Ile Gly Asp Asp Arg Thr Asp Glu
305                 310                 315                 320
Asp Ala Phe Lys Val Leu Arg Glu Arg Gly Gln Gly Phe Gly Ile Leu
                325                 330                 335
Val Ser Lys Val Pro Lys Asp Thr Asn Ala Ser Tyr Ser Leu Gln Asp
                340                 345                 350
Pro Ser Gln Val Asn Lys Phe Leu Glu Arg Leu Val Glu Trp Lys Arg
                355                 360                 365
Lys Thr Val Gly Glu Glu
            370

<210> SEQ ID NO 54
<211> LENGTH: 369
<212> TYPE: PRT
<213> ORGANISM: Zea mays

<400> SEQUENCE: 54

Met Asp Met Gly Ser Gly Ser Ser Pro Val Ile Thr Asp Pro Ile Ser
1               5                   10                  15
Ile Ser Pro Pro Leu Leu Gly Gly Leu Thr Ser Asn Leu Met Pro Phe
                20                  25                  30
Ser Val Met Ser Gly Gly Cys Ser Ser Ser Pro Ser Met Ser Ala Ser
                35                  40                  45
Ser Arg Arg Lys Ile Glu Glu Val Leu Val Asn Gly Leu Leu Asp Ala
            50                  55                  60
```

```
Met Lys Ser Ser Ser Pro Arg Lys Lys His Asn Leu Ala Phe Gly Gln
 65                  70                  75                  80

Asp Asn Ser Pro Asp Glu Asp Pro Ala Tyr Thr Ala Trp Leu Ser Lys
                 85                  90                  95

Cys Pro Ser Ala Leu Ala Ser Phe Lys Gln Ile Val Ala Asn Ala Gln
            100                 105                 110

Gly Arg Arg Ile Ala Val Phe Leu Asp Tyr Asp Gly Thr Leu Ser Pro
        115                 120                 125

Ile Val Asp Asp Pro Asp Lys Ala Phe Met Ser Pro Val Met Arg Ala
    130                 135                 140

Ala Val Arg Asn Val Ala Lys Tyr Phe Pro Thr Ala Ile Val Ser Gly
145                 150                 155                 160

Arg Ser Arg Lys Lys Val Phe Glu Phe Val Lys Leu Thr Glu Leu Tyr
                165                 170                 175

Tyr Ala Gly Ser His Gly Met Asp Ile Val Thr Ser Ala Ala Ala His
            180                 185                 190

Ala Thr Glu Lys Cys Lys Glu Ala Asn Leu Phe Gln Pro Ala Cys Glu
        195                 200                 205

Phe Leu Pro Met Ile Asn Glu Val Ser Lys Cys Leu Val Glu Val Thr
    210                 215                 220

Ser Ser Ile Glu Gly Ala Arg Val Glu Asn Asn Lys Phe Cys Val Ser
225                 230                 235                 240

Val His Tyr Arg Asn Val Ala Glu Lys Asp Trp Lys Val Val Ala Gly
                245                 250                 255

Leu Val Lys Gln Val Leu Glu Ala Phe Pro Arg Leu Lys Val Thr Asn
            260                 265                 270

Gly Arg Met Val Leu Glu Val Arg Pro Val Ile Asp Trp Asp Lys Gly
        275                 280                 285

Lys Ala Val Glu Phe Leu Leu Arg Ser Leu Gly Leu Ser Asp Ser Glu
    290                 295                 300

Asp Val Val Pro Ile Tyr Ile Gly Asp Asp Arg Thr Asp Glu Asp Ala
305                 310                 315                 320

Phe Lys Val Leu Arg Glu Arg Ser Cys Gly Tyr Gly Ile Leu Val Ser
                325                 330                 335

Gln Val Pro Lys Asp Thr Glu Ala Phe Tyr Ser Val Arg Asp Pro Ser
            340                 345                 350

Glu Val Met Gly Phe Leu Asn Ser Leu Val Arg Trp Lys Lys His Pro
        355                 360                 365

Leu

<210> SEQ ID NO 55
<211> LENGTH: 382
<212> TYPE: PRT
<213> ORGANISM: Glycine max

<400> SEQUENCE: 55

Met Asp Leu Lys Pro Asn Leu Asn Pro Val Leu Thr Asp Ala Thr Pro
  1               5                  10                  15

Leu Thr Arg Ser Arg Leu Gly Val Pro Ser Gly Leu Ser Pro Tyr Ser
                 20                  25                  30

Pro Ile Gly Ala Thr Phe Pro His Gly Asn Met Leu Ala Ile Pro Arg
             35                  40                  45

Lys Lys Thr Gly Ile Leu Asp Asp Phe Arg Ser Ser Gly Trp Leu Asp
         50                  55                  60
```

```
Ala Met Lys Ser Ser Ser Pro Thr His Thr Lys Val Ser Lys Asp Val
 65                  70                  75                  80

Ser His Gly Ile Gly Ser Pro Asp Ser Ala Tyr Ser Thr Trp Leu Leu
                 85                  90                  95

Lys Phe Pro Ser Ala Leu Ala Ser Phe Asp Gln Ile Thr Asn Cys Ala
            100                 105                 110

Lys Gly Lys Arg Ile Ala Leu Phe Leu Asp Tyr Asp Gly Thr Leu Ser
        115                 120                 125

Pro Ile Val Asp Asn Pro Asp Ser Ala Phe Met Ser Asp Asn Met Arg
    130                 135                 140

Ala Ala Val Lys Ile Val Ala Glu Tyr Phe Pro Thr Ala Ile Ile Ser
145                 150                 155                 160

Gly Arg Ser Arg Asp Lys Val Tyr Glu Phe Val Gly Val Ser Asp Leu
                165                 170                 175

Cys Tyr Ala Gly Ser His Gly Met Asp Ile Ile Gly Pro Ser Arg Gln
            180                 185                 190

Ser Ile Ser Asp Asn His Pro Asp Cys Ile Ser Ser Ala Asp Lys Gln
        195                 200                 205

Gly Val Glu Val Asn Leu Phe Gln Pro Ala Ala Glu Phe Leu Pro Met
    210                 215                 220

Ile Asn Glu Val Leu Gly Leu Leu Met Glu Cys Thr Glu Asp Ile Glu
225                 230                 235                 240

Gly Ala Thr Val Glu Asn Asn Lys Phe Cys Val Ser Val His Tyr Arg
                245                 250                 255

Asn Val Asp Glu Glu Ser Trp Gln Ile Val Gly Gln Arg Val Tyr Asp
            260                 265                 270

Val Leu Lys Glu Tyr Pro Arg Leu Arg Leu Thr His Gly Arg Lys Val
        275                 280                 285

Leu Glu Val Arg Pro Val Ile Asp Trp Asp Lys Gly Lys Ala Val Thr
    290                 295                 300

Phe Leu Leu Glu Ser Leu Gly Leu Asn Cys Asp Asp Val Leu Ala Ile
305                 310                 315                 320

Tyr Val Gly Asp Asp Arg Thr Asp Glu Asp Ala Phe Lys Val Leu Lys
                325                 330                 335

Glu Ala Asn Lys Gly Cys Gly Ile Leu Val Ser Arg Ala Pro Lys Glu
            340                 345                 350

Ser Asn Ala Ile Tyr Ser Leu Arg Asp Pro Ser Glu Val Met Glu Phe
        355                 360                 365

Leu Thr Ser Leu Ala Glu Trp Lys Ser Ser Ile Gln Ala Arg
    370                 375                 380
```

<210> SEQ ID NO 56
<211> LENGTH: 18
<212> TYPE: DNA
<213> ORGANISM: Artificial
<220> FEATURE:
<223> OTHER INFORMATION: NS487 primer

<400> SEQUENCE: 56
cgagccatga cgaagcac                                                 18

<210> SEQ ID NO 57
<211> LENGTH: 21
<212> TYPE: DNA
<213> ORGANISM: Artificial
<220> FEATURE:
<223> OTHER INFORMATION: NS429 primer -continued

<400> SEQUENCE: 57
ataagcgcct ctttgctgtt g                                             21

<210> SEQ ID NO 58
<211> LENGTH: 20
<212> TYPE: DNA
<213> ORGANISM: Artificial
<220> FEATURE:
<223> OTHER INFORMATION: NS483 primer

<400> SEQUENCE: 58
ggcgactgga tggagaagca                                               20

<210> SEQ ID NO 59
<211> LENGTH: 39
<212> TYPE: DNA
<213> ORGANISM: Artificial
<220> FEATURE:
<223> OTHER INFORMATION: NS485 primer

<400> SEQUENCE: 59
gtgcgcggat ccagccatga cgaagcacgc cgcctactc                          39

<210> SEQ ID NO 60
<211> LENGTH: 34
<212> TYPE: DNA
<213> ORGANISM: Artificial
<220> FEATURE:
<223> OTHER INFORMATION: NS488 primer

<400> SEQUENCE: 60
cttctcgaat tctcagccgt gctcggcgtc ggcg                               34

<210> SEQ ID NO 61
<211> LENGTH: 398
<212> TYPE: PRT
<213> ORGANISM: Artificial
<220> FEATURE:
<223> OTHER INFORMATION: His-tagged RA3 protein

<400> SEQUENCE: 61

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Thr Leu Arg Ala Met Thr Lys His Ala Ala Tyr Ser Ser Glu Asp
        35                  40                  45

Val Val Ala Ala Val Ala Ala Pro Ala Pro Ala Gly Arg His Phe Thr
    50                  55                  60

Ser Phe Gln Ala Leu Lys Gly Ala Pro Leu Asp Cys Lys Lys His Ala
65                  70                  75                  80

Ala Val Asp Leu Ser Ala Ser Gly Ala Ala Val Val Gly Gly Gly Pro
                85                  90                  95

Trp Phe Glu Ser Met Lys Ala Ser Ser Pro Arg Arg Ala Ala Asp Ala
            100                 105                 110

Glu His Gly Asp Trp Met Glu Lys His Pro Ser Ala Leu Ala Gln Phe
        115                 120                 125

Glu Pro Leu Leu Ala Ala Ala Lys Gly Lys Gln Ile Val Met Phe Leu
    130                 135                 140

Asp Tyr Asp Gly Thr Leu Ser Pro Ile Val Glu Asp Pro Asp Arg Ala

```
            145                 150                 155                 160
Val Met Ser Glu Glu Met Arg Glu Ala Val Arg Arg Val Ala Glu His
                165                 170                 175
Phe Pro Thr Ala Ile Val Ser Gly Arg Cys Arg Asp Lys Val Leu Asn
                180                 185                 190
Phe Val Lys Leu Thr Glu Leu Tyr Tyr Ala Gly Ser His Gly Met Asp
                195                 200                 205
Ile Gln Gly Pro Ala Ala Cys Arg Gln Pro Asn His Val Gln Gln Ala
            210                 215                 220
Glu Ala Ala Val His Tyr Gln Ala Ala Ser Glu Phe Leu Pro Val
225                 230                 235                 240
Ile Glu Glu Val Phe Arg Thr Leu Thr Ala Lys Met Glu Ser Ile Ala
                245                 250                 255
Gly Ala Arg Val Glu His Asn Lys Tyr Cys Leu Ser Val His Phe Arg
                260                 265                 270
Cys Val Arg Glu Glu Trp Asn Ala Val Asn Glu Val Arg Ser
                275                 280                 285
Val Leu Arg Glu Tyr Pro Asn Leu Lys Leu Thr His Gly Arg Lys Val
            290                 295                 300
Leu Glu Ile Arg Pro Ser Ile Lys Trp Asp Lys Gly Lys Ala Leu Glu
305                 310                 315                 320
Phe Leu Lys Ser Leu Gly Tyr Ala Gly Arg Asn Asp Val Phe Pro
                325                 330                 335
Ile Tyr Ile Gly Asp Asp Arg Thr Asp Glu Asp Ala Phe Lys Val Leu
            340                 345                 350
Arg Asn Met Gly Gln Gly Ile Gly Ile Leu Val Ser Lys Leu Pro Lys
                355                 360                 365
Glu Thr Ala Ala Ser Tyr Ser Leu Ser Asp Pro Ala Glu Val Lys Glu
            370                 375                 380
Phe Leu Arg Lys Leu Ala Asn Lys Lys Gly Ala Arg Gln Pro
385                 390                 395

<210> SEQ ID NO 62
<211> LENGTH: 319
<212> TYPE: PRT
<213> ORGANISM: Artificial
<220> FEATURE:
<223> OTHER INFORMATION: His-tagged RA3 TPP-domain fragment

<400> SEQUENCE: 62

Met Arg Gly Ser His His His His His His Gly Met Ala Ser Met Thr
1               5                   10                  15
Gly Gly Gln Gln Met Gly Arg Asp Leu Tyr Asp Asp Asp Lys Asp
            20                  25                  30
Pro Thr Leu Gly Asp Trp Met Glu Lys His Pro Ser Ala Leu Ala Gln
            35                  40                  45
Phe Glu Pro Leu Leu Ala Ala Ala Lys Gly Lys Gln Ile Val Met Phe
        50                  55                  60
Leu Asp Tyr Asp Gly Thr Leu Ser Pro Ile Val Glu Asp Pro Asp Arg
65                  70                  75                  80
Ala Val Met Ser Glu Glu Met Arg Glu Ala Val Arg Arg Val Ala Glu
                85                  90                  95
His Phe Pro Thr Ala Ile Val Ser Gly Arg Cys Arg Asp Lys Val Leu
                100                 105                 110
Asn Phe Val Lys Leu Thr Glu Leu Tyr Tyr Ala Gly Ser His Gly Met
```

```
                115                 120                 125
Asp Ile Gln Gly Pro Ala Ala Cys Arg Gln Pro Asn His Val Gln Gln
    130                 135                 140

Ala Glu Ala Ala Val His Tyr Gln Ala Ala Ser Glu Phe Leu Pro
145                 150                 155                 160

Val Ile Glu Glu Val Phe Arg Thr Leu Thr Ala Lys Met Glu Ser Ile
                165                 170                 175

Ala Gly Ala Arg Val Glu His Asn Lys Tyr Cys Leu Ser Val His Phe
                180                 185                 190

Arg Cys Val Arg Glu Glu Trp Asn Ala Val Asn Glu Glu Val Arg
                195                 200                 205

Ser Val Leu Arg Glu Tyr Pro Asn Leu Lys Leu Thr His Gly Arg Lys
    210                 215                 220

Val Leu Glu Ile Arg Pro Ser Ile Lys Trp Asp Lys Gly Lys Ala Leu
225                 230                 235                 240

Glu Phe Leu Leu Lys Ser Leu Gly Tyr Ala Gly Arg Asn Asp Val Phe
                245                 250                 255

Pro Ile Tyr Ile Gly Asp Asp Arg Thr Asp Glu Asp Ala Phe Lys Val
                260                 265                 270

Leu Arg Asn Met Gly Gln Gly Ile Gly Ile Leu Val Ser Lys Leu Pro
                275                 280                 285

Lys Glu Thr Ala Ala Ser Tyr Ser Leu Ser Asp Pro Ala Glu Val Lys
    290                 295                 300

Glu Phe Leu Arg Lys Leu Ala Asn Lys Lys Gly Ala Arg Gln Pro
305                 310                 315

<210> SEQ ID NO 63
<211> LENGTH: 112
<212> TYPE: PRT
<213> ORGANISM: Artificial
<220> FEATURE:
<223> OTHER INFORMATION: His-tagged RA3 Amino-terminal Fragment

<400> SEQUENCE: 63

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Ala Met Thr Lys His Ala Ala Tyr Ser Ser Glu Asp Val Val Ala
            35                  40                  45

Ala Val Ala Ala Pro Ala Pro Ala Gly Arg His Phe Thr Ser Phe Gln
    50                  55                  60

Ala Leu Lys Gly Ala Pro Leu Asp Cys Lys Lys His Ala Ala Val Asp
65                  70                  75                  80

Leu Ser Ala Ser Gly Ala Ala Val Val Gly Gly Pro Trp Phe Glu
                85                  90                  95

Ser Met Lys Ala Ser Ser Pro Arg Arg Ala Ala Asp Ala Glu His Gly
            100                 105                 110

<210> SEQ ID NO 64
<211> LENGTH: 44
<212> TYPE: DNA
<213> ORGANISM: Artificial
<220> FEATURE:
<223> OTHER INFORMATION: NS489 primer

<400> SEQUENCE: 64
```

-continued aaggaaaaaa gcggccgcgc catgacgaag cacgccgcct actc          44

<210> SEQ ID NO 65
<211> LENGTH: 42
<212> TYPE: DNA
<213> ORGANISM: Artificial
<220> FEATURE:
<223> OTHER INFORMATION: NS490 primer

<400> SEQUENCE: 65
acgaggtcgt gcctgccgct catggttggc gcgccccctt ct          42

<210> SEQ ID NO 66
<211> LENGTH: 47
<212> TYPE: DNA
<213> ORGANISM: Artificial
<220> FEATURE:
<223> OTHER INFORMATION: NS500 primer

<400> SEQUENCE: 66
cgcgccgccg gcggccgcga catggactgg atggagaagc acccgtc          47

<210> SEQ ID NO 67
<211> LENGTH: 855
<212> TYPE: DNA
<213> ORGANISM: Artificial
<220> FEATURE:
<223> OTHER INFORMATION: Encoding RA3 TPP-domain fragment expressed in
      yeast
<220> FEATURE:
<221> NAME/KEY: CDS
<222> LOCATION: (1)..(855)

<400> SEQUENCE: 67

```
atg gac tgg atg gag aag cac ccg tcc gca ttg gcc cag ttc gag ccg      48
Met Asp Trp Met Glu Lys His Pro Ser Ala Leu Ala Gln Phe Glu Pro
 1               5                  10                  15 ctg ctt gcc gcc gcc aag ggg aag cag atc gtg atg ttc ctg gac tac      96
Leu Leu Ala Ala Ala Lys Gly Lys Gln Ile Val Met Phe Leu Asp Tyr
            20                  25                  30 gac ggc acc ctg tca ccg atc gtc gag gac ccc gac cgc gcc gtc atg     144
Asp Gly Thr Leu Ser Pro Ile Val Glu Asp Pro Asp Arg Ala Val Met
        35                  40                  45 tcg gag gag atg aga gaa gcc gtg cgg cgc gtc gcc gag cac ttc ccc     192
Ser Glu Glu Met Arg Glu Ala Val Arg Arg Val Ala Glu His Phe Pro
    50                  55                  60 acc gcg att gtg agc gga aga tgc agg gac aag gtg ctc aac ttc gtg     240
Thr Ala Ile Val Ser Gly Arg Cys Arg Asp Lys Val Leu Asn Phe Val
65                  70                  75                  80 aag ctg acg gag ctg tac tac gcc ggg agc cat ggc atg gac atc cag     288
Lys Leu Thr Glu Leu Tyr Tyr Ala Gly Ser His Gly Met Asp Ile Gln
                85                  90                  95 ggc ccc gcc gcc tgc agg cag ccc aac cac gtc cag cag gct gaa gcc     336
Gly Pro Ala Ala Cys Arg Gln Pro Asn His Val Gln Gln Ala Glu Ala
            100                 105                 110 gca gct gtc cat tac caa gct gcg agt gag ttc ctg ccg gtc atc gaa     384
Ala Ala Val His Tyr Gln Ala Ala Ser Glu Phe Leu Pro Val Ile Glu
        115                 120                 125 gag gtg ttc cgc acg ctg acg gcc aag atg gag tcc atc gcc ggc gcc     432
Glu Val Phe Arg Thr Leu Thr Ala Lys Met Glu Ser Ile Ala Gly Ala
    130                 135                 140 agg gtg gag cac aac aag tac tgc ctg tcc gtc cac ttc cgc tgc gtc     480
Arg Val Glu His Asn Lys Tyr Cys Leu Ser Val His Phe Arg Cys Val
145                 150                 155                 160
```

```
cgg gag gag gaa tgg aat gcc gtg aac gag gag gtc agg tcg gtg ctc     528
Arg Glu Glu Glu Trp Asn Ala Val Asn Glu Glu Val Arg Ser Val Leu
                165                 170                 175 agg gag tac ccg aac ctc aag ctc act cac ggc aga aag gtg ctg gag     576
Arg Glu Tyr Pro Asn Leu Lys Leu Thr His Gly Arg Lys Val Leu Glu
            180                 185                 190 att cgt ccg tcc atc aag tgg gac aag ggc aag gcc ctc gag ttc ttg     624
Ile Arg Pro Ser Ile Lys Trp Asp Lys Gly Lys Ala Leu Glu Phe Leu
        195                 200                 205 ctc aag tct ctt ggc tat gct ggg cgc aac gac gtc ttc ccg att tac     672
Leu Lys Ser Leu Gly Tyr Ala Gly Arg Asn Asp Val Phe Pro Ile Tyr
    210                 215                 220 atc gga gat gat cgc act gac gag gac gct ttc aag gtg ctc cgc aac     720
Ile Gly Asp Asp Arg Thr Asp Glu Asp Ala Phe Lys Val Leu Arg Asn
225                 230                 235                 240 atg ggg cag ggc atc gga atc ctg gtg tcc aag ctt cct aag gag acg     768
Met Gly Gln Gly Ile Gly Ile Leu Val Ser Lys Leu Pro Lys Glu Thr
                245                 250                 255 gcg gca tcc tac tcg ctg agt gac cct gcc gag gtc aag gag ttc ctc     816
Ala Ala Ser Tyr Ser Leu Ser Asp Pro Ala Glu Val Lys Glu Phe Leu
            260                 265                 270 cgc aag ctg gcc aat aag aag ggg gcg cgc caa cca tga                 855
Arg Lys Leu Ala Asn Lys Lys Gly Ala Arg Gln Pro
        275                 280

<210> SEQ ID NO 68
<211> LENGTH: 284
<212> TYPE: PRT
<213> ORGANISM: Artificial
<220> FEATURE:
<223> OTHER INFORMATION: Synthetic Construct

<400> SEQUENCE: 68

Met Asp Trp Met Glu Lys His Pro Ser Ala Leu Ala Gln Phe Glu Pro
1               5                   10                  15

Leu Leu Ala Ala Ala Lys Gly Lys Gln Ile Val Met Phe Leu Asp Tyr
                20                  25                  30

Asp Gly Thr Leu Ser Pro Ile Val Glu Asp Pro Asp Arg Ala Val Met
            35                  40                  45

Ser Glu Glu Met Arg Glu Ala Val Arg Arg Val Ala Glu His Phe Pro
        50                  55                  60

Thr Ala Ile Val Ser Gly Arg Cys Arg Asp Lys Val Leu Asn Phe Val
65                  70                  75                  80

Lys Leu Thr Glu Leu Tyr Tyr Ala Gly Ser His Gly Met Asp Ile Gln
                85                  90                  95

Gly Pro Ala Ala Cys Arg Gln Pro Asn His Val Gln Gln Ala Glu Ala
            100                 105                 110

Ala Ala Val His Tyr Gln Ala Ala Ser Glu Phe Leu Pro Val Ile Glu
        115                 120                 125

Glu Val Phe Arg Thr Leu Thr Ala Lys Met Glu Ser Ile Ala Gly Ala
    130                 135                 140

Arg Val Glu His Asn Lys Tyr Cys Leu Ser Val His Phe Arg Cys Val
145                 150                 155                 160

Arg Glu Glu Glu Trp Asn Ala Val Asn Glu Glu Val Arg Ser Val Leu
                165                 170                 175

Arg Glu Tyr Pro Asn Leu Lys Leu Thr His Gly Arg Lys Val Leu Glu
            180                 185                 190
```

```
Ile Arg Pro Ser Ile Lys Trp Asp Lys Gly Lys Ala Leu Glu Phe Leu
            195                 200                 205

Leu Lys Ser Leu Gly Tyr Ala Gly Arg Asn Asp Val Phe Pro Ile Tyr
        210                 215                 220

Ile Gly Asp Asp Arg Thr Asp Glu Asp Ala Phe Lys Val Leu Arg Asn
225                 230                 235                 240

Met Gly Gln Gly Ile Gly Ile Leu Val Ser Lys Leu Pro Lys Glu Thr
                245                 250                 255

Ala Ala Ser Tyr Ser Leu Ser Asp Pro Ala Glu Val Lys Glu Phe Leu
            260                 265                 270

Arg Lys Leu Ala Asn Lys Lys Gly Ala Arg Gln Pro
        275                 280
```

<210> SEQ ID NO 69
<211> LENGTH: 295
<212> TYPE: PRT
<213> ORGANISM: Artificial
<220> FEATURE:
<223> OTHER INFORMATION: SRA TPP-domain fragment

<400> SEQUENCE: 69

```
Asp Trp Met Glu Lys His Pro Ser Ala Leu Ala Ala Phe Glu Ser Val
1               5                   10                  15

Leu Ala Ala Lys Gly Lys Ile Val Met Phe Leu Asp Tyr Asp
            20                  25                  30

Gly Thr Leu Ser Pro Ile Val Arg Asp Pro Asp Ser Ala Val Met Ser
            35                  40                  45

Glu Glu Met Arg Asp Ala Val Arg Gly Val Ala Glu His Phe Pro Thr
        50                  55                  60

Ala Ile Val Ser Gly Arg Cys Arg Asp Lys Val Phe Asn Phe Val Lys
65                  70                  75                  80

Leu Ala Glu Leu Tyr Tyr Ala Gly Ser His Gly Met Asp Ile Lys Gly
                85                  90                  95

Pro Thr Ala Gln Ser Lys His Thr Lys Ala Lys Ala Gly Ala Val Leu
            100                 105                 110

Cys Gln Pro Ala Arg Ala Phe Leu Pro Val Ile Glu Glu Val Tyr Arg
        115                 120                 125

Ala Leu Thr Ala Ser Thr Ala Pro Ile Pro Gly Ala Thr Val Glu Asn
    130                 135                 140

Asn Lys Phe Cys Leu Ser Val His Phe Arg Cys Val Gln Glu Glu Lys
145                 150                 155                 160

Trp Arg Ala Leu Glu Glu Gln Val Arg Ser Val Leu Lys Glu Tyr Pro
                165                 170                 175

Asp Leu Arg Leu Thr Lys Gly Arg Lys Val Leu Glu Ile Arg Pro Ser
            180                 185                 190

Ile Lys Trp Asp Lys Gly Asn Ala Leu Gln Phe Leu Leu Glu Ser Leu
        195                 200                 205

Gly Phe Ala Gly Ser Asn Ser Val Phe Pro Ile Tyr Ile Gly Asp Asp
    210                 215                 220

Ser Thr Asp Glu Asp Ala Phe Lys Val Leu Arg Asn Leu Gly Gln Gly
225                 230                 235                 240

Ile Gly Ile Leu Val Ser Lys Ile Pro Lys Glu Thr Arg Ala Ser Tyr
                245                 250                 255

Ser Leu Arg Glu Pro Ser Glu Val Ala Thr Leu Pro Thr Ala Thr Ser
            260                 265                 270
```

```
Tyr Tyr Cys Thr Val Glu Glu Phe Leu Arg Lys Leu Val Ser Trp Ser
            275                 280                 285

Lys Glu Ser Arg Gln Arg Asp
        290             295

<210> SEQ ID NO 70
<211> LENGTH: 294
<212> TYPE: PRT
<213> ORGANISM: Artificial
<220> FEATURE:
<223> OTHER INFORMATION: Arabidopsis AtTPPA TPP-domain fragment

<400> SEQUENCE: 70

Met Thr Tyr Arg Glu Trp Met Gln Leu Lys Tyr Pro Ser Ala Leu Thr
1               5                   10                  15

Ser Phe Glu Lys Ile Met Ser Phe Ala Lys Gly Lys Arg Ile Ala Leu
            20                  25                  30

Phe Leu Asp Tyr Asp Gly Thr Leu Ser Pro Ile Val Glu Glu Pro Asp
        35                  40                  45

Cys Ala Tyr Met Ser Ser Ala Met Arg Ser Ala Val Gln Asn Val Ala
    50                  55                  60

Lys Tyr Phe Pro Thr Ala Ile Ile Ser Gly Arg Ser Arg Asp Lys Val
65                  70                  75                  80

Tyr Glu Phe Val Asn Leu Ser Glu Leu Tyr Tyr Ala Gly Ser His Gly
                85                  90                  95

Met Asp Ile Met Ser Pro Ala Gly Glu Ser Leu Asn His Glu His Ser
            100                 105                 110

Arg Thr Val Ser Val Tyr Glu Gln Gly Lys Asp Val Asn Leu Phe Gln
        115                 120                 125

Pro Ala Ser Glu Phe Leu Pro Met Ile Asp Lys Val Leu Cys Ser Leu
    130                 135                 140

Ile Glu Ser Thr Lys Asp Ile Lys Gly Val Lys Val Glu Asp Asn Lys
145                 150                 155                 160

Phe Cys Ile Ser Val His Tyr Arg Asn Val Glu Glu Lys Asn Trp Thr
                165                 170                 175

Leu Val Ala Gln Cys Val Asp Asp Val Ile Arg Thr Tyr Pro Lys Leu
            180                 185                 190

Arg Leu Thr His Gly Arg Lys Val Leu Glu Ile Arg Pro Val Ile Asp
        195                 200                 205

Trp Asp Lys Gly Lys Ala Val Thr Phe Leu Leu Glu Ser Leu Gly Leu
    210                 215                 220

Asn Asn Cys Glu Asp Val Leu Pro Ile Tyr Val Gly Asp Asp Arg Thr
225                 230                 235                 240

Asp Glu Asp Ala Phe Lys Val Leu Arg Asp Gly Pro Asn His Gly Tyr
                245                 250                 255

Gly Ile Leu Val Ser Ala Val Pro Lys Asp Ser Asn Ala Phe Tyr Ser
            260                 265                 270

Leu Arg Asp Pro Ser Glu Val Met Glu Phe Leu Lys Ser Leu Val Thr
        275                 280                 285

Trp Lys Arg Ser Met Gly
    290

<210> SEQ ID NO 71
<211> LENGTH: 283
<212> TYPE: PRT
<213> ORGANISM: Artificial
<220> FEATURE:
```

-continued

<223> OTHER INFORMATION: Arabidopsis AtTPPB TPP-domain fragment

<400> SEQUENCE: 71

```
Lys Thr Ser Trp Ile Val Arg Phe Pro Ser Ala Leu Asn Met Phe Asp
1               5                   10                  15

Glu Ile Val Asn Ala Ala Lys Gly Lys Gln Ile Val Met Phe Leu Asp
                20                  25                  30

Tyr Asp Gly Thr Leu Ser Pro Ile Val Glu Asp Pro Asp Lys Ala Phe
            35                  40                  45

Ile Thr His Glu Met Arg Glu Val Val Lys Asp Val Ala Ser Asn Phe
        50                  55                  60

Pro Thr Ala Ile Val Thr Gly Arg Ser Ile Glu Lys Val Arg Ser Phe
65                  70                  75                  80

Val Gln Val Asn Glu Ile Tyr Tyr Ala Gly Ser His Gly Met Asp Ile
                85                  90                  95

Glu Gly Pro Thr Asn Glu Asn Ser Asn Gly Gln Ser Asn Glu Arg Val
            100                 105                 110

Leu Phe Gln Pro Ala Arg Glu Phe Leu Pro Met Ile Glu Lys Val Val
        115                 120                 125

Asn Ile Leu Glu Glu Lys Thr Lys Trp Ile Pro Gly Ala Met Val Glu
    130                 135                 140

Asn Asn Lys Phe Cys Leu Ser Val His Phe Arg Arg Val Asp Glu Lys
145                 150                 155                 160

Arg Trp Pro Ala Leu Ala Glu Val Val Lys Ser Val Leu Ile Asp Tyr
                165                 170                 175

Pro Lys Leu Lys Leu Thr Gln Gly Arg Lys Val Leu Glu Ile Arg Pro
            180                 185                 190

Thr Ile Lys Trp Asp Lys Gly Gln Ala Leu Asn Phe Leu Leu Lys Ser
        195                 200                 205

Leu Gly Tyr Glu Asn Ser Asp Asp Val Val Pro Val Tyr Ile Gly Asp
    210                 215                 220

Asp Arg Thr Asp Glu Asp Ala Phe Lys Val Leu Arg Glu Arg Gly Gln
225                 230                 235                 240

Gly Phe Gly Ile Leu Val Ser Lys Val Pro Lys Asp Thr Asn Ala Ser
                245                 250                 255

Tyr Ser Leu Gln Asp Pro Ser Gln Val Asn Lys Phe Leu Glu Arg Leu
            260                 265                 270

Val Glu Trp Lys Arg Lys Thr Val Gly Glu Glu
        275                 280
```